US007108974B2

(12) United States Patent
Ecker et al.

(10) Patent No.: US 7,108,974 B2

(45) Date of Patent: Sep. 19, 2006

(54) METHOD FOR RAPID DETECTION AND IDENTIFICATION OF BIOAGENTS

(75) Inventors: David J. Ecker, Encinitas, CA (US); Richard Griffey, Vista, CA (US); Rangarajan Sampath, San Diego, CA (US); Steven Hofstadler, Oceanside, CA (US); John McNeil, La Jolla, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 130 days.

(21) Appl. No.: 10/156,608

(22) Filed: May 24, 2002

(65) Prior Publication Data

US 2003/0124556 A1 Jul. 3, 2003

Related U.S. Application Data

(62) Division of application No. 09/798,007, filed on Mar. 2, 2001, now abandoned.

(51) Int. Cl.
*C12Q 1/68* (2006.01)
*C12P 19/34* (2006.01)
*C07H 21/02* (2006.01)

(52) U.S. Cl. ........................ 435/6; 435/91.1; 435/91.2; 536/23.1

(58) Field of Classification Search .................... 435/6, 435/91.2, 91.1; 536/23.1
See application file for complete search history.

(56) References Cited

U.S. PATENT DOCUMENTS 5,484,908 A 1/1996 Froehler et al. ......... 536/24.31
5,502,177 A 3/1996 Matteucci et al. ......... 536/26.6
5,503,980 A 4/1996 Cantor
5,527,675 A 6/1996 Coull et al.
5,547,835 A 8/1996 Köster ........................... 435/6
5,580,733 A 12/1996 Levis et al.
5,605,798 A 2/1997 Köster ........................... 435/6
5,622,824 A 4/1997 Köster ........................... 435/6
5,625,184 A 4/1997 Vestal et al.
5,645,985 A 7/1997 Froehler et al. ............... 435/6
5,686,242 A 11/1997 Bruice et al.
5,691,141 A 11/1997 Köster ........................... 435/6
5,700,642 A 12/1997 Monforte et al.
5,763,588 A 6/1998 Matteucci et al. ......... 536/22.1
5,770,367 A 6/1998 Southern et al.
5,777,324 A 7/1998 Hillenkamp
5,830,653 A 11/1998 Froehler et al. ............... 435/6
5,830,655 A 11/1998 Monforte et al.
5,849,492 A 12/1998 Rogan ........................... 435/6
5,851,765 A 12/1998 Koster
5,864,137 A 1/1999 Becker et al.
5,869,242 A 2/1999 Kamb
5,871,697 A 2/1999 Rothberg et al.
5,872,003 A 2/1999 Köster ..................... 435/283.1
5,876,936 A 3/1999 Ju
5,928,906 A 7/1999 Koster et al.
5,965,363 A 10/1999 Monforte et al. .............. 435/6
5,981,176 A 11/1999 Wallace
5,994,066 A 11/1999 Bergeron et al.
6,001,564 A 12/1999 Bergeron et al.
6,005,096 A 12/1999 Matteucci et al. ......... 536/26.6
6,007,992 A 12/1999 Lin et al. ....................... 435/6
6,028,183 A 2/2000 Lin et al. ................... 536/22.1
6,043,031 A 3/2000 Koster et al.
6,046,005 A 4/2000 Ju et al.
6,051,378 A 4/2000 Monforte et al.
6,054,278 A 4/2000 Dodge et al.
6,074,823 A 6/2000 Koster
6,090,558 A 7/2000 Butler et al.
6,104,028 A 8/2000 Hunter et al.
6,111,251 A 8/2000 Hillenkamp
6,140,053 A 10/2000 Koster
6,146,144 A 11/2000 Fowler et al.
6,153,389 A 11/2000 Haarer et al.
6,159,681 A 12/2000 Zebala
6,197,498 B1 3/2001 Koster
6,218,118 B1 4/2001 Sampson et al.
6,221,587 B1 4/2001 Ecker et al.
6,221,601 B1 4/2001 Koster et al.
6,221,605 B1 4/2001 Koster
6,225,450 B1 5/2001 Koster
6,235,476 B1 5/2001 Bergmann et al.
6,235,478 B1 5/2001 Koster
6,235,480 B1 5/2001 Shultz et al.
6,238,871 B1 5/2001 Koster
6,238,927 B1 5/2001 Abrams et al.
6,258,538 B1 7/2001 Koster et al.

(Continued)

FOREIGN PATENT DOCUMENTS

DE 19802905 7/1999

(Continued)

OTHER PUBLICATIONS

Muddiman et al (Anal. Chem. (1996) 68:3705-3712).*

(Continued)

*Primary Examiner*—Jeffrey Fredman
(74) *Attorney, Agent, or Firm*—Isis Patent Department; Cozen O'Connor, P.C.

(57) ABSTRACT

Method for detecting and identifying unknown bioagents, including bacteria, viruses and the like, by a combination of nucleic acid amplification and molecular weight determination using primers which hybridize to conserved sequence regions of nucleic acids derived from a bioagent and which bracket variable sequence regions that uniquely identify the bioagent. The result is a "base composition signature" (BCS) which is then matched against a database of base composition signatures, by which the bioagent is identified.

29 Claims, 23 Drawing Sheets

U.S. PATENT DOCUMENTS

| | | | |
|---|---|---|---|
| 6,265,716 | B1 | 7/2001 | Hunter et al. |
| 6,268,129 | B1 | 7/2001 | Gut et al. |
| 6,268,131 | B1 | 7/2001 | Kang et al. |
| 6,268,144 | B1 | 7/2001 | Koster |
| 6,268,146 | B1 | 7/2001 | Shultz et al. |
| 6,270,973 | B1 | 8/2001 | Lewis et al. |
| 6,270,974 | B1 | 8/2001 | Shultz et al. |
| 6,277,573 | B1 | 8/2001 | Koster |
| 6,277,578 | B1 | 8/2001 | Shultz et al. |
| 6,300,076 | B1 | 10/2001 | Koster |
| 6,312,893 | B1 | 11/2001 | Van Ness et al. |
| 6,312,902 | B1 | 11/2001 | Shultz et al. |
| 6,361,940 | B1 | 3/2002 | Van Ness et al. |
| 6,372,424 | B1 | 4/2002 | Brow et al. |
| 6,391,551 | B1 | 5/2002 | Shultz et al. |
| 6,423,966 | B1 | 7/2002 | Hillenkamp et al. |
| 6,428,955 | B1 | 8/2002 | Koster et al. |
| 6,432,651 | B1 | 8/2002 | Hughes et al. |
| 6,436,635 | B1 | 8/2002 | Fu et al. |
| 6,436,640 | B1 | 8/2002 | Simmons et al. |
| 6,458,533 | B1 | 10/2002 | Felder et al. |
| 6,468,748 | B1 | 10/2002 | Monforte et al. |
| 6,475,736 | B1 | 11/2002 | Stanton, Jr. |
| 6,479,239 | B1 | 11/2002 | Anderson et al. |
| 6,500,621 | B1 | 12/2002 | Koster |
| 6,558,902 | B1 | 5/2003 | Hillenkamp |
| 6,566,055 | B1 | 5/2003 | Monforte et al. |
| 6,582,916 | B1 | 6/2003 | Schmidt et al. |
| 6,589,485 | B1 | 7/2003 | Koster |
| 6,602,662 | B1 | 8/2003 | Koster |
| 6,613,509 | B1 | 9/2003 | Chen |
| 6,623,928 | B1 | 9/2003 | Van Ness et al. |
| 6,682,889 | B1 | 1/2004 | Wang et al. |
| 2002/0045178 | A1 | 4/2002 | Cantor et al. |
| 2002/0137057 | A1 | 9/2002 | Wold et al. |
| 2002/0150903 | A1 | 10/2002 | Koster |
| 2002/0150927 | A1 | 10/2002 | Matray et al. |
| 2003/0017487 | A1 | 1/2003 | Xue et al. |
| 2003/0039976 | A1 | 2/2003 | Haff |
| 2003/0064483 | A1 | 4/2003 | Shaw et al. |
| 2003/0073112 | A1 | 4/2003 | Zhang et al. |
| 2003/0113745 | A1 | 6/2003 | Monforte et al. |
| 2003/0129589 | A1 | 7/2003 | Koster et al. |
| 2003/0134312 | A1 | 7/2003 | Burgoyne |
| 2003/0148284 | A1 | 8/2003 | Vision et al. |
| 2003/0175729 | A1 | 9/2003 | Van Eijk et al. |
| 2003/0194699 | A1 | 10/2003 | Lewis et al. |
| 2003/0203398 | A1 | 10/2003 | Bramucci et al. |
| 2003/0220844 | A1 | 11/2003 | Mamellos et al. |
| 2004/0005555 | A1 | 1/2004 | Rothman et al. |
| 2004/0038206 | A1 | 2/2004 | Zhang et al. |
| 2004/0038234 | A1 | 2/2004 | Gut et al. |
| 2004/0038385 | A1 | 2/2004 | Langlois et al. |

FOREIGN PATENT DOCUMENTS

| | | |
|---|---|---|
| DE | 19824280 | 12/1999 |
| DE | 19852167 | 5/2000 |
| EP | 1138782 | 10/2001 |
| EP | 1234888 | 8/2002 |
| EP | 1333101 | 8/2003 |
| GB | 2325002 | 11/1998 |
| GB | 2339905 | 2/2000 |
| WO | WO 93/03186 | 2/1993 |
| WO | WO 94/16101 | 7/1994 |
| WO | WO 94/21822 | 9/1994 |
| WO | WO 96/29431 | 9/1996 |
| WO | WO 96/32504 | 10/1996 |
| WO | WO 96/37630 | 11/1996 |
| WO | WO 97/33000 | 9/1997 |
| WO | WO 97/37041 | 10/1997 |
| WO | WO 98/03684 | 1/1998 |
| WO | WO 98/12355 | 3/1998 |
| WO | WO 98/14616 | 4/1998 |
| WO | WO 98/15652 | 4/1998 |
| WO | WO 98/20020 | 5/1998 |
| WO | WO 98/20157 | 5/1998 |
| WO | WO 98/20166 | 5/1998 |
| WO | WO 98/26095 | 6/1998 |
| WO | WO 98/31830 | 7/1998 |
| WO | WO 98/40520 | 9/1998 |
| WO | WO 98/54571 | 12/1998 |
| WO | WO 98/54751 | 12/1998 |
| WO | WO 99/05319 | 2/1999 |
| WO | WO 99/14375 | 3/1999 |
| WO | WO 99/29898 | 6/1999 |
| WO | WO 99/31278 | 6/1999 |
| WO | WO 99/57318 | 11/1999 |
| WO | WO 01/07648 | 2/2001 |
| WO | WO 01/23604 | 4/2001 |
| WO | WO 01/32930 | 5/2001 |
| WO | WO 01/51661 | 7/2001 |
| WO | WO 01/57263 | 8/2001 |
| WO | WO 02/10186 | 2/2002 |
| WO | WO 02/18641 | 3/2002 |
| WO | WO 02/21108 | 3/2002 |
| WO | WO 02/50307 | 6/2002 |
| WO | WO 02/57491 | 7/2002 |
| WO | WO 02/077278 | 10/2002 |
| WO | WO 02/099034 | 12/2002 |
| WO | WO 03/002750 | 1/2003 |
| WO | WO 03/008636 | 1/2003 |
| WO | WO 03/016546 | 2/2003 |
| WO | WO 03/060163 | 7/2003 |
| WO | WO 03/088979 | 10/2003 |
| WO | WO 03/097869 | 11/2003 |

OTHER PUBLICATIONS

Hurst et al (Anal. Chem. (1998) 70:2693-2698).*

Lacroix et al (J. Microbiol. Methods (1996) 26:61-71).*

Van Baar et al (FEMS Microbiol. Reviews (2000) 24:193-219).*

Boivin-Jahns (App. Envir. Microbiol. (1996) 62(9):3405-3412).*

Aaserud, D.J., et al., "Accurate base composition of double-strand DNA by mass spectrometry," *J. Am. Soc. Mass Spec.*, 1996, 7, 1266-1269.

Bowen, J.E., et al., "The native virulence plasmid combination affects the segregational stability of a theta-replicating shuttle vector in *Bacillus anthracis* var, New Hampshire," *J. Appl. Microbiol.*, 1999, 87, 270-278.

Hurst, G.B., et al., "Detection of bacterial DNA polymerase chain reaction products by matrix-assisted laser desorption/ionization mass spectrometry," *Rapid Commun. Mass Spec.*, 1996, 10, 377-382.

Loakes, D., et al., "Nitroindoles as universal bases," *Nucleosides and Nucleotides*, 1995, 14(3-5), 1001-1003.

Muddiman, D.C., et al., "Precise mass measurement of a double-stranded 500 base-pair (309 kDa) polymerase chain reaction product by negative ion electrospray ionization fourier transform ion cyclotron resonance mass spectrometry," *Rapid Commun. Mass Spec.*, 1999, 13, 1201-1204.

Muddiman, D.C., et al., "Length and base composition of PCR-amplified nucleic acids using mass measurements from electrospray ionization mass spectrometry," *Anal. Chem.*, 1997, 69, 1543-1549.

Sala, M., et al., "Ambiguous base pairing of the purine analogue 1-(2-deoxy-β-D -ribofuranosyl)-imidazole-4-carboxamide during PCR," *Nucl. Acids Res.*, 1996, 24(17), 3302-3306.

Van Aerschot, A., et al., "In search of acyclic analogues as universal nucleosides in degenerate probes," *Nucleosides and Nucleotides*, 1995, 14(3-5), 1053-1056.

Wunschel, D.S., et al., "Heterogeneity in *Bacillus cereus* PCR products detected by ESI-FTICR mass spectrometry," *Anal. Chem.*, 1998, 70, 1203-1207.

Mushegian, A.R., et al., "A minimal gene set for cellular life derived by comparison of complete bacterial genomes," *Proc. Natl. Acad. Sci. USA*, 1996, 93, 10268-10273.

Aaserud, D. J., et al., "Accurate base composition of double strand DNA by mass spectrometry," *J. Am. Soc. Mass Spectrom.* (1996) 7(12): 1266-1269.

Bahrmand, A. R. et al., "Use of restriction enzyme analysis of amplified DNA coding for the hsp65 gene and polymerase chain reaction with universal primer for rapid differentiation of mycobacterium species in the clinical laboratory," *Scand. J. Infect. Diseases* (1998) 30(5):477-80.

Bahrmand, A. R. et al., "Polymerase chain reaction of bacterial genomes with single universal primer: application to distinguishing mycobacteria species," *Mol. Cell. Probes* (1996) 10(2): 117-22.

Bastia, T. et al., "Organelle DNA analysis of Solanum and Brassica somatic hybrids by PCR with 'universal primers'," *Theoretical and Applied Genetics* (2001) 102(8): 1265-1272.

Bowen, J. E. et al., "The native virulence plasmid combination affects the segregational stability of a theta-replicating shuttle vector in *Bacillus anthracis* var. New Hampshire," *J Appl Microbiol.* (1999) 87(2): 270-8.

Campbell, W. P. et al., "Detection of California serogroup Bunyaviruses in tissue culture and mosquito pools by PCR," *J. Virol. Methods* (1996) 57(2): 175-9.

Cespedes, A. et al., "Polymerase chain reaction restriction fragment length polymorphism analysis of a short fragment of the cytochrome b gene for identification of flatfish species," *J. Food Protection* (1998) 61(12): 1684-5.

Chen, C. A. et al., "Universal primers for amplification of mitochondrial small subunit ribosomal RNA-encoding gene in scleractinian corals," *Marine Biotech.* (2000) 2(2): 146-153.

Chen, J. et al., "A universal PCR primer to detect members of the Potyviridae and its use to examine the taxonomic status of several members of the family," *Arch. Virol.* (2001) 146(4): 757-66.

Cho, M. et al., "Applications of the ribonuclease P (RNase P) RNA gene sequence for phylogenetic analysis of the gene Saccharomonospora," *Internat. J. of Sys. Bacteriol.* (1998) 48: 1223-1230.

Conrads, G. et al., "16S-23S rDNA internal transcribed spacer sequences for analysis of the phylogenetic relationships among species of the genus *Fusobacterium," International Journal of Systematic and Evolutionary Microbiology* (2002) 52(2): 493-499.

Cornel, A. J. et al., "Polymerase chain reaction species diagnostic assay for Anopheles quadrimaculatus cryptic species (Diptera: Culicidae) based on ribosomal DNA ITS2 sequences," *Journal of Medical Entomology* (1996) 33(1): 109-16.

Crain, P. F. et al., "Applications of mass spectrometry to the characterization of oligonucleotides and nucleic acids," *Curr Opin Biotechnol* (1998) 9(1): 25-34.

Dasen, G. et al., "Classification and identification of Propionibacteria based on 16S ribosomal RNA genes and PCR," *Systematic and Applied Microbiology* (1998) 21(2): 251-259.

Deforce, D. L. et al., "Analysis of oligonucleotides by ESI-MS," *Advances in Chromatography* (2000) 40: 539-566.

Deforce, D. L. D. et al., "Characterization of DNA Oligonucleotides by Coupling of Capillary Zone Electrophoresis to Electrospray Ionization Q-TOF Mass Spectrometry," *Anal. Chem.* (1998) 70(14): 3060-3068.

Demesure, B. et al., "A set of universal primers for amplification of polymorphic non-coding regions of mitochondrial and chloroplast DNA in plants," *Mol. Ecology* (1995) 4(1): 129-31.

Dinauer, D. M. et al., "Sequence-based typing of HLA class II DQBI," *Tissue Antigens* (2000) 55(4): 364-368.

Dubernet, S. et al., "A PCR-based method for identification of Lactobacilli at the genus level," *FEMS Microbiology Letters* (2002) 214(2): 271-275.

Figueiredo, L. T. M. et al., "Identification of Brazilian flaviviruses by a simplified reverse transcription-polymerase chain reaction method using Flavivirus universal primers," *American Journal of Tropical Medicine and Hygiene* (1998) 59(3): 357-362.

Flora, J. et al., "Dual-micro-ESI source for precise mass determination on a quadrupole time-of-flight mass spectrometer for genomic and proteomic applications," *Anal. Bioanal. Chem.* (2002) 373(7): 538-46.

Fox, A., "Report of the "Bioterrorism Workshop." Duke University Thomas Center on Apr. 2-4, 2002, organized by US Army Research Office," *J. Microbiol. Methods* (2002) 51(3): 247-54.

Fox, A. et al., "Identification and detection of bacteria: electrospray MS—MS versus derivatization/GC-MS," *Proceedings of the ERDEC Scientific Conference on Chemical and Biological Defense Research* (1996) Aberdeen Proving Ground, Md., Nov. 15-18, 1994: p. 39-44.

Fox, K. F. et al., "Identification of Brucella by Ribosomal-spacer-region PCR and differentiation of, *Brucella canis* from other *Brucella* spp. pathogenic for humans by carbohydrate profiles," *J. Clin. Microbiol.* (1998) 36(11): 3217-3222.

Griffey, R. H. et al., "Detection of base pair mismatches in duplex DNA and RNA oligonucleotides using electrospray mass spectrometry," *Proceedings of SPIE-The International Society for Optical Engineering* (1997) 2985(Ultrasensitive Biochemical Diagnostics II): 82-86.

Griffin, T. J. et al., "Direct genetic analysis by matrix-assisted laser desorption/ionization mass spectrometry," *Proc. Natl. Acad. Sci. USA* (1999) 96(11): 6301-6306.

Hannis, J. C. et al., "Accurate characterization of the tyrosine hydroxylase forensic allele 9.3 through development of electrospray ionization Fourier transform ion cyclotron resonance mass spectrometry," *Rapid Communications in Mass Spectrometry* (1999) 13(10): 954-62.

Hannis, J. C, et al., "Genotyping short tandem repeats using flow injection and electrospray ionization Fourier transform ion cyclotron resonance mass spectrometry," *Rapid Communications in Mass Spectrometry* (2001) 15(5): 348-350.

Hannis, J. C. et al., "Detection of double-stranded PCR amplicons at the attomole level electrosprayed from low nanomolar solutions using FT-ICR mass spectrometry," *Fresenius Journal of Analytical Chemistry* (2001) 369(3-4): 246-51.

Hannis, J. C. et al., "Genotyping complex short tanden repeats using electrospray ionization Fourier transform ion cyclotron resonance multistage mass spectrometry," *Proceedings of SPIE-The International Society for Optical Engineering* (2000) 3926: 36-47.

Hayashi, H. et al., "Phylogenetic analysis of the human gut microbiota using 16S rDNA clone libraries and strictly anaerobic culture-based methods," *Microbiol. Immunol.* (2002) 46(8): 535-48.

Henchal, E. A. et al., "Sensitivity and specificity of a universal primer set for the rapid diagnosis of dengue virus infections by polymerase chain reaction and nucleic acid hybridization," *American Journal of Tropical Medicine and Hygiene* (1991) 45(4): 418-28.

Herrmann, B. et al., "Differentiation of *Chlamydia* spp. by Sequence Determination and Restriction Endonuclease Cleavage of RNase P RNA Genes," *J. Clin. Microbiol.* (1996) 34(8): 1897-1902.

Higgins, G. S. et al., "Competitive oligonucleotide single-base extension combined with mass spectrometric detection for mutation screening," *BioTechniques* (1997) 23(4): 710-714.

Hoffmann, E. et al., "Universal primer set for the full-length amplification of all influenza A viruses," *Archives of Virology* (2001) 146(12): 2275-2289.

Honda, K. et al., "Universal method of hypersensitive nested PCR toward forensic DNA typing," *International Congress Series* (1998) 7: 28-30.

Hurst, G. B. et al., "Detection of Bacterial DNA Polymerase Chain Reation Products by Matrix-assisted Laser Desorption/Ionization Mass Spectrometry," *Rapid Commun. Mass Spectrom.* (1996) 10: 377-382.

Hurst, G. B. et al., "MALDI-TOF analysis of polymerase chain reaction products from methanotropic bacteria," *Anal. Chem*, (1998) 70(13): 2693-2698.

Isola, N. R. et al., "MALDI-TOF mass spectrometric method for detection of hybridized DNA oligomers," *Analytical Chemistry* (2001) 73(9): 2126-2131.

Jankowski, K. et al., "Mass spectrometry of DNA. Part 2. Quantitative estimation of base composition," *European Journal of Mass Spectrometry in Biochemistry* (1980) 1(1): 45-52.
Kageyama, A. et al., "Rapid detection of human fecal Eubacterium species and related genera by nested PCR method," *Microbiology and Immunology* (2001) 45(4): 315-318.
Krahmer, M. T. et al., "Electrospray quadrupole mass spectrometry analysis of model oligonucleotides and polymerase chain reaction products: determination of base substitutions, nucleotide additions/deletions, and chemical modifications," *Anal. Chem.* (1999) 71(14): 2893-900.
Krahmer, M. T. et al., "MS for identification of single nucleotide polymorphisms and MS/MS for discrimination of isomeric PCR products," *Anal. Chem.* (2000) 72(17): 4033-4040.
Lacroix, J.-M. et al., "PCR-based technique for the detection of bacteria in semen and urine," *J. Microbiol. Methods* (1996) 26: 61-71.
Leif, H. et al., "Isolation and characterization of the proton-translocating NADH: ubiquinone oxidoreductase from *Escherichia coli*," *Eur. J. Biochem.* (1995) 230(2): 538-548.
Li, J. et al., "Single nucleotide polymorphism determination using primer extension and time-of-flight mass spectrometry," *Electrophoresis* (1999) 20(6): 1258-1265.
Little, D. P. et al., "Rapid Sequencing of Oligonucleotides by High-Resolution Mass Spectrometry," *J. Am. Chem. Soc.* (1994) 116(11): 4893-4897.
Liu, C. et al., "Improving the microdialysis procedure for electrospray ionization mass spectrometry of biological samples," *Journal of Mass Spectrometry* (1997) 32(4): 425-431.
Liu, Y. et al., "An unusual gene arrangement for the putative chromosome replication origin and circadin expression of dnaN in *Synechococcus* sp. strain PCC 7942," *Gene* (1996) 172(1): 105-109.
Loakes, D. et al., "Nitroindoles as Universal Bases," *Nucleosides Nucleotides* (1995) 14:1001-1003.
Love, B. C. et al., "Cloning and sequence of the groESL heat-shock operon of *Pasteurella multocida,*" *Gene* (1995) 166(1): 179-180.
Maiwald, M. et al., "Characterization of contaminating DNA in Taq polymerase which occurs during amplification with a primer set for Legionella 5S ribosomal RNA," *Mol. Cell. Probes* (1994) 8(1): 11-14.
Mangrum, J. et al., "Solution composition and thermal denaturation for the production of single-stranded PCR amplicons: piperidine-induced destabilization of the DNA duplex?" *J. Am. Soc. Mass Spectrom.* (2002) 13(3): 232-40.
Martemyanov, K. A. et al., "Extremely Thermostable Elongation Factor G from *Aquifex aeolicus*: Cloning, Expression, Purification, and Characterization in a Heterologous Translation System," *Protein Expr. Purif.* (2000) 18(3): 257-261.
McCabe, K. M. et al., "Bacterial Species Identification after DNA Amplification with a Universal Primer Pair," *Molecular Genetics and Metabolism* (1999) 66(3): 205-211.
Meiyu, F. et al., "Detection of flaviviruses by reverse transcriptase-polymerase chain reaction with the universal primer set," *Microbiology and Immunology* (1997) 41(3): 209-13.
Messmer, T. O. et al., "Discrimination of *Streptococcus pneumoniae* from other upper respiratory tract streptococci by arbitrarily primed PCR," *Clin. Biochem.* (1995) 28(6):567-72.
Moricca, S. et al., "Detection of *Fusarium oxysporum* f.sp. vasinfectum in cotton tissue by polymerase chain reaction," *Plant Pathology* (1998) 47(4):486-494.
Morse, R. et al., "Nucleotide Sequence of Part of the ropC Gene Encoding the β' Subunit of DNA-Dependent RNA Polymerase from some Gram-Positive Bacteria and Comparative Amino Acid Sequence Analysis," *System Appl. Microbiol.* (1996) 19: 150-157.
Muddiman, D. C. et al., "Length and base composition of PCR-amplified nucleic acids using mass measurements from electrospray ionization mass spectrometry," *Anal. Chem.* (1997) 69(8): 1543-1549.
Muddiman, D. C. et al., "Application of secondary ion and matrix-assisted laser desorption-ionization time-of-flight mass spectrometry for the quantitative analysis of biological molecules," *Mass Spectrometry Reviews* (1996) 14(6): 383-429.
Muddiman, D. C. et al., "Important aspects concerning the quantification of biomolecules by time-of-flight secondary-ion mass spectrometry," *Applied Spectroscopy* (1996) 50(2): 161-166.
Muddiman, D. C. et al., "Precise mass measurement of a double-stranded 500 base-pair (309 kDa) polymerase chain reaction product by negative ion electrospray ionization Fourier transform ion cyclotron resonance mass spectrometry," *Rapid Commun. Mass Spectrom.* (1999) 13(12): 1201-1204.
Muddiman, D. C. et al., "Sequencing and characterization of larger oligonucleotides by electrospray ionization Fourier transform ion cyclotron resonance mass spectrometry," *Rev. Anal. Chem.* (1998) 17(1): p. 1-68.
Muddiman, D. C. et al., "Characterization of PCR products from bacilli using electrospray ionization FTICR mass spectrometry," *Analytical Chemistry* (1996) 68(21): 3705-12.
Muhammad, W. T. et al., "Electrospray ionization quadrupole time-of-flight mass spectrometry and quadrupole mass spectrometry for genotyping single nucleotide substitutions in intact polymerase chain reaction products in K-ras and p53," *Rapid Commun. Mass Spectrom.* (2002) 16(24): 2278-85.
Mushegian, A. R. et al., "A minimal gene set for cellular life derived by comparison of complete bacterial genomes," *Proc. Natl. Acad. Sci. USA* (1996) 93(19): 10268-10273.
Nagpal, M. L. et al., "Utility of 16S-23S rNA spacer region methodology: how similar are interspace regions within a genome and between strains for closely related organisms?" *J. Microbiol. Methods* (1998) 33(s): 211-219.
Naumov, G. I. et al., "Discrimination between the soil yeast species *Williopsis saturnus* and *Williopsis suaveolens* by the polymerase chain reaction with the universal primer N21," *Microbiology* (Moscow)(Translation of Mikrobiologiya) (2000) 69(2): 229-233.
Null, A. P. et al., "Evaluation of sample preparation techniques for mass measurements of PCR products using ESI-FT-ICR mass spectrometry," *J. Am. Soc. Mass Spectrom.* (2002) 13(4): 338-344.
Null, A. P. et al., "Preparation of single-stranded PCR products for electrospray ionization mass spectrometry using the DNA repair enzyme lambda exonuclease," *Analyst* (2000) 125(4): 619-626.
Null, A. P. et al., "Genotyping of Simple and Compound Short Tandem Repeat Loci Using Electrospray Ionization Fourier Transform Ion Cyclotron Resonance Mass Spectrometry," *Anal. Chem.* (2001) 73(18): 4514-4521.
Null, A. P. et al., "Perspectives on the use of electrospray ionization Fourier transform ion cyclotron resonance mass spectrometry for short tandem repeat genotyping in the post-genome era," *Journal of Mass Spectrometry* (2001) 36(6): 589-606.
Peng, X. et al., "Rapid detection of Shigella species in environmental sewage by an immunocapture PCR with universal primers," *Appl. Environ. Microbiol.* (2002) 68(5): 2580-3.
Pomerantz, S. C. et al., "Determination of oligonucleotide composition from mass spectrometrically measured molecular weight," *J. Am. Soc. Mass Spectrom.* (1993) 4(3): 204-9.
Reid, S. M. et al., "Primary diagnosis of foot-and-mouth disease by reverse transcription polymerase chain reaction," *Journal of Virological Methods* (2000) 89(1-2): 167-76.
Reilly, K. et al., "Design and use of 16S ribosomal DNA-directed primers in competitive PCRs to enumerate proteolytic bacteria in the rumen," *Microbiol. Ecol.* (2002) 43(2): 259-70.
Ross, P. L. et al., "Analysis of DNA fragments from conventional and microfabricated PCR devices using delayed extraction MALDI-TOF mass spectrometry," *Anal. Chem.* (1998) 70(10): 2067-73.
Ross, P. L. et al., "Discrimination of Single-Nucleotide Polymorphisms in Human DNA Using Peptide Nucleic Acid Probes Detected by MALDI-TOF Mass Spectrometry," *Anal. Chem.* (1997) 69(20): 4197-4202.
Sala, M. et al., "Ambiguous base pairing of the purine analogue 1-(2-deoxy-beta-D-ribofuranosyl)-imidazole-4-carboxamide during PCR," *Nucleic Acids Res.* (1996) 24(17): 3302-6.
Schram, K. H., "Mass Spectrometry of Nucleic Acid Components," *Biomedical Applications of Mass Spectrometry* (1990) 34: 203-280.
Schultz, J. C. et al., "Polymerase chain reaction products analyzed by charge detection mass spectrometry," *Rapid Communications in Mass Spectrometry* (1999) 13(1): 15-20.

Seshadri, R. et al., "Differential Expression of Translational Elements by Life Cycle Variants of *Coxiella burnetii,*" *Infect. Immun.* (1999) 67(11): 6026-6033.

Shaver, Y. J. et al., "Variation in 16S-23S rRNA intergenic spacer regions among *Bacillus subtilis* 168 isolates," *Molecular Microbiology* (2001) 42(1): 101-109.

Shaver, Y. J. et al., "Restriction fragment length polymorphism of rRNA operons for discrimination and intergenic spacer sequences for cataloging of *Bacillus subtilis* sub-groups," *J. Microbiol., Methods* (2002) 50(2): 215-23.

Srinivasan, J. R. et al., "Matrix-assisted laser desorption/ionization time-of-flight mass spectrometry as a rapid screening method to detect mutations causing Tay-Sachs disease," *Rapid Communications in Mass Spectrometry* (1997) 11(10): 1144-1150.

Steffens, D. L. et al., "Sequence analysis of mitochondrial DNA hypervariable regions using infrared fluorescence detection," *BioTechniques* (1998) 24(6): 1044-1046.

Takahashi, H. et al., "Characterization of gyrA, gyrB, grlA and grlB mutations in fluoroquinolone-resistant clinical isolates of *Staphylococcus aureus*," *J. Antimicrob. Chemother*. (1998) 41(1): 49-57.

Tong, J. et al., "Ligation reaction specificities of and $NAD^+$-dependent DNA ligase from the hyperthermophile *Aquifex aeolicus,*" *Nucleic Acids Res*. (2000) 28(6): 1447-1454.

Van Aerschot, A. et al., "In search of acyclic analogues as universal nucleosides in degenerate probes," *Nucleosides & Nucleotides* (1995) 14(3-5): 1053-1056.

Van Baar, B. L., "Characterisation of bacteria by matrix-assisted laser desorption/ionisation and electrospray mass spectrometry," *FEMS Microbiol. Rev*. (2000).24(2): 193-219.

Van Camp, G. et al., "Amplification and sequencing of variable regions in bacterial 23S ribosomal RNA genes with conserved primer sequences," *Curr. Microbiol*. (1993) 27(3): 147-51.

Walters, J. J. et al., "Genotyping single nucleotide polymorphisms using intact polymerase chain reaction products by electrospray quadrupole mass spectrometry," *Rapid Commun. Mass Spectrom*. (2001) 15(18): 1752-1759.

Widjojoatmodjo, M. N. et al., "Rapid identification of bacteria by PCR-single-strand conformation polymorphism," *J. Clin. Microbiol*. (1994) 32(12): 3002-3007.

Wolter, A. et al., "Negative Ion FAB Mass Spectrometric Analysis of Non-Charged Key Intermediates in Oligonucleotide Synthesis: Rapid Identification of Partially Protected Dinucleoside Monophosphates," *Biomed. Environ. Mass Spectrom*. (1987) 14: 111-116.

Woo, T. H. S. et al., "Identification of *Leptospira inadai* by continuous monitoring of fluorescence during rapid cycle PCR," *Systematic and Applied Microbiology* (1998) 21(1): 89-96.

Wunschel, D. et al., "Discrimination among the *B. cereus* group, in comparison to *B. subtilis*, by structural carbohydrate profiles and ribosomal RNA spacer region PCR," *Systematic and Applied Microbiology* (1995) 17(4): 625-35.

Wunschel, D. S. et al., "Analysis of double-stranded polymerase chain reaction products from the *Bacillus cereus* group by electrospray ionization Fourier transform ion cyclotron resonance mass spectrometry," *Rapid Communications in Mass Spectrometry* (1996) 10(1): 29-35.

Wunschel, D. S. et al., "Heterogeneity in *Bacillus cereus* PCR products detected by ESI-FTICR mass spectrometry," *Analytical Chemistry* (1998) 70(6): 1203-1207.

Wunschel, D. S. et al., "Mass spectrometric characterization of DNA for molecular biological applications: Advances using MALDI and ESI," *Advances in Mass Spectrometry* (1998) 14: 377-406.

Yasui, T. et al., "A specific oligonucleotide primer for the rapid detection of *Lactobacillus linderi* by polymerase chain reaction," *Can. J. Microbiol*. (1997) 43(2): 157-163.

* cited by examiner

*B. anthracis* ($A_{14}G_9C_{14}T_9$) $MW_{meas}$ = 14072.2)

*B. anthracis*\* ($A_1A^*_{13}G_9C_{14}T_9$) $MW_{meas}$ = 14280.9)

13500　　　14000　　　14500
MW

METHOD FOR RAPID DETECTION AND IDENTIFICATION OF BIOAGENTS

CROSS-REFERENCE TO RELATED APPLICATIONS

The present application is a divisional of U.S. Ser. No. 09/798,007 filed Mar. 2, 2001, now abandoned which is incorporated herein by reference in its entirety.

STATEMENT OF GOVERNMENT SUPPORT

This invention was made with United States Government support under DARPA/SPO contract BAA00-09. The United States Government may have certain rights in the invention.

FIELD OF THE INVENTION

The present invention relates to methods for rapid detection and identification of bioagents from environmental, clinical or other samples. The methods provide for detection and characterization of a unique base composition signature (BCS) from any bioagent, including bacteria and viruses. The unique BCS is used to rapidly identify the bioagent.

BACKGROUND OF THE INVENTION

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure which amplifies a specific target DNA sequence based on the flanking primers used. Finally, detection and data analysis convert the hybridization event into an analytical result.

Other techniques for detection of bioagents include high-resolution mass spectrometry (MS), low-resolution MS, fluorescence, radioiodination, DNA chips and antibody techniques. None of these techniques is entirely satisfactory.

Mass spectrometry provides detailed information about the molecules being analyzed, including high mass accuracy. It is also a process that can be easily automated. However, high-resolution MS alone fails to perform against unknown or bioengineered agents, or in environments where there is a high background level of bioagents ("cluttered" background). Low-resolution MS can fail to detect some known agents, if their spectral lines are sufficiently weak or sufficiently close to those from other living organisms in the sample. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.* 7:1266–1269, 1996; Muddiman et al., *Anal. Chem.* 69:1543–1549, 1997; Wunschel et al., *Anal. Chem.* 70:1203–1207, 1998; Muddiman et al., *Rev. Anal. Chem.* 17:1–68, 1998). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 10:377–382, 1996). The use of matrix-assisted laser desorption ionization-time of flight (MALDI-TOF) mass spectrometry for characterization of PCR products has been described. (Muddiman et al., *Rapid Commun. Mass Spec.* 13:1201–1204, 1999). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by nonrandomly fragmenting the target into a set of single-stranded nonrandom length fragments and determining their masses by MS.

U.S. Pat. No. 5,605,798 describes a fast and highly accurate mass spectrometer-based process for detecting the presence of a particular nucleic acid in a biological sample for diagnostic purposes.

WO 98/21066 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 describe methods of sequencing nucleic acids using mass spectrometry. U.S. Pat. Nos. 5,622,824, 5,872,003 and 5,691,141 describe methods, systems and kits for exonuclease-mediated mass spectrometric sequencing.

Thus, there is a need for a method for bioagent detection and identification which is both specific and rapid, and in which no nucleic acid sequencing is required. The present invention addresses this need.

SUMMARY OF THE INVENTION

One embodiment of the present invention is a method of identifying an unknown bioagent comprising (a) contacting nucleic acid from the bioagent with at least one pair of oligonucleotide primers which hybridize to sequences of the nucleic acid and flank a variable nucleic acid sequence; (b) amplifying the variable nucleic acid sequence to produce an amplification product; (c) determining the molecular mass of the amplification product; and (d) comparing the molecular mass to one or more molecular masses of amplification products obtained by performing steps (a)–(c) on a plurality of known organisms, wherein a match identifies the unknown bioagent. In one aspect of this preferred embodiment, the sequences to which the at least one pair of oligonucleotide primers hybridize are highly conserved. Preferably, the amplifying step comprises polymerase chain reaction. Alternatively, the amplifying step comprises ligase chain reaction or strand displacement amplification. In one aspect of this preferred embodiment, the bioagent is a bacterium, virus, cell or spore. Advantageously, the nucleic acid is ribosomal RNA. In another aspect, the nucleic acid encodes RNase P or an RNA-dependent RNA polymerase. Preferably, the amplification product is ionized prior to molecular mass determination. The method may further comprise the step of isolating nucleic acid from the bioagent prior to contacting the nucleic acid with the at least one pair of oligonucleotide primers. The method may further comprise the step of performing steps (a)–(d) using a different oligonucleotide primer pair and comparing the results to one or more molecular mass amplification products obtained by performing steps (a)–(c) on a different plurality of known organisms from those in step (d). Preferably, the one or more molecular mass is contained in a database of molecular masses. In another aspect of this preferred embodiment, the amplification product is ionized by electrospray ionization, matrix-assisted laser desorption or fast atom bombardment. Advantageously, the molecular mass is determined by mass spectrometry. Preferably, the mass spectrometry is Fourier transform ion cyclotron resonance mass spectrometry (FT-ICR-MS), ion trap, quadrupole, magnetic sector, time of flight (TOF), Q-TOF or triple quadrupole. The method may further comprise performing step (b) in the presence of an analog of adenine, thymidine, guanosine or cytidine having a different molecular weight than adenosine, thymidine, guanosine or cytidine. In one aspect, the oligonucleotide primer comprises a base analog or substitute base at positions 1 and 2 of each triplet within the primer, wherein the base analog or substitute base binds with increased affinity to its complement compared to the native base. Preferably, the primer comprises a universal base at position 3 of each triplet within the primer. The base analog or substitute base may be 2,6-diaminopurine, propyne T, propyne G, phenoxazines or G-clamp. Preferably, the universal base is inosine, guanidine, uridine, 5-nitroindole, 3-nitropyrrole, dP or dK, or 1-(2-deoxy-β-D-ribofuranosyl)-imidazole-4-carboxamide.

Another embodiment of the present invention is a method of identifying an unknown bioagent comprising (a) contacting nucleic acid from the bioagent with at least one pair of oligonucleotide primers which hybridize to sequences of the nucleic acid and flank a variable nucleic acid sequence; (b) amplifying the variable nucleic acid sequence to produce an amplification product; (c) determining the base composition of the amplification product; and (d) comparing the base composition to one or more base compositions of amplification products obtained by performing steps (a)–(c) on a plurality of known organisms, wherein a match identifies the unknown bioagent. In one aspect of this preferred embodiment, the sequences to which the at least one pair of oligonucleotide primers hybridize are highly conserved. Preferably, the amplifying step comprises polymerase chain reaction. Alternatively, the amplifying step comprises ligase chain reaction or strand displacement amplification. In one aspect of this preferred embodiment, the bioagent is a bacterium, virus, cell or spore. Advantageously, the nucleic acid is ribosomal RNA. In another aspect, the nucleic acid encodes RNase P or an RNA-dependent RNA polymerase. Preferably, the amplification product is ionized prior to molecular mass determination. The method may further comprise the step of isolating nucleic acid from the bioagent prior to contacting the nucleic acid with the at least one pair of oligonucleotide primers. The method may further comprise the step of performing steps (a)–(d) using a different oligonucleotide primer pair and comparing the results to one or more base composition signatures of amplification products obtained by performing steps (a)–(c) on a different plurality of known organisms from those in step (d). Preferably, the one or more base compositions is contained in a database of base compositions. In another aspect of this preferred embodiment, the amplification product is ionized by electrospray ionization, matrix-assisted laser desorption or fast atom bombardment. Advantageously, the molecular mass is determined by mass spectrometry. Preferably, the mass spectrometry is Fourier transform ion cyclotron resonance mass spectrometry (FT-ICR-MS), ion trap, quadrupole, magnetic sector, time of flight (TOF), Q-TOF or triple quadrupole. The method may further comprise performing step (b) in the presence of an analog of adenine, thymidine, guanosine or cytidine having a different molecular weight than adenosine, thymidine, guanosine or cytidine. In one aspect, the oligonucleotide primer comprises a base analog or substitute base at positions 1 and 2 of each triplet within the primer, wherein the base analog or substitute base binds with increased affinity to its complement compared to the native base. Preferably, the primer comprises a universal base at position 3 of each triplet within the primer. The base analog or substitute base may be 2,6-diaminopurine, propyne T, propyne G, phenoxazines or G-clamp. Preferably, the universal base is inosine, guanidine, uridine, 5-nitroindole, 3-nitropyrrole, dP or dK, or 1-(2-deoxy-β-D-ribofuranosyl)-imidazole-4-carboxamide.

The present invention also provides a method for detecting a single nucleotide polymorphism in an individual, comprising the steps of (a) isolating nucleic acid from the individual; (b) contacting the nucleic acid with oligonucleotide primers which hybridize to regions of the nucleic acid which flank a region comprising the potential polymorphism; (c) amplifying the region to produce an amplification product; (d) determining the molecular mass of the amplification product; and (e) comparing the molecular mass to the molecular mass of the region in an individual known to have the polymorphism, wherein if the molecular masses are the same then the individual has the polymorphism.

In one aspect of this preferred embodiment, the primers hybridize to highly conserved sequences. Preferably, the polymorphism is associated with a disease. Alternatively, the polymorphism is a blood group antigen. In one aspect of the preferred embodiment, the amplifying step is polymerase chain reaction. Alternatively, the amplification step is ligase chain reaction or strand displacement amplification. Preferably, the amplification product is ionized prior to mass determination. In one aspect, the amplification product is ionized by electrospray ionization, matrix-assisted laser desorption or fast atom bombardment. Advantageously, the molecular mass is determined by mass spectrometry. Preferably, the mass spectrometry is Fourier transform ion cyclotron resonance mass spectrometry (FT-ICR-MS), ion trap, quadrupole, magnetic sector, time of flight (TOF), Q-TOF or triple quadrupole.

BRIEF DESCRIPTION OF THE DRAWINGS

FIG. 2 shows a typical primer amplified region from the 16S rRNA Domain III shown in FIG. 1A-1.

DETAILED DESCRIPTION OF THE INVENTION

Figures 1, 1A:
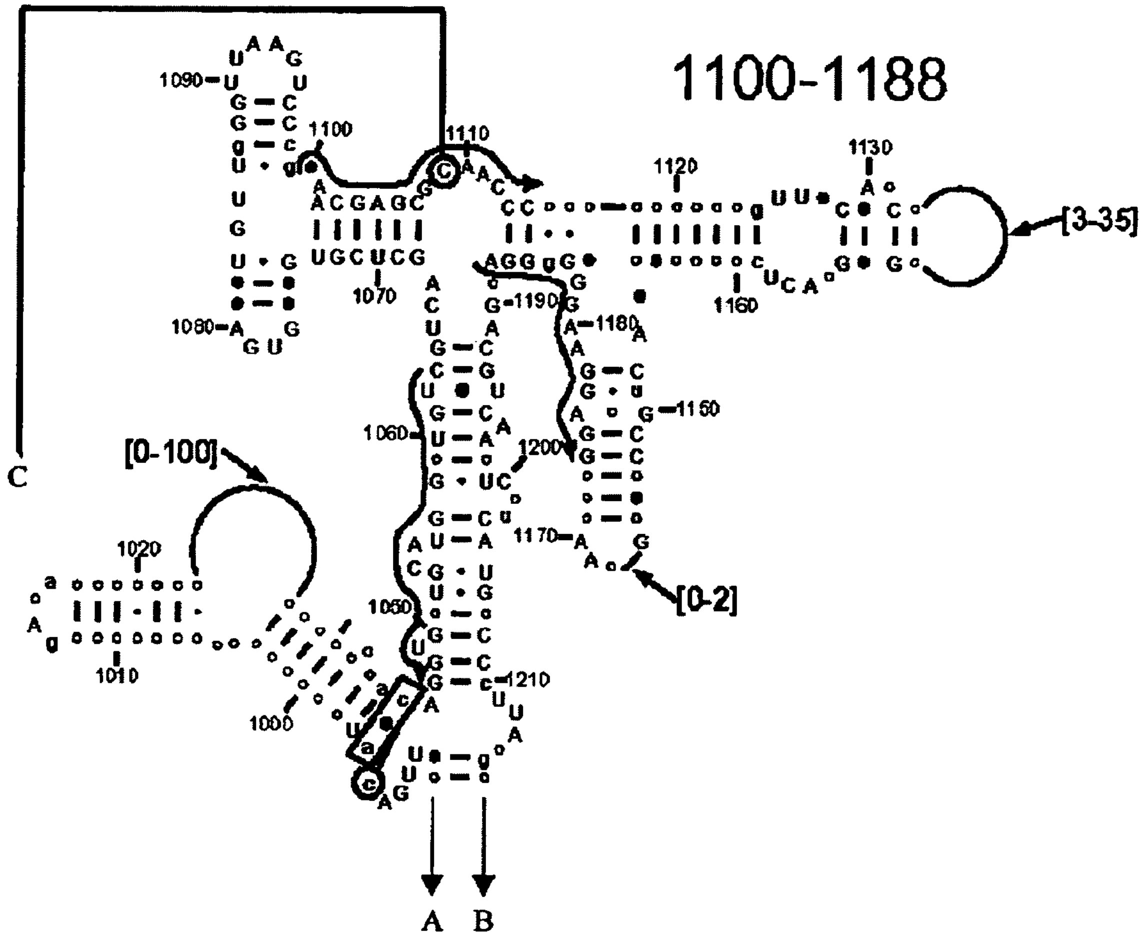
FIGS. 1A–1H and FIG. 2 are consensus diagrams that show examples of conserved regions from 16S rRNA (FIG. 1A-1, 1A-2, 1A-3, 1A-4, and 1A-5), 23S rRNA (3'-half, FIG. 1B, 1C, and 1D, 5'-half, FIG. 1E–F), 23S rRNA Domain I (FIG. 1G), 23S rRNA Domain IV (FIG. 1H) and 16S rRNA Domain III (FIG. 2) which are suitable for use in the present invention. Where there is overlap or redundancy between the figures, the overlap is simply provided as an orientation aid and no additional members of the sequence are implied thereby. Lines with arrows are examples of regions to which intelligent primer pairs for PCR are designed. The label for each primer pair represents the starting and ending base number of the amplified region on the consensus diagram. Bases in capital letters are greater than 95% conserved; bases in lower case letters are 90–95% conserved, filled circles are 80–90% conserved; and open circles are less than 80% conserved. The label for each primer pair represents the starting and ending base number of the amplified region on the consensus diagram. The nucleotide sequence of the 16S rRNA consensus sequence is SEQ ID NO:3 and the nucleotide sequence of the 23S rRNA consensus sequence is SEQ ID NO:4.

The present invention provides a combination of a non-PCR biomass detection mode, preferably high-resolution MS, with PCR-based BCS technology using "intelligent primers" which hybridize to conserved sequence regions of nucleic acids derived from a bioagent and which bracket variable sequence regions that uniquely identify the bioagent. The high-resolution MS technique is used to determine the molecular mass and base composition signature (BCS) of the amplified sequence region. This unique "base composition signature" (BCS) is then input to a maximum-likelihood detection algorithm for matching against a database of base composition signatures in the same amplified region. The present method combines PCR-based amplification technology (which provides specificity) and a molecular mass detection mode (which provides speed and does not require nucleic acid sequencing of the amplified target sequence) for bioagent detection and identification.

The present method allows extremely rapid and accurate detection and identification of bioagents compared to existing methods. Furthermore, this rapid detection and identification is possible even when sample material is impure. Thus, the method is useful in a wide variety of fields, including, but not limited to, environmental testing (e.g., detection and discrimination of pathogenic vs. non-pathogenic bacteria in water or other samples), germ warfare (allowing immediate identification of the bioagent and appropriate treatment), pharmacogenetic analysis and medical diagnosis (including cancer diagnosis based on mutations and polymorphisms; drug resistance and susceptibility testing; screening for and/or diagnosis of genetic diseases and conditions; and diagnosis of infectious diseases and conditions). The method leverages ongoing biomedical research in virulence, pathogenicity, drug resistance and genome sequencing into a method which provides greatly improved sensitivity, specificity and reliability compared to existing methods, with lower rates of false positives.

The present method can be used to detect and classify any biological agent, including bacteria, viruses, fungi and toxins. As one example, where the agent is a biological threat, the information obtained is used to determine practical information needed for countermeasures, including toxin genes, pathogenicity islands and antibiotic resistance genes. In addition, the methods can be used to identify natural or deliberate engineering events including chromosome fragment swapping, molecular breeding (gene shuffling) and emerging infectious diseases.

Bacteria have a common set of absolutely required genes. About 250 genes are present in all bacterial species (*Proc. Natl. Acad. Sci. U.S.A.* 93:10268, 1996; *Science* 270:397, 1995), including tiny genomes like *Mycoplasma, Ureaplasma* and *Rickettsia*. These genes encode proteins involved in translation, replication, recombination and repair, transcription, nucleotide metabolism, amino acid metabolism, lipid metabolism, energy generation, uptake, secretion and the like. Examples of these proteins are DNA polymerase III beta, elongation factor TU, heat shock protein groEL, RNA polymerase beta, phosphoglycerate kinase, NADH dehydrogenase, DNA ligase, DNA topoisomerase and elongation factor G. Operons can also be targeted using the present method. One example of an operon is the bfp operon from enteropathogenic *E. coli*. Multiple core chromosomal genes can be used to classify bacteria at a genus or genus species level to determine if an organism has threat potential. The method can also be used to detect pathogenicity markers (plasmid or chromosomal) and antibiotic resistance genes to confirm the threat potential of an organism and to direct countermeasures.

A theoretically ideal bioagent detector would identify, quantify, and report the complete nucleic acid sequence of every bioagent that reached the sensor. The complete sequence of the nucleic acid component of a pathogen would provide all relevant information about the threat, including its identity and the presence of drug-resistance or pathogenicity markers. This ideal has not yet been achieved. However, the present invention provides a straightforward strategy for obtaining information with the same practical value using base composition signatures (BCS). While the base composition of a gene fragment is not as information-rich as the sequence itself, there is no need to analyze the complete sequence of the gene if the short analyte sequence fragment is properly chosen. A database of reference sequences can be prepared in which each sequence is indexed to a unique base composition signature, so that the presence of the sequence can be inferred with accuracy from the presence of the signature. The advantage of base composition signatures is that they can be quantitatively measured in a massively parallel fashion using multiplex PCR (PCR in which two or more primer pairs amplify target sequences simultaneously) and mass spectrometry. These multiple primer amplified regions uniquely identify most threat and ubiquitous background bacteria and viruses. In addition, cluster-specific primer pairs distinguish important local clusters (e.g., *anthracis* group).

In the context of this invention, a "bioagent" is any organism, living or dead, or a nucleic acid derived from such an organism. Examples of bioagents include but are not limited to cells (including but not limited to human clinical samples, bacterial cells and other pathogens) viruses, toxin genes and bioregulating compounds). Samples may be alive or dead or in a vegetative state (for example, vegetative bacteria or spores) and may be encapsulated or bioengineered.

As used herein, a "base composition signature" (BCS) is the exact base composition from selected fragments of nucleic acid sequences that uniquely identifies the target gene and source organism. BCS can be thought of as unique indexes of specific genes.

Figures 1, 1A, 2:
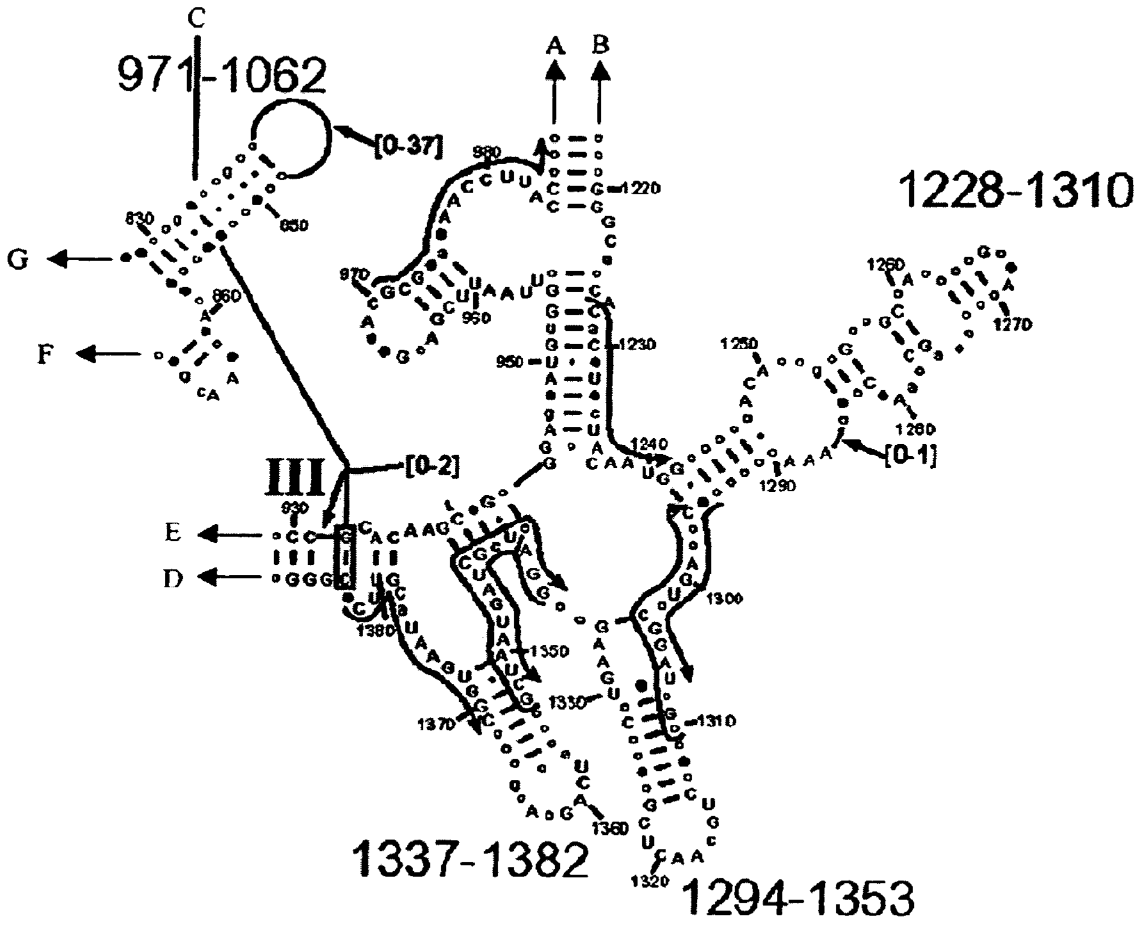

As used herein, "intelligent primers" are primers which bind to sequence regions which flank an intervening variable region. In a preferred embodiment, these sequence regions which flank the variable region are highly conserved among different species of bioagent. For example, the sequence regions may be highly conserved among all *Bacillus* species. By the term "highly conserved", it is meant that the sequence regions exhibit between about 80–100%, more preferably between about 90–100% and most preferably between about 95–100% identity. Examples of intelligent primers which amplify regions of the 16S and 23S rRNA are shown in FIGS. 1A–1H. A typical primer amplified region in 16S rRNA is shown in FIG. 2. The arrows represent primers which bind to highly conserved regions which flank a variable region in 16S rRNA domain III. The amplified region is the stem-loop structure under "1100–1188."

One main advantage of the detection methods of the present invention is that the primers need not be specific for a particular bacterial species, or even genus, such as *Bacillus* or *Streptomyces*. Instead, the primers recognize highly conserved regions across hundreds of bacterial species including, but not limited to, the species described herein. Thus, the same primer pair can be used to identify any desired bacterium because it will bind to the conserved regions which flank a variable region specific to a single species, or common to several bacterial species, allowing nucleic acid amplification of the intervening sequence and determination of its molecular weight and base composition. For example, the 16S_971–1062, 16S_1228–1310 and 16S_1100–1188 regions are 98–99% conserved in about 900 species of bacteria (16S=16S rRNA, numbers indicate nucleotide position). In one embodiment of the present invention, primers used in the present method bind to one or more of these regions or portions thereof.

The present invention provides a combination of a non-PCR biomass detection mode, preferably high-resolution MS, with nucleic acid amplification-based BCS technology using "intelligent primers" which hybridize to conserved regions and which bracket variable regions that uniquely identify the bioagent(s). Although the use of PCR is preferred, other nucleic acid amplification techniques may also be used, including ligase chain reaction (LCR) and strand displacement amplification (SDA). The high-resolution MS technique allows separation of bioagent spectral lines from background spectral lines in highly cluttered environments. The resolved spectral lines are then translated to BCS which are input to a maximum-likelihood detection algorithm matched against spectra for one or more known BCS. Preferably, the bioagent BCS spectrum is matched against one or more databases of BCS from vast numbers of bioagents. Preferably, the matching is done using a maximum-likelihood detection algorithm.

In a preferred embodiment, base composition signatures are quantitatively measured in a massively parallel fashion using the polymerase chain reaction (PCR), preferably multiplex PCR, and mass spectrometric (MS) methods. Sufficient quantities of nucleic acids must be present for detection of bioagents by MS. A wide variety of techniques for preparing large amounts of purified nucleic acids or fragments thereof are well known to those of skill in the art. PCR requires one or more pairs of oligonucleotide primers which bind to regions which flank the target sequence(s) to be amplified. These primers prime synthesis of a different strand of DNA, with synthesis occurring in the direction of one primer towards the other primer. The primers, DNA to be amplified, a thermostable DNA polymerase (e.g. Taq polymerase), the four deoxynucleotide triphosphates, and a buffer are combined to initiate DNA synthesis. The solution is denatured by heating, then cooled to allow annealing of newly added primer, followed by another round of DNA synthesis. This process is typically repeated for about 30 cycles, resulting in amplification of the target sequence.

The "intelligent primers" define the target sequence region to be amplified and analyzed. In one embodiment, the target sequence is a ribosomal RNA (rRNA) gene sequence. With the complete sequences of many of the smallest microbial genomes now available, it is possible to identify a set of genes that defines "minimal life" and identify composition signatures that uniquely identify each gene and organism. Genes that encode core life functions such as DNA replication, transcription, ribosome structure, translation, and transport are distributed broadly in the bacterial genome and are prefeffed regions for BCS analysis. Ribosomal RNA (rRNA) genes comprise regions that provide useful base composition signatures. Like many genes involved in core life functions, rRNA genes contain sequences that are extraordinarily conserved across bacterial domains interspersed with regions of high variability that are more specific to each species. The variable regions can be utilized to build a database of base composition signatures. The strategy involves creating a structure-based alignment of sequences of the small (16S) and the large (23S) subunits of the rRNA genes. For example, there are currently over 13,000 sequences in the ribosomal RNA database that has been created and maintained by Robin Gutell, University of Texas at Austin, and is publicly available on the Institute for Cellular and Molecular Biology web page (www.rna.icmb.utexas.edul). There is also a publicly available rRNA database created and maintained by the University of Antwerp, Belgium at www.rrna.uia.ac.be.

These databases have been analyzed to determine regions that are useful as base composition signatures. The characteristics of such regions are: a) between about 80 and 100%, preferably > about 95% identity among species of the particular bioagent of interest, of upstream and downstream nucleotide sequences which serve as sequence amplification primer sites; b) an intervening variable region which exhibits no greater than about 5% identity among species; and c) a separation of between about 30 and 1000 nucleotides, preferably no more than about 50–250 nucleotides, and more preferably no more than about 60–100 nucleotides, between the conserved regions.

Due to their overall conservation, the flanking rRNA primer sequences serve as good "universal" primer binding sites to amplify the region of interest for most, if not all, bacterial species. The intervening region between the sets of primers varies in length and/or composition, and thus provides a unique base composition signature.

It is advantageous to design the "intelligent primers" to be as universal as possible to minimize the number of primers which need to be synthesized, and to allow detection of multiple species using a single pair of primers. These primer pairs can be used to amplify variable regions in these species. Because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base". For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., *Nucleosides and Nucleotides* 14:1001–1003, 1995), the degenerate nucleotides dP or dK (Hill et al.), an acyclic nucleoside analog containing 5-nitroindazole (Van Aerschot et al., *Nucleosides and Nucleotides* 14:1053–1056, 1995) or the purine analog 1-(2-deoxy-β-D-ribofuranosyl)-imidazole-4-carboxamide (Sala et al., *Nucl. Acids Res.* 24:3302–3306, 1996).

In another embodiment of the invention, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs are 2,6-diaminopurine which binds to thymine, propyne T which binds to adenine and propyne C and phenoxazines, including G-clamp, which binds to G. Propynes are described in U.S. Pat. Nos. 5,645,985, 5,830,653 and 5,484,908, the entire contents of which are incorporated herein by reference. Phenoxazines are described in U.S. Pat. Nos. 5,502,177, 5,763,588, and 6,005,096, the entire contents of which are incorporated herein by reference. G-clamps are described in U.S. Pat. Nos. 6,007,992 and 6,028,183, the entire contents of which are incorporated herein by reference.

Bacterial biological warfare agents capable of being detected by the present methods include *Bacillus anthracis* (anthrax), *Yersinia pestis* (pneumonic plague), *Franciscella tularensis* (tularemia), *Brucella suis, Brucella abortus, Brucella melitensis* (undulant fever), *Burkholderia mallei* (glanders), *Burkholderia pseudomalleii* (melioidosis), *Salmonella typhi* (typhoid fever), *Rickettsia typhii* (epidemic typhus), *Rickettsia prowasekii* (endemic typhus) and *Coxiella burnetii* (Q fever), *Rhodobacter capsulatus, Chlamydia pneumoniae, Escherichia coli, Shigella dysenteriae, Shigella flexneri, Bacillus cereus, Clostridium botulinum, Coxiella burnetti, Pseudomonas aeruginosa, Legionella pneumophila*, and *Vibrio cholerae.*

Figures 1, 1A, 2, 3:
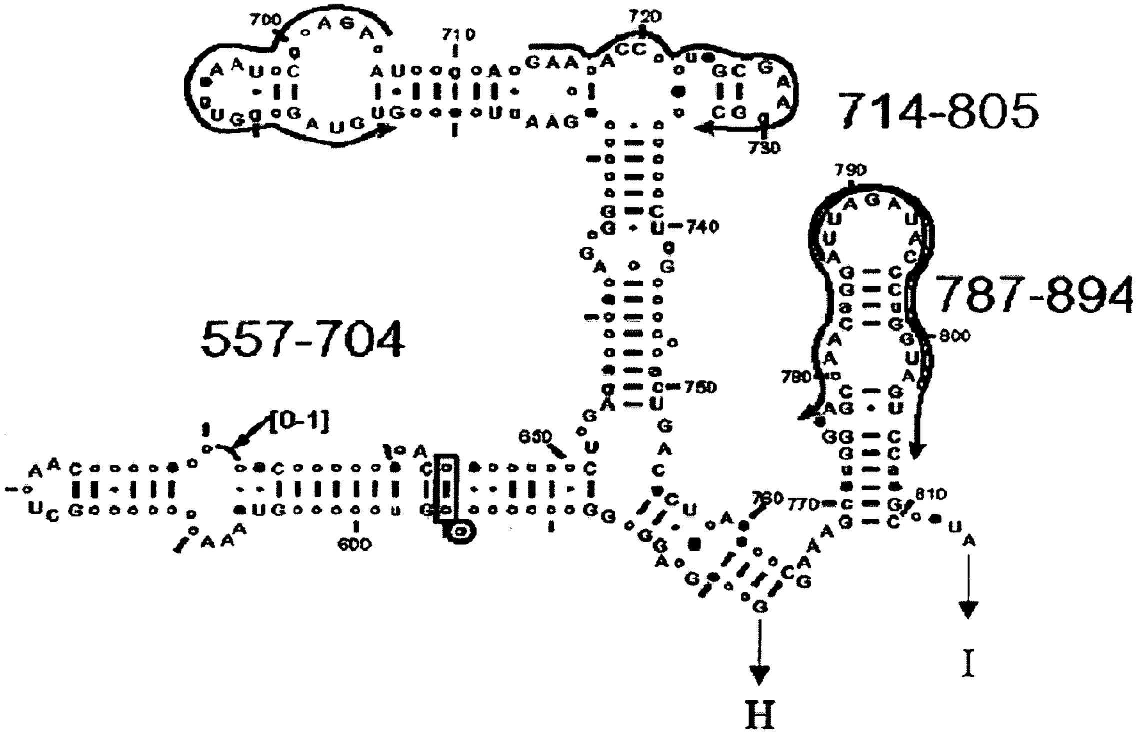
FIG. 3 is a schematic diagram showing conserved regions in RNase P. Bases in capital letters are greater than 90% conserved; bases in lower case letters are 80–90% conserved; filled circles designate bases which are 70–80% conserved; and open circles designate bases that are less than 70% conserved.

Besides 16S and 23S rRNA, other target regions suitable for use in the present invention for detection of bacteria include 5S rRNA and RNase P (FIG. 3).

Biological warfare fungus biowarfare agents include *coccidioides immitis* (Coccidioidomycosis).

Biological warfare toxin genes capable of being detected by the methods of the present invention include botulism, T-2 mycotoxins, ricin, staph enterotoxin B, shigatoxin, abrin, aflatoxin, *Clostridium perfringens* epsilon toxin, conotoxins, diacetoxyscirpenol, tetrodotoxin and saxitoxin.

Biological warfare viral threat agents are mostly RNA viruses (positive-strand and negative-strand), with the exception of smallpox. Every RNA virus is a family of related viruses (quasispecies). These viruses mutate rapidly and the potential for engineered strains (natural or deliberate) is very high. RNA viruses cluster into families that have conserved RNA structural domains on the viral genome (e.g., virion components, accessory proteins) and conserved housekeeping genes that encode core viral proteins including, for single strand positive strand RNA viruses, RNA-dependent RNA polymerase, double stranded RNA helicase, chymotrypsin-like and papain-like proteases and methyltransferases.

Examples of (−)-strand RNA viruses include arenaviruses (e.g., sabia virus, lassa fever, Machupo, Argentine hemorrhagic fever, flexal virus), bunyaviruses (e.g., hantavirus, nairovirus, phlebovirus, hantaan virus, Congo-crimean hemorrhagic fever, rift valley fever), and mononegavirales (e.g., filovirus, paramyxovirus, ebola virus, Marburg, equine morbillivirus).

Examples of (+)-strand RNA viruses include picornaviruses (e.g., coxsackievirus, echovirus, human coxsackievirus A, human echovirus, human enterovirus, human poliovirus, hepatitis A virus, human parechovirus, human rhinovirus), astroviruses (e.g., human astrovirus), calciviruses (e.g., chiba virus, chitta virus, human calcivirus, norwalk virus), nidovirales (e.g., human coronavirus, human torovirus), flaviviruses (e.g., dengue virus 1–4, Japanese encephalitis virus, Kyanasur forest disease virus, Murray Valley encephalitis virus, Rocio virus, St. Louis encephalitis virus, West Nile virus, yellow fever virus, hepatitis c virus) and togaviruses (e.g., Chikugunya virus, Eastern equine encephalitis virus, Mayaro virus, O'nyong-nyong virus, Ross River virus, Venezuelan equine encephalitis virus, Rubella virus, hepatitis E virus). The hepatitis C virus has a 5'-untranslated region of 340 nucleotides, an open reading frame encoding 9 proteins having 3010 amino acids and a 3'-untranslated region of 240 nucleotides. The 5'-UTR and 3'-UTR are 99% conserved in hepatitis C viruses.

In one embodiment, the target gene is an RNA-dependent RNA polymerase or a helicase encoded by (+)-strand RNA viruses, or RNA polymerase from a (−)-strand RNA virus. (+)-strand RNA viruses are double stranded RNA and replicate by RNA-directed RNA synthesis using RNA-dependent RNA polymerase and the positive strand as a template. Helicase unwinds the RNA duplex to allow replication of the single stranded RNA. These viruses include viruses from the family picornaviridae (e.g., poliovirus, coxsackievirus, echovirus), togaviridae (e.g., alphavirus, flavivirus, rubivirus), arenaviridae (e.g., lymphocytic choriomeningitis virus, lassa fever virus), cononaviridae (e.g., human respiratory virus) and Hepatitis A virus. The genes encoding these proteins comprise variable and highly conserved regions which flank the variable regions.

In a preferred embodiment, the detection scheme for the PCR products generated from the bioagent(s) incorporates three features. First, the technique simultaneously detects and differentiates multiple (generally about 6–10) PCR products. Second, the technique provides a BCS that uniquely identifies the bioagent from the possible primer sites. Finally, the detection technique is rapid, allowing multiple PCR reactions to be run in parallel.

In one embodiment, the method can be used to detect the presence of antibiotic resistance and/or toxin genes in a bacterial species. For example, *Bacillus anthracis* comprising a tetracycline resistance plasmid and plasmids encoding one or both *anthracis* toxins (px01 and/or px02) can be detected by using antibiotic resistance primer sets and toxin gene primer sets. If the *B. anthracis* is positive for tetracycline resistance, then a different antibiotic, for example quinalone, is used.

Mass spectrometry (MS)-based detection of PCR products provides all of these features with additional advantages. MS is intrinsically a parallel detection scheme without the need for radioactive or fluorescent labels, since every amplification product with a unique base composition is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751 (Genetrace, Inc.).

Upon ionization, several peaks are observed from one sample due to the formation of ions with different charges. Averaging the multiple readings of molecular mass obtained from a single mass spectrum affords an estimate of molecular mass of the bioagent. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In general, the mass spectrometric techniques which can be used in the present invention include, but are not limited to, tandem mass spectrometry, infrared multiphoton dissociation and pyrolytic gas chromatography mass spectrometry (PGC-MS). In one embodiment of the invention, the bioagent detection system operates continually in bioagent detection mode using pyrolytic GC-MS without PCR for rapid detection of increases in biomass (for example, increases in fecal contamination of drinking water or of germ warfare agents). To achieve minimal latency, a continuous sample stream flows directly into the PGC-MS combustion chamber. When an increase in biomass is detected, a PCR process is automatically initiated. Bioagent presence produces elevated levels of large molecular fragments from 100–7,000 Da which are observed in the PGC-MS spectrum. The observed mass spectrum is compared to a threshold level and when levels of biomass are determined to exceed a predetermined threshold, the bioagent classification process described hereinabove(combining PCR and MS, preferably FT-ICR MS) is initiated. Optionally, alarms or other processes (halting ventilation flow, physical isolation) are also initiated by this detected biomass level. The accurate measurement of molecular mass for large DNAs is limited by the adduction of cations from the PCR reaction to each strand, resolution of the isotopic peaks from natural abundance $^{13}C$ and $^{15}N$ isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$ charge state of an 84mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The [$^{13}C$, $^{15}N$]-depleted triphosphates are obtained, for example, by growing microorganisms on depleted media and harvesting the nucleotides (Batey et al., *Nucl. Acids Res.* 20:4515–4523, 1992).

While mass measurements of intact nucleic acid regions are believed to be adequate to determine most bioagents, tandem mass spectrometry ($MS^n$) techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series(having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar base composition or mass, or if a single amplification reaction results in a product which has the same mass as two or more bioagent reference standards, they can be distinguished by using mass-modifying "tags." In this embodiment of the invention, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, PCT WO97/33000. This further limits the number of possible base compositions consistent with any mass. For example, 5-(trifluoromethyl) deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

In another amplification reaction, the number of G and C residues in each strand is determined using, for example, the cytidine analog 5-methylcytosine (5-meC) or propyne C.

Figures 1, 1A, 2, 3, 4:
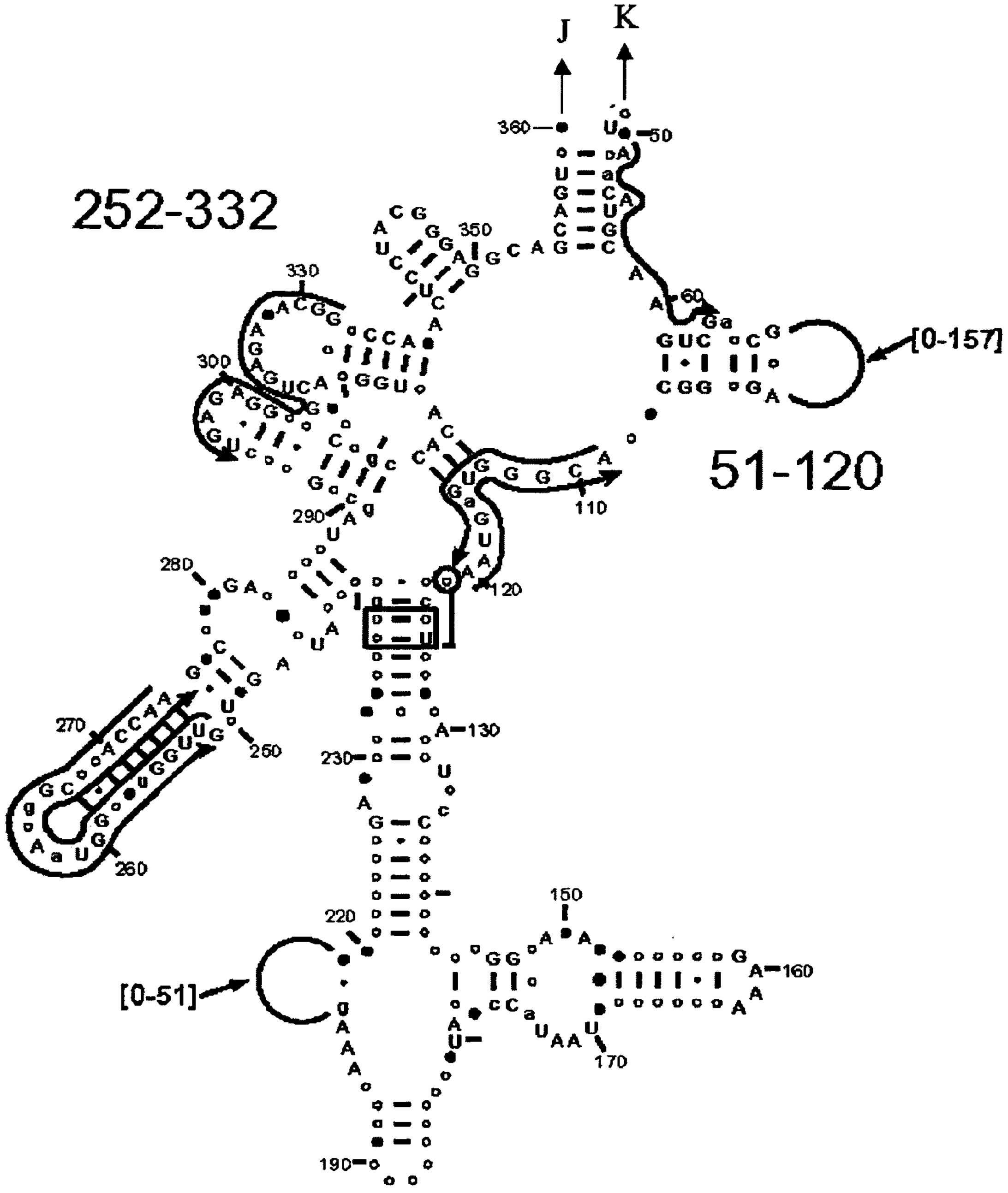
FIG. 4 is a schematic diagram of base composition signature determination using nucleotide analog "tags" to determine base composition signatures.

The combination of the A/T reaction and G/C reaction, followed by molecular weight determination, provides a unique base composition. This method is summarized in FIG. 4 and Table 1.

TABLE 1

| Mass tag | Double strand sequence | Single strand sequence | Total Δmass this strand | Base info this strand | Base info other strand | Total base comp. Top strand | Total base comp. Bottom strand |
|---|---|---|---|---|---|---|---|
| T*Δmass (T* − T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |
| C*Δmass (C* − C) = y | TAC*GTAC*GT ATGC*ATGC*A | TAC*GTAC*GT | 2x | 2C | 2G | | |
| | | ATGC*ATGC*A | 2x | 2C | 2G | | |

Figures 1, 1A, 2, 3, 4, 5:
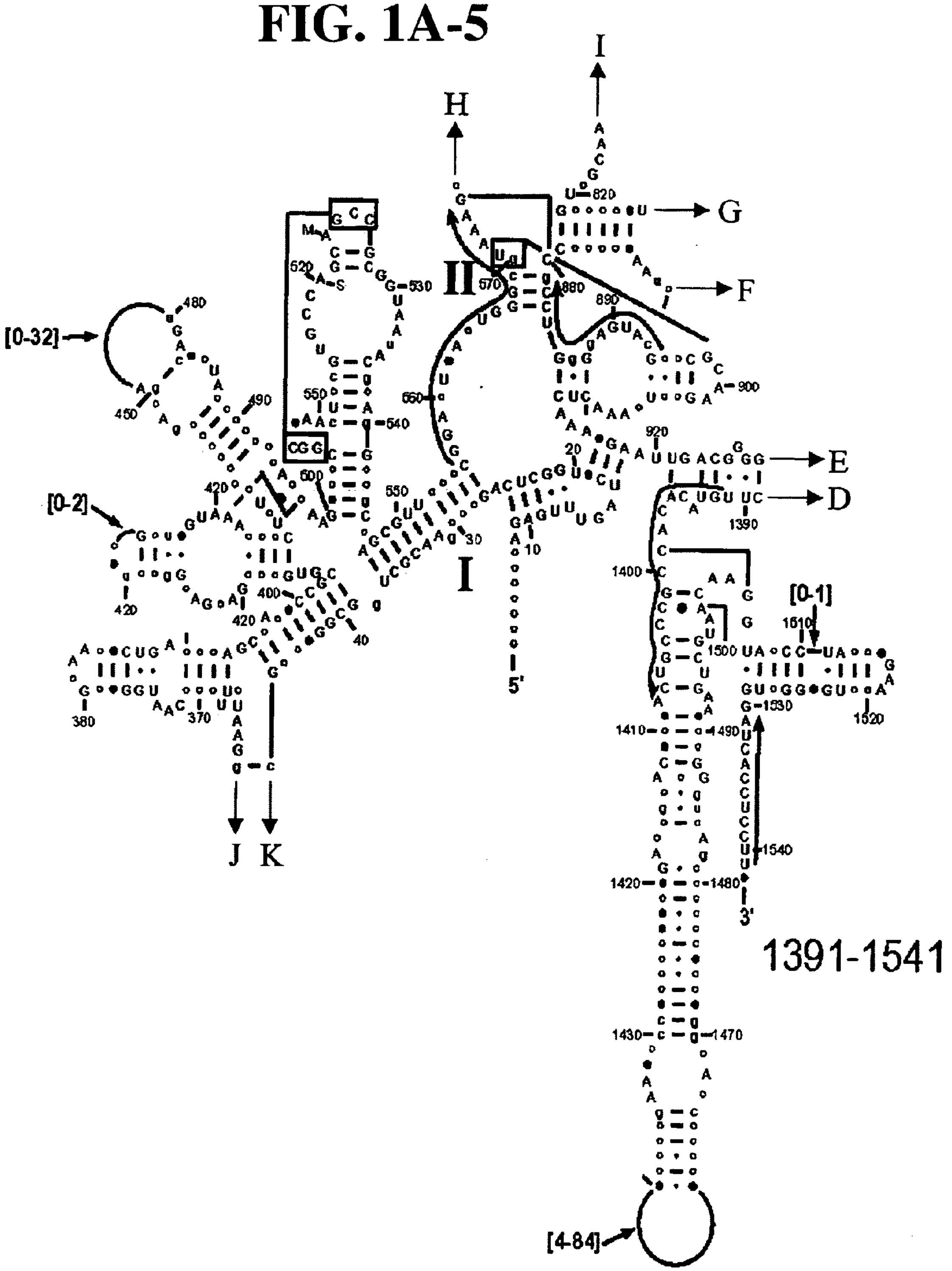
FIG. 5 shows the deconvoluted mass spectra of a *Bacillus anthracis* region with and without the mass tag phosphorothioate A (A*). The two spectra differ in that the measured molecular weight of the mass tag-containing sequence is greater than the unmodified sequence.

The mass tag phosphorothioate A (A*) was used to distinguish a *Bacillus anthracis* cluster. The *B. anthracis* ($A_{14}G_9C_{14}T_9$) had an average MW of 14072.26, and the *B. anthracis* ($A_1A^*_{13}G_9C_{14}T_9$) had an average molecular weight of 14281.11 and the phosphorothioate A had an average molecular weight of +16.06 as determined by ESI-TOF MS. The deconvoluted spectra are shown in FIG. 5.

In another example, assume the measured molecular masses of each strand are 30,000.115 Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. The detection processing uses matched filtering of BCS observed in mass-basecount space and allows for detection and subtraction of signatures from known, harmless organisms, and for detection of unknown bioagent threats. Comparison of newly observed bioagents to known bioagents is also possible, for estimation of threat level, by comparing their BCS to those of known organisms and to known forms of pathogenicity enhancement, such as insertion of antibiotic resistance genes or toxin genes.

Processing may end with a Bayesian classifier using log likelihood ratios developed from the observed signals and average background levels. The program emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database (e.g. GenBank) is used to define the mass basecount matched filters. The database contains known threat agents and benign background organisms. The latter is used to estimate and subtract the signature produced by the background organisms. A maximum likelihood detection of known background organisms is implemented using matched filters and a running-sum estimate of the noise covariance. Background signal strengths are estimated and used along with the matched filters to form signatures which are then subtracted. the maximum likelihood process is applied to this "cleaned up" data in a similar manner employing matched filters for the organisms and a running-sum estimate of the noise-covariance for the cleaned up data.

In one embodiment, a strategy to "triangulate" each organism by measuring signals from multiple core genes is used to reduce false negative and false positive signals, and enable reconstruction of the origin or hybrid or otherwise engineered bioagents. After identification of multiple core genes, alignments are created from nucleic acid sequence databases. The alignments are then analyzed for regions of conservation and variation, and potential primer binding sites flanking variable regions are identified. Next, amplification target regions for signature analysis are selected which distinguishes organisms based on specific genomic differences (i.e., base composition). For example, detection of signatures for the three part toxin genes typical of *B. anthracis* (Bowen, J. E. and C. P. Quinn, *J. Appl. Microbiol.* 1999, 87, 270–278) in the absence of the expected signatures from the *B. anthracis* genome would suggest a genetic engineering event.

The present method can also be used to detect single nucleotide polymorphisms (SNPs), or multiple nucleotide polymorphisms, rapidly and accurately. A SNP is defined as a single base pair site in the genome that is different from one individual to another. The difference can be expressed either as a deletion, an insertion or a substitution, and is frequently linked to a disease state. Because they occur every 100–1000 base pairs, SNPs are the most frequently bound type of genetic marker in the human genome.

For example, sickle cell anemia results from an A–T transition, which encodes a valine rather than a glutamic acid residue. Oligonucleotide primers may be designed such that they bind to sequences which flank a SNP site, followed by nucleotide amplification and mass determination of the amplified product. Because the molecular masses of the resulting product from an individual who does not have sickle cell anemia is different from that of the product from an individual who has the disease, the method can be used to distinguish the two individuals. Thus, the method can be used to detect any known SNP in an individual and thus diagnose or determine increased susceptibility to a disease or condition.

In one embodiment, blood is drawn from an individual and peripheral blood mononuclear cells (PBMC) are isolated and simultaneously tested, preferably in a high-throughput screening method, for one or more SNPs using appropriate primers based on the known sequences which flank the SNP region. The National Center for Biotechnology Information maintains a publicly available database of SNPs (www.ncbi.nlm.nih.gov/SNP/).

The method of the present invention can also be used for blood typing. The gene encoding A, B or O blood type can differ by four single nucleotide polymorphisms. If the gene contains the sequence CGTGGTGACCCTT (SEQ ID NO:5), antigen A results. If the gene contains the sequence CGTCGTCACCGCTA (SEQ ID NO:6) antigen B results. If the gene contains the sequence CGTGGT-ACCCCTT (SEQ ID NO:7), blood group O results ("–" indicates a deletion). These sequences can be distinguished by designing a single primer pair which flanks these regions, followed by amplification and mass determination.

While the present invention has been described with specificity in accordance with certain of its preferred embodiments, the following examples serve only to illustrate the invention and are not intended to limit the same.

EXAMPLE 1

Nucleic Acid Isolation and PCR

In one embodiment, nucleic acid is isolated from the organisms and amplified by PCR using standard methods prior to BCS determination by mass spectrometry. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.). The nucleic acid is then amplified using standard methodology, such as PCR, with primers which bind to conserved regions of the nucleic acid which contain an intervening variable sequence as described below.

EXAMPLE 2

Mass Spectrometry

FTICR Instrumentation: The FTICR instrument is based on a 7 tesla actively shielded superconducting magnet and modified Bruker Daltonics Apex II 70e ion optics and vacuum chamber. The spectrometer is interfaced to a LEAP PAL autosampler and a custom fluidics control system for high throughput screening applications. Samples are analyzed directly from 96-well or 384-well microtiter plates at a rate of about 1 sample/minute. The Bruker data-acquisition platform is supplemented with a lab-built ancillary NT datastation which controls the autosampler and contains an arbitrary waveform generator capable of generating complex rf-excite waveforms (frequency sweeps, filtered noise, stored waveform inverse Fourier transform (SWIFT), etc.) for sophisticated tandem MS experiments. For oligonucleotides in the 20–30-mer regime typical performance characteristics include mass resolving power in excess of 100,000 (FWHM), low ppm mass measurement errors, and an operable m/z range between 50 and 5000 m/z.

Modified ESI Source: In sample-limited analyses, analyte solutions are delivered at 150 nL/minute to a 30 mm i.d. fused-silica ESI emitter mounted on a 3-D micromanipulator. The ESI ion optics consist of a heated metal capillary, an rf-only hexapole, a skimmer cone, and an auxiliary gate electrode. The 6.2 cm rf-only hexapole is comprised of 1 mm diameter rods and is operated at a voltage of 380 Vpp at a frequency of 5 MHz. A lab-built electromechanical shutter can be employed to prevent the electrospray plume from entering the inlet capillary unless triggered to the "open" position via a TTL pulse from the data station. When in the "closed" position, a stable electrospray plume is maintained between the ESI emitter and the face of the shutter. The back face of the shutter arm contains an elastomeric seal which can be positioned to form a vacuum seal with the inlet capillary. When the seal is removed, a 1 mm gap between the shutter blade and the capillary inlet allows constant pressure in the external ion reservoir regardless of whether the shutter is in the open or closed position. When the shutter is triggered, a "time slice" of ions is allowed to enter the inlet capillary and is subsequently accumulated in the external ion reservoir. The rapid response time of the ion shutter (<25 ms) provides reproducible, user defined intervals during which ions can be injected into and accumulated in the external ion reservoir.

Apparatus for Infrared Multiphoton Dissociation

A 25 watt CW $CO_2$ laser operating at 10.6 μm has been interfaced to the spectrometer to enable infrared multiphoton dissociation (IRMPD) for oligonucleotide sequencing and other tandem MS applications. An aluminum optical bench is positioned approximately 1.5 m from the actively shielded superconducting magnet such that the laser beam is aligned with the central axis of the magnet. Using standard IR-compatible mirrors and kinematic mirror mounts, the unfocused 3 mm laser beam is aligned to traverse directly through the 3.5 mm holes in the trapping electrodes of the FTICR trapped ion cell and longitudinally traverse the hexapole region of the external ion guide finally impinging on the skimmer cone. This scheme allows IRMPD to be conducted in an m/z selective manner in the trapped ion cell (e.g. following a SWIFT isolation of the species of interest), or in a broadband mode in the high pressure region of the external ion reservoir where collisions with neutral molecules stabilize IRMPD-generated metastable fragment ions resulting in increased fragment ion yield and sequence coverage.

EXAMPLE 3

Identification of Bioagents

Figure 1B:
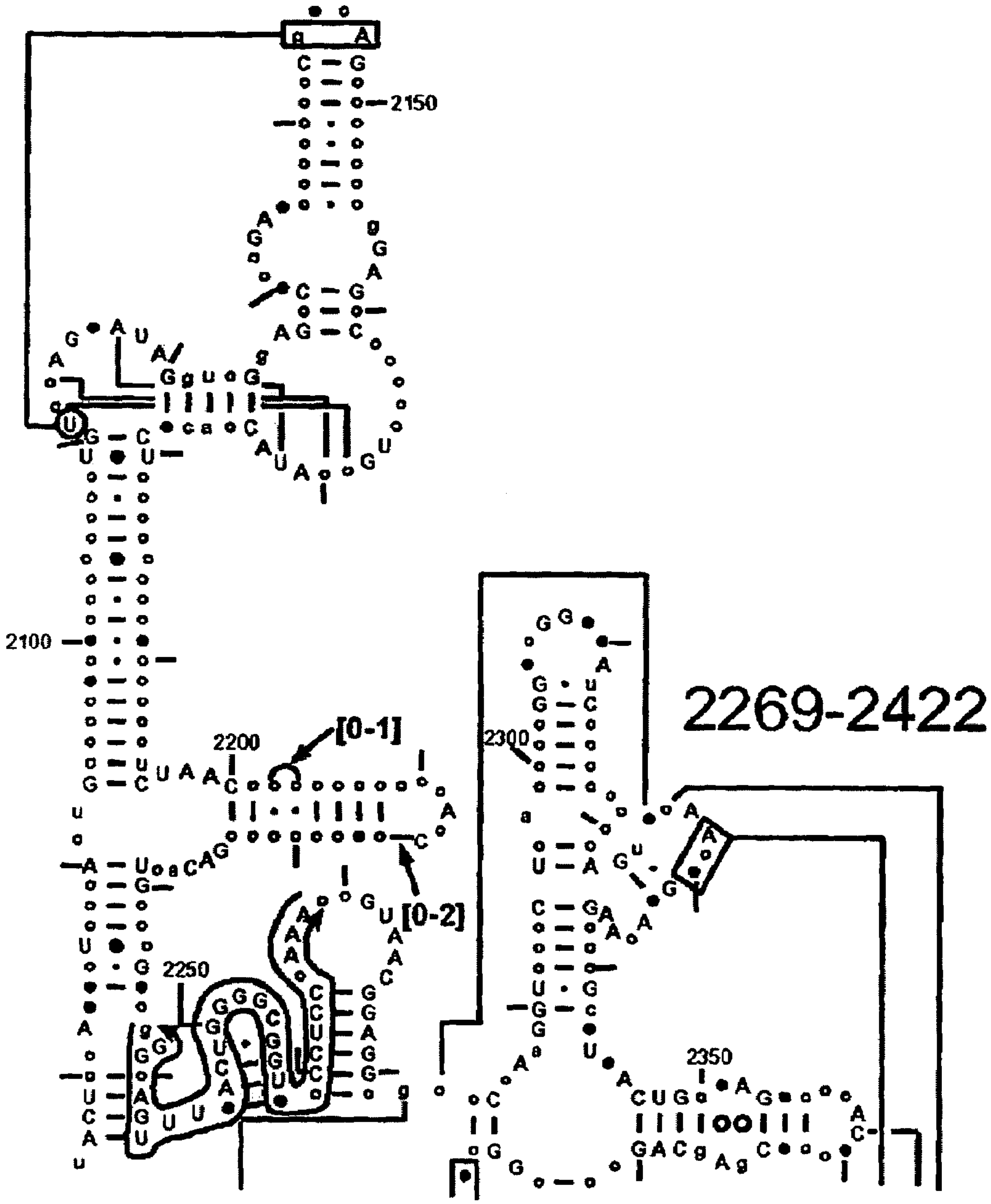
Figure 1C:
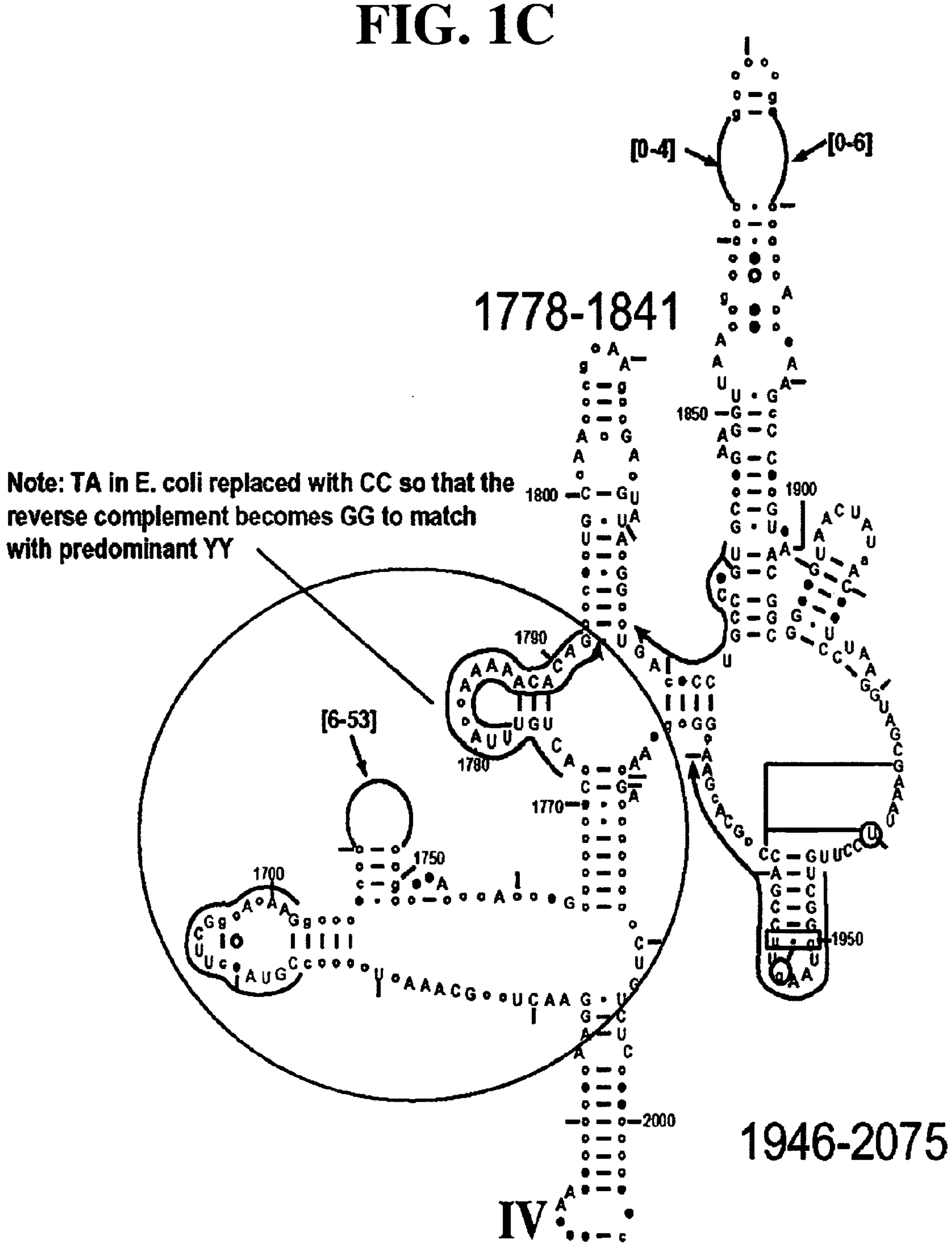
Figure 1D:
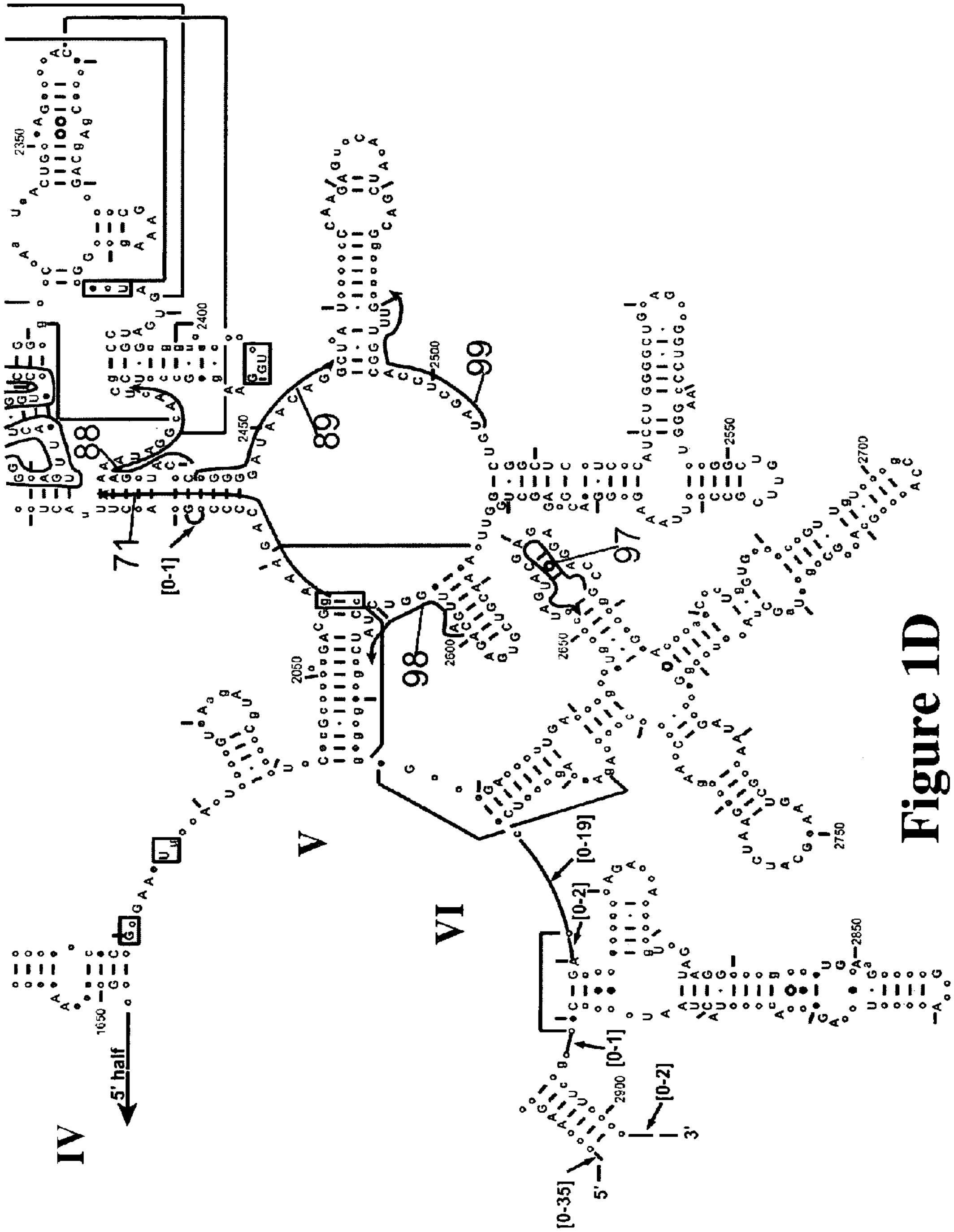
Figure 1E:
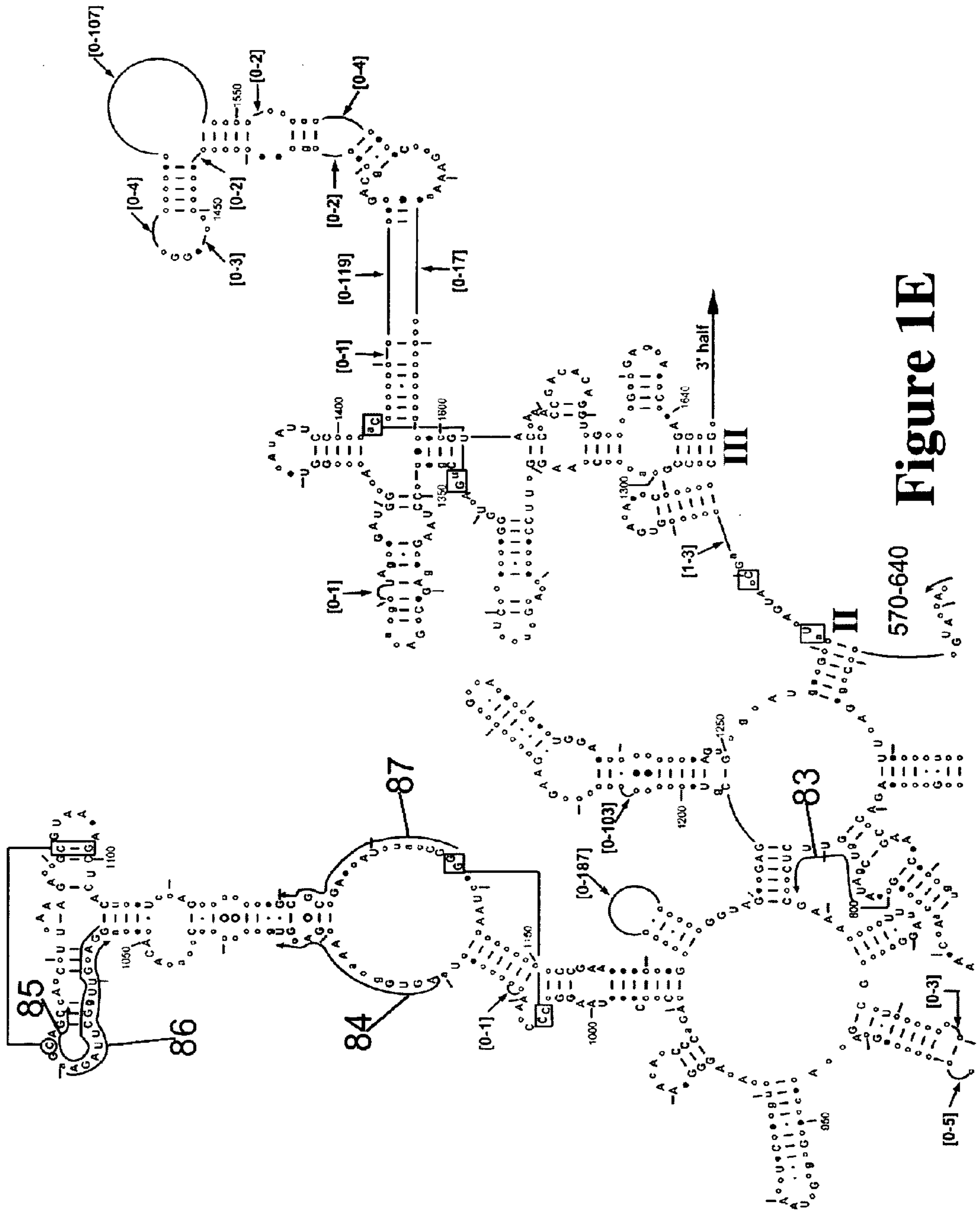
Figure 1F:
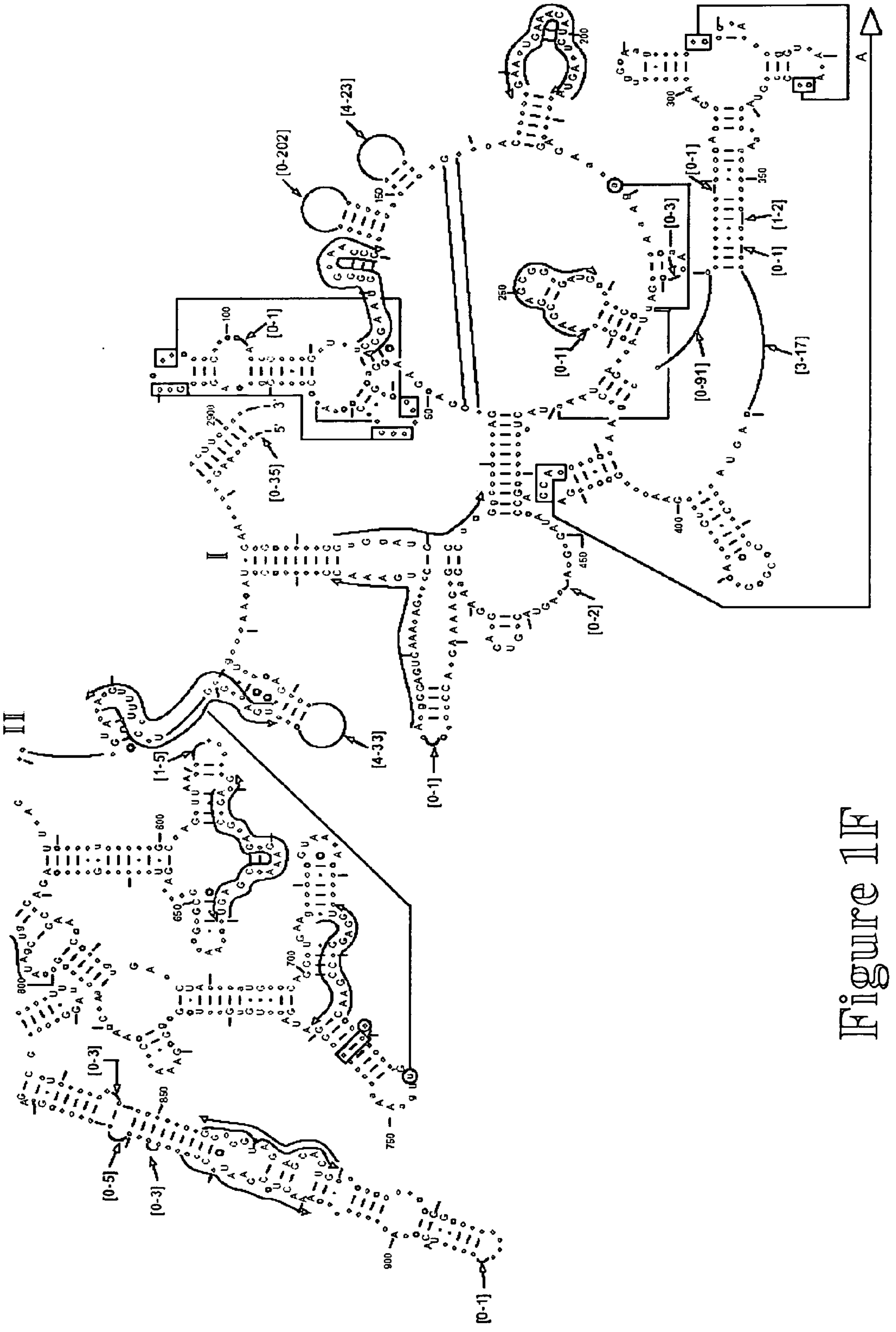
Figure 1G:
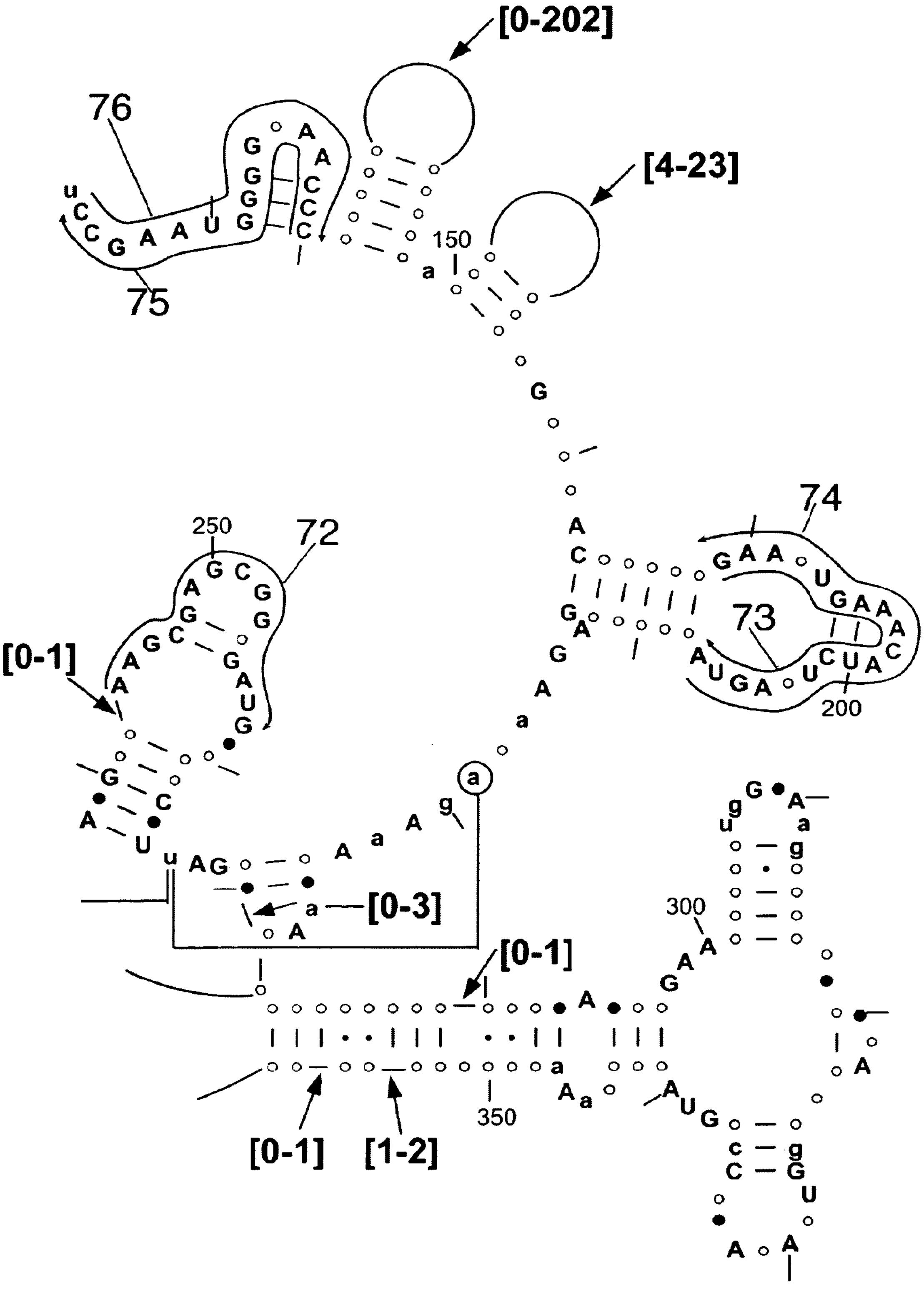
Figure 1H:
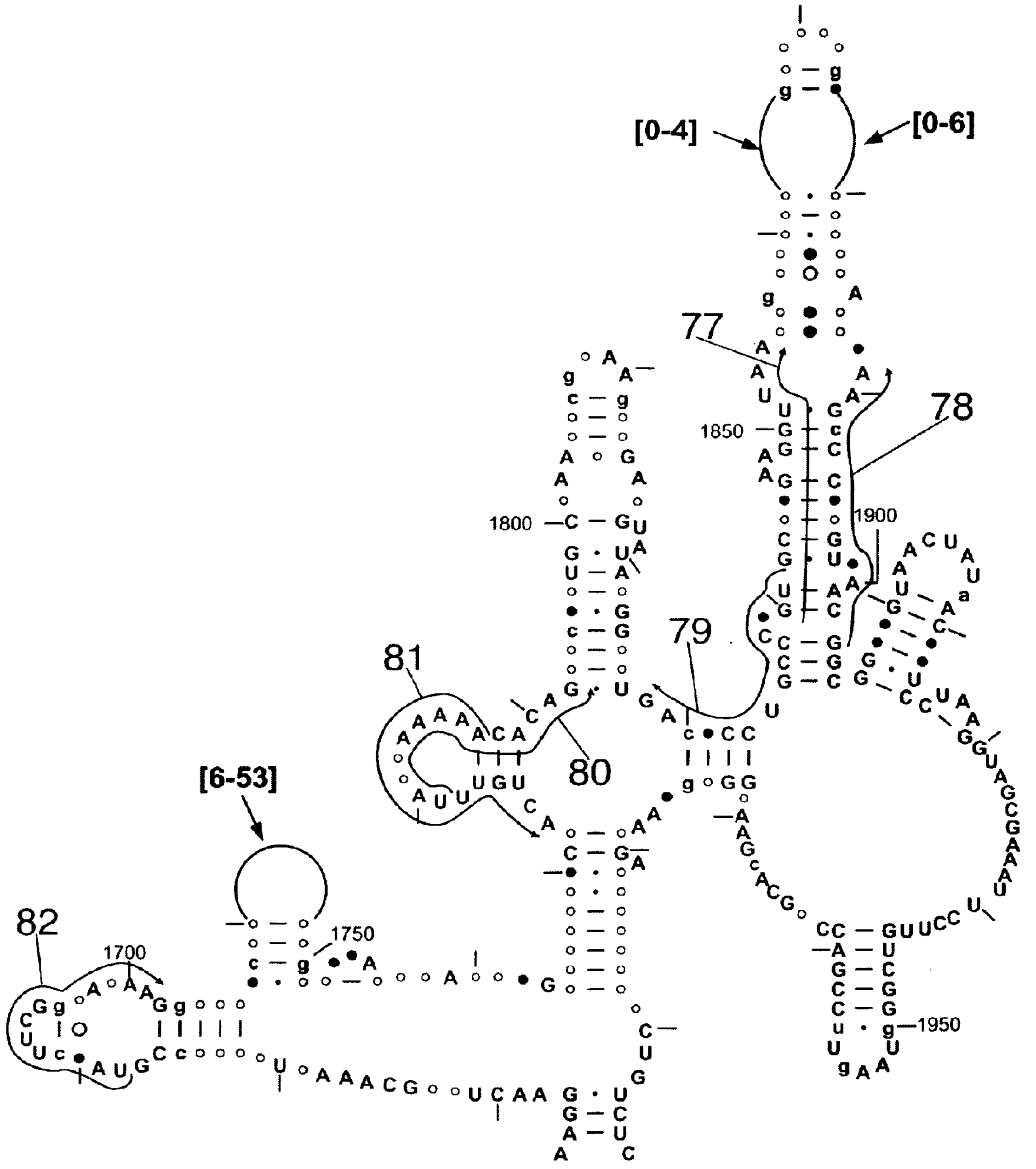
Figure 2:
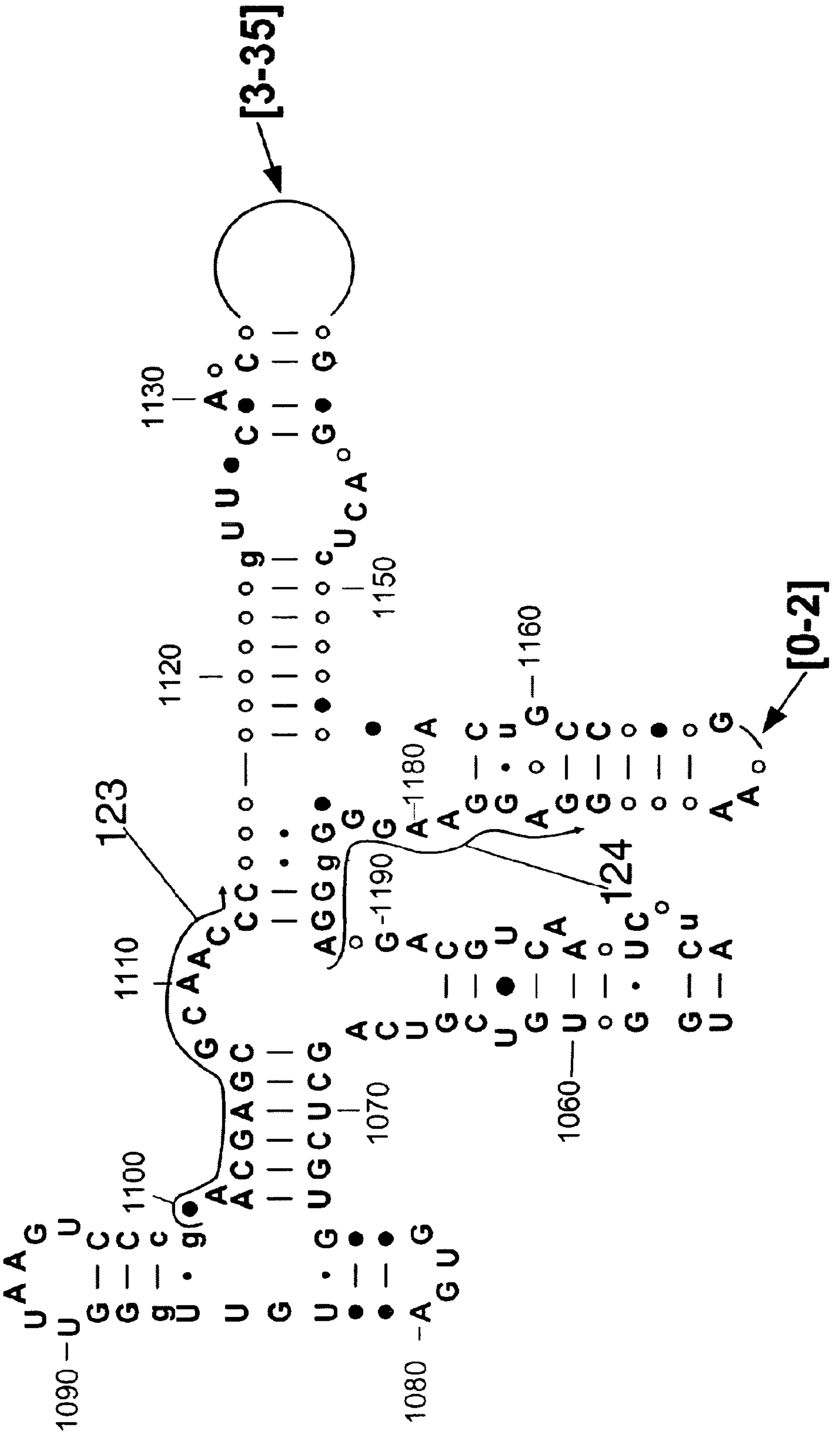
Figure 3:
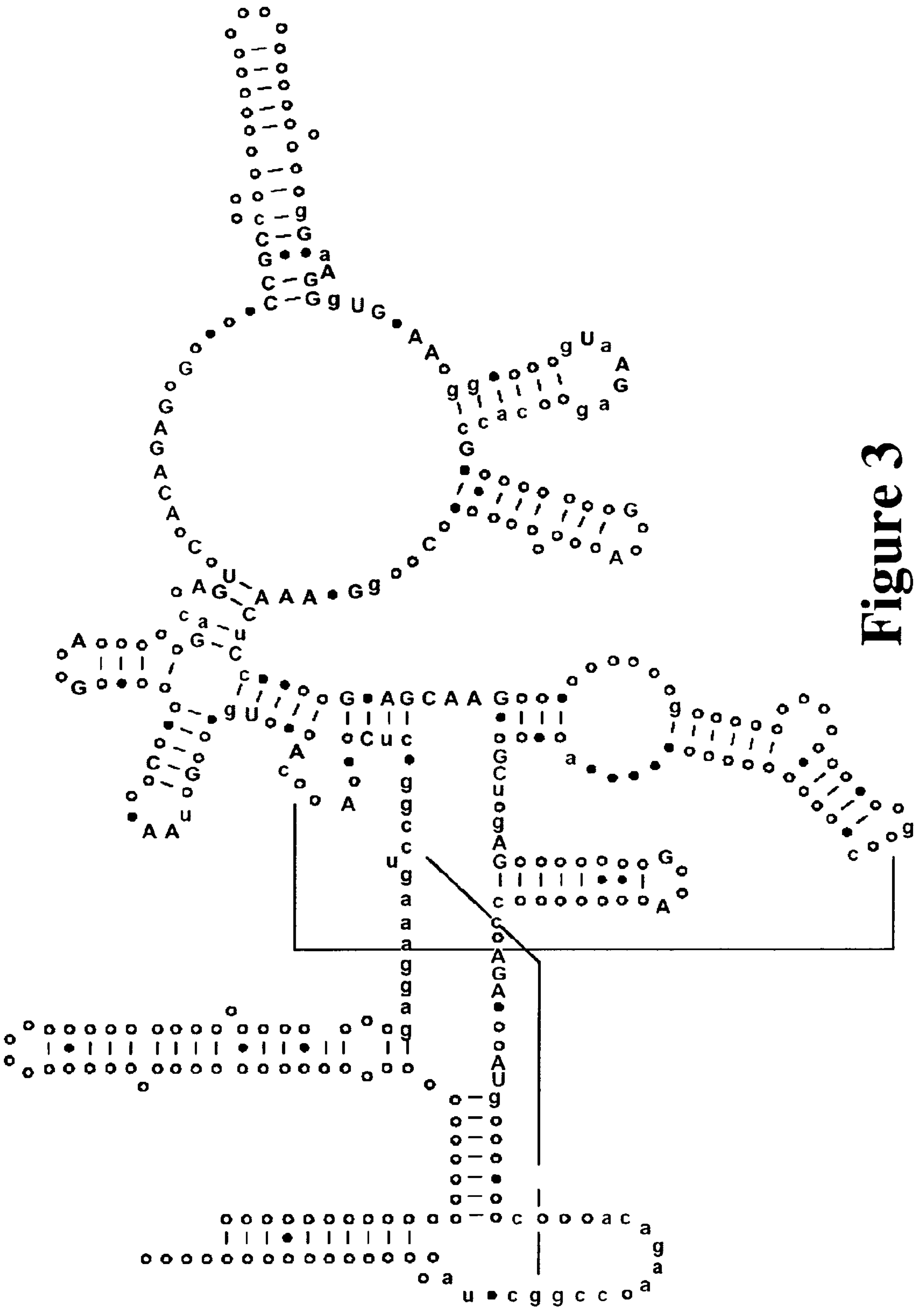
Figure 4:
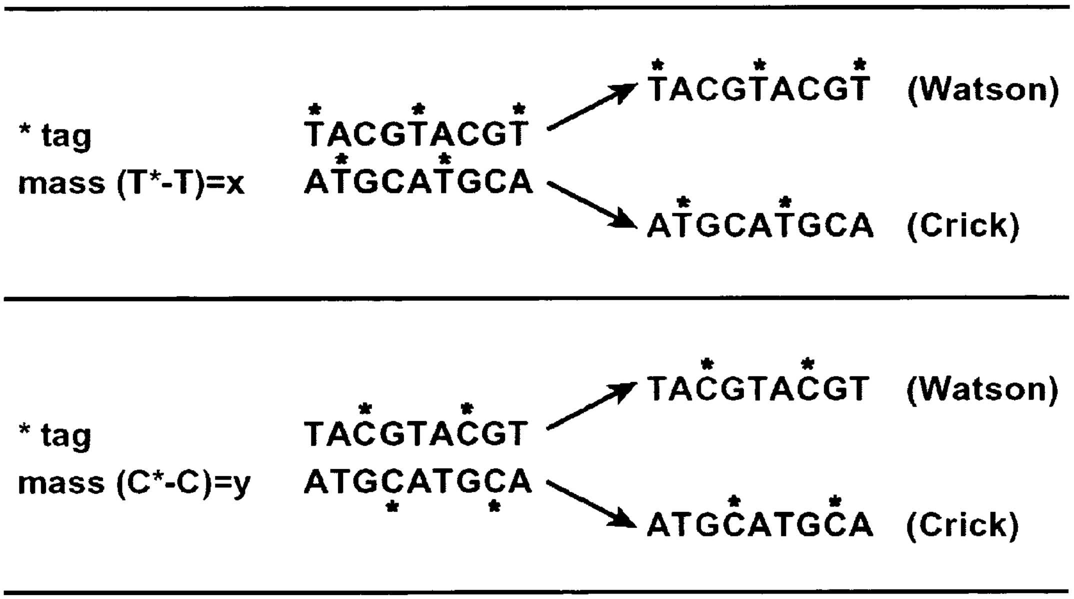
Figure 5:
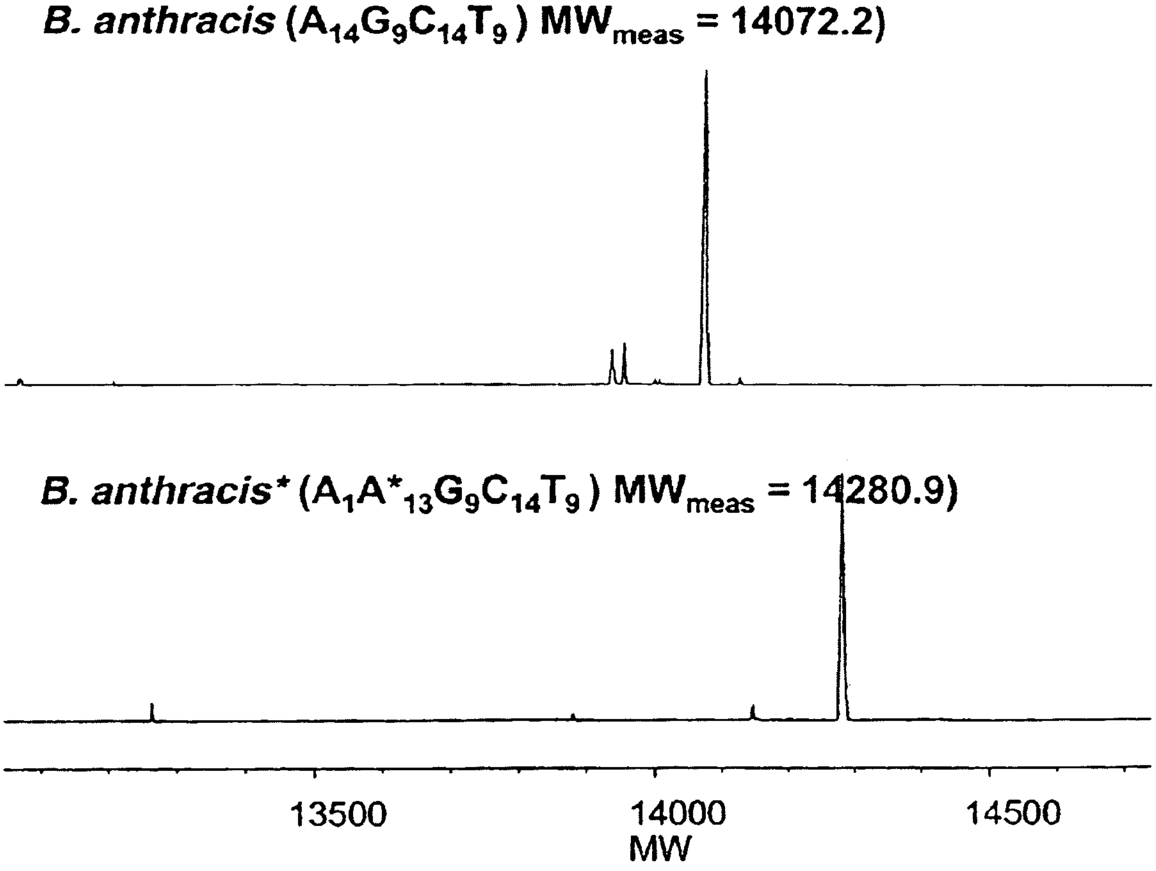

Table 1 shows a small cross section of a database of calculated molecular masses for over 9 primer sets and approximately 30 organisms. The primer sets were derived from rRNA alignment. Examples of regions from rRNA consensus alignments are shown in FIGS. 1A–1C. Lines with arrows are examples of regions to which intelligent primer pairs for PCR are designed. The primer pairs are >95% conserved in the bacterial sequence database (currently over 10,000 organisms). The intervening regions are variable in length and/or composition, thus providing the base composition "signature" (BCS) for each organism. Primer pairs were chosen so the total length of the amplified region is less than about 80–90 nucleotides. The label for each primer pair represents the starting and ending base number of the amplified region on the consensus diagram.

Included in the short bacterial database cross-section in Table 1 are many well known pathogens/biowarfare agents (shown in bold/red typeface) such as *Bacillus anthracis* or *Yersinia pestis* as well as some of the bacterial organisms found commonly in the natural environment such as Streptomyces. Even closely related organisms can be distinguished from each other by the appropriate choice of primers. For instance, two low G+C organisms, *Bacillus anthracis* and *Staph aureus*, can be distinguished from each other by using the primer pair defined by 16S_1337 or 23S_855 (ΔM of 4 Da).

TABLE 2

Cross Section Of A Database Of Calculated Molecular Masses[1]

| Primer Regions →<br>Bug Name | 16S_971 | 16S_1100 | 16S_1337 | 16S_1294 | 16S_1228 | 23S_1021 | 23S_855 | 23S_193 | 23S_115 |
|---|---|---|---|---|---|---|---|---|---|
| *Acinetobacter calcoaceticus* | 55619.1 | 55004 | 28446.7 | 35854.9 | 51295.4 | 30299 | 42654 | 39557.5 | 54999 |
| ***Bacillus anthracis*** | **55005** | **54388** | **28448** | **35238** | **51296** | **30295** | **42651** | **39560** | **56850** |
| *Bacillus cereus* | 55622.1 | 54387.9 | 28447.6 | 35854.9 | 51296.4 | 30295 | 42651 | 39560.5 | 56850.3 |
| *Bordetella bronchiseptica* | 56857.3 | 51300.4 | 28446.7 | 35857.9 | 51307.4 | 30299 | 42653 | 39559.5 | 51920.5 |
| *Borrelia burgdoferi* | 56231.2 | 55621.1 | 28440.7 | 35852.9 | 51295.4 | 30297 | 42029.9 | 38941.4 | 52524.6 |
| ***Brucella abortus*** | **58098** | **55011** | **28448** | **35854** | **50683** | | | | |
| *Campylobacter jejuni* | 58088.5 | 54386.9 | 29061.8 | 35856.9 | 50674.3 | 30294 | 42032.9 | 39558.5 | 45732.5 |
| ***Chlamydia pnuemoniae*** | **55000** | **55007** | **29063** | **35855** | **50676** | **30295** | **42036** | **38941** | **56230** |
| ***Clostridium botulinum*** | **55006** | **53767** | **28445** | **35855** | **51291** | **30300** | **42656** | **39582** | **54999** |
| *Clostridium difficile* | 56855.3 | 54386.9 | 28444.7 | 35853.9 | 51296.4 | 30294 | 41417.8 | 39556.5 | 55612.2 |
| *Enterococcus faecalis* | 55620.1 | 54387.9 | 28447.6 | 35858.9 | 51296.4 | 30297 | 42652 | 39559.5 | 56849.3 |
| ***Escherichia coli*** | **55622** | **55009** | **28445** | **35857** | **51301** | **30301** | **42656** | **39562** | **54999** |
| ***Francisella tularensis*** | **53769** | **54385** | **28445** | **35856** | **51298** | | | | |
| *Haemophilus influenzae* | 55620.1 | 55006 | 26444.7 | 35855.9 | 51298.4 | 30298 | 42656 | 39560.5 | 55613.1 |
| *Klebsiella pneumoniae* | 55622.1 | 55008 | 28442.7 | 35856.9 | 51297.4 | 30300 | 42655 | 39562.5 | 55000 |
| ***Legionella pneumophila*** | **55618** | **55628** | **28446** | **35857** | **51303** | | | | |
| *Mycobacterium avium* | 54390.9 | 55631.1 | 29064.8 | 35858.9 | 51915.5 | 30298 | 42656 | 38942.4 | 56241.2 |
| *Myobacterium leprae* | 54389.9 | 55629.1 | 29064.8 | 35860.9 | 51917.5 | 30298 | 42656 | 39559.5 | 56240.2 |
| *Myobacterium tuberculosis* | 54390.9 | 55629.1 | 29064.8 | 35860.9 | 51301.4 | 30299 | 42656 | 39560.5 | 56243.2 |
| *Mycoplasma genitalium* | 53143.7 | 45115.4 | 29061.8 | 35854.9 | 50671.3 | 30294 | 43264.1 | 39558.5 | 56842.4 |
| *Mycoplasma pneumoniae* | 53143.7 | 45118.4 | 29061.8 | 35854.9 | 50673.3 | 30294 | 43264.1 | 39559.5 | 56843.4 |
| *Neissena gonorrhoeae* | 55627.1 | 54389.9 | 28445.7 | 35855.9 | 51302.4 | 30300 | 42649 | 39561.5 | 55000 |
| ***Pseudomonas aeruginosa*** | **55623** | **55010** | **28443** | **35858** | **51301** | **30298** | **43272** | **39558** | **55619** |
| ***Rickettsia prowazekii*** | **58093** | **55621** | **28448** | **35853** | **50677** | **30293** | **42650** | **39559** | **53139** |
| ***Rickettsia rickettsii*** | **58094** | **55623** | **28448** | **35853** | **50679** | **30293** | **42648** | **39559** | **53755** |
| ***Salmonella typhimurium*** | **55622** | **55005** | **28445** | **35857** | **51301** | **30301** | **42658** | | |
| ***Shigella dysenteriae*** | **55623** | **55009** | **28444** | **35857** | **51301** | | | | |
| *Staphylococcus aureus* | 56854.3 | 54386.9 | 28443.7 | 35852.9 | 51294.4 | 30298 | 42655 | 39559.5 | 57466.4 |

TABLE 2-continued

| Cross Section Of A Database Of Calculated Molecular Masses[1] | | | | | | | | | |
|---|---|---|---|---|---|---|---|---|---|
| Primer Regions → Bug Name | 16S_971 | 16S_1100 | 16S_1337 | 16S_1294 | 16S_1228 | 23S_1021 | 23S_855 | 23S_193 | 23S_115 |
| *Streptomyces* | 54389.9 | 59341.6 | 20963.8 | 35858.9 | 51300.4 | | | 39563.5 | 56864.3 |
| *Treponema pallidum* | 56245.2 | 55631.1 | 28445.7 | 35851.9 | 51297.4 | 30299 | 42034.9 | 38939.4 | 57473.4 |
| ***Vibrio cholerae*** | **55625** | **55626** | **28443** | **35857** | **52536** | **29063** | **30303** | **35241** | **50675** |
| *Vibrio parahaemolyticus* | 54384.9 | 55626.1 | 28444.7 | 34620.7 | 50064.2 | | | | |
| ***Yersinia pestis*** | **55620** | **55626** | **28443** | **35857** | **51299** | | | | |

[1]Molecular mass distribution of PCR amplified regions for a selection of organisms (rows) across various primer pairs (columns). Pathogens are shown in bold. Empty cells indicate presently incomplete or missing data.

Figure 6:
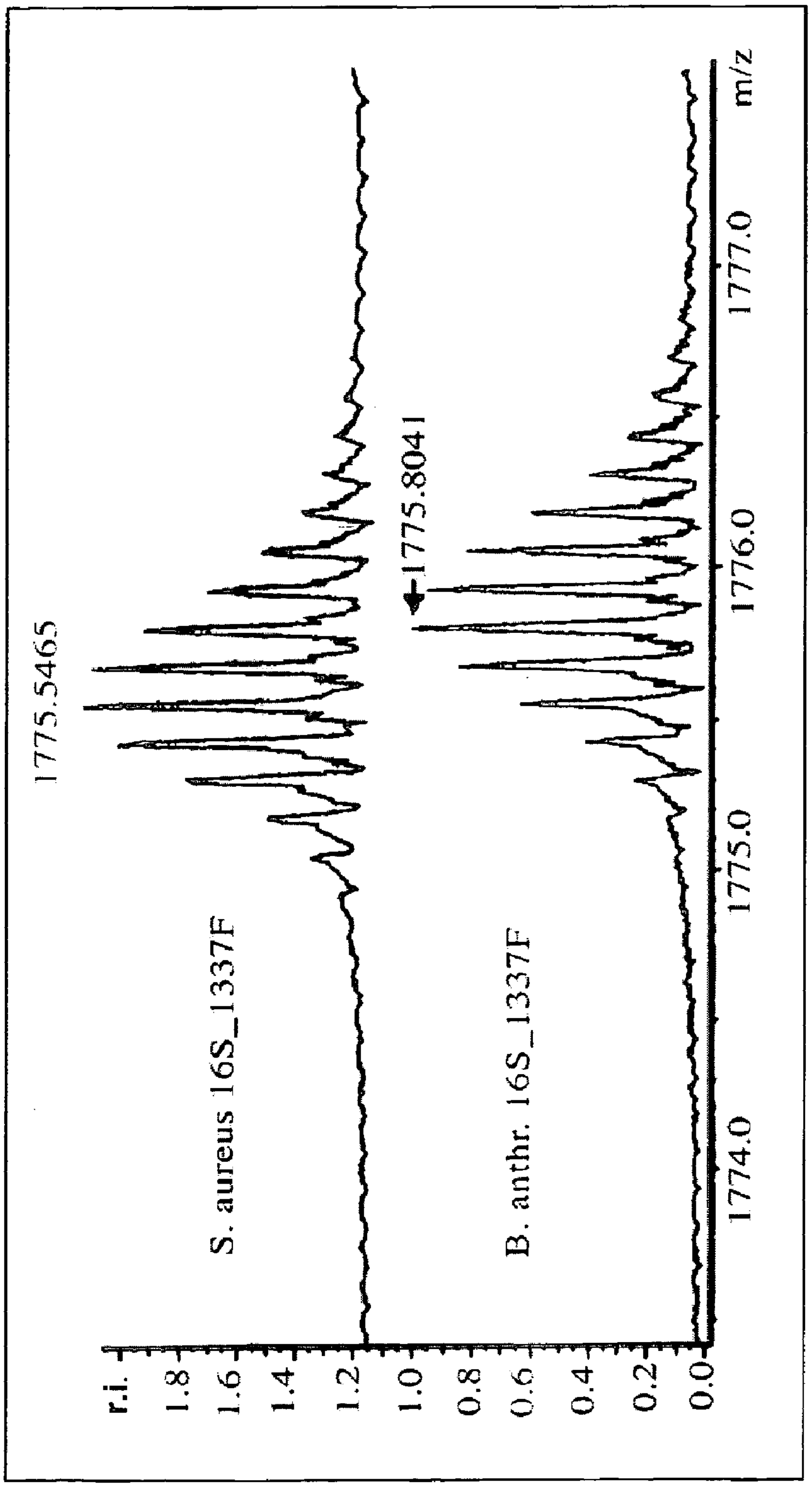
FIG. 6 shows base composition signature (BCS) spectra from PCR products from *Staphylococcus aureus* (*S. aureus* 16S_1337F) and *Bacillus anthracus* (*B. anthr.* 16S_1337F), amplified using the same primers. The two strands differ by only two (AT→CG) substitutions and are clearly distinguished on the basis of their BCS.

FIG. 6 shows the use of ESI-FT-ICR MS for measurement of exact mass. The spectra from 46mer PCR products originating at position 1337 of the 16S rRNA from *S. aureus* (upper) and *B. anthracis* (lower) are shown. These data are from the region of the spectrum containing signals from the $[M-8H+]^{8-}$ charge states of the respective 5'-3' strands. The two strands differ by two (AT→CG) substitutions, and have measured masses of 14206.396 and 14208.373±0.010 Da, respectively. The possible base compositions derived from the masses of the forward and reverse strands for the *B. anthracis* products are listed in Table 3.

TABLE 3

| Possible base composition for *B. anthracis* products | | |
|---|---|---|
| Calc. Mass | Error | Base Comp. |
| 14208.2935 | 0.079520 | A1 G17 C10 T18 |
| 14208.3160 | 0.056980 | A1 G20 C15 T10 |
| 14208.3386 | 0.034440 | A1 G23 C20 T2 |
| 14208.3074 | 0.065560 | A6 G11 C3 T26 |
| 14208.3300 | 0.043020 | A6 G14 C8 T18 |
| 14208.3525 | 0.020480 | A6 G17 C13 T10 |
| 14208.3751 | 0.002060 | A6 G20 C18 T2 |
| 14208.3439 | 0.029060 | A11 G8 C1 T26 |
| 14208.3665 | 0.006520 | A11 G11 C6 T18 |
| **14208.3890** | **0.016020** | **A11 G14 C11 T10** |
| 14208.4116 | 0.038560 | A11 G17 C16 T2 |
| 14208.4030 | 0.029980 | A16 G8 C4 T18 |
| 14208.4255 | 0.052520 | A16 G11 C9 T10 |
| 14208.4481 | 0.075060 | A16 G14 C14 T2 |
| 14208.4395 | 0.066480 | A21 G5 C2 T18 |
| 14208.4620 | 0.089020 | A21 G8 C7 T10 |
| 14079.2624 | 0.080600 | A0 G14 C13 T19 |
| 14079.2849 | 0.058060 | A0 G17 C18 T11 |
| 14079.3075 | 0.035520 | A0 G20 C23 T3 |
| 14079.2538 | 0.089180 | A5 G5 C1 T35 |
| 14079.2764 | 0.066640 | A5 G8 C6 T27 |
| 14079.2989 | 0.044100 | A5 G11 C11 T19 |
| 14079.3214 | 0.021560 | A5 G14 C16 T11 |
| 14079.3440 | 0.000980 | A5 G17 C21 T3 |
| 14079.3129 | 0.030140 | A10 G5 C4 T27 |
| 14079.3354 | 0.007600 | A10 G8 C9 T19 |
| **14079.3579** | **0.014940** | **A10 G11 C14 T11** |
| 14079.3805 | 0.037480 | A10 G14 C19 T3 |
| 14079.3494 | 0.006360 | A15 G2 C2 T27 |
| 14079.3719 | 0.028900 | A15 G5 C7 T19 |
| 14079.3944 | 0.051440 | A15 G8 C12 T11 |
| 14079.4170 | 0.073980 | A15 G11 C17 T3 |
| 14079.4084 | 0.065400 | A20 G2 C5 T19 |
| 14079.4309 | 0.087940 | A20 G5 C10 T13 |

Among the 16 compositions for the forward strand and the 18 compositions for the reverse strand that were calculated, only one pair (shown in bold) are complementary, corresponding to the actual base compositions of the *B. anthracis* PCR products.

EXAMPLE 4

BCS of Region from *Bacillus anthracis* and *Bacillus cereus*

Figure 7:
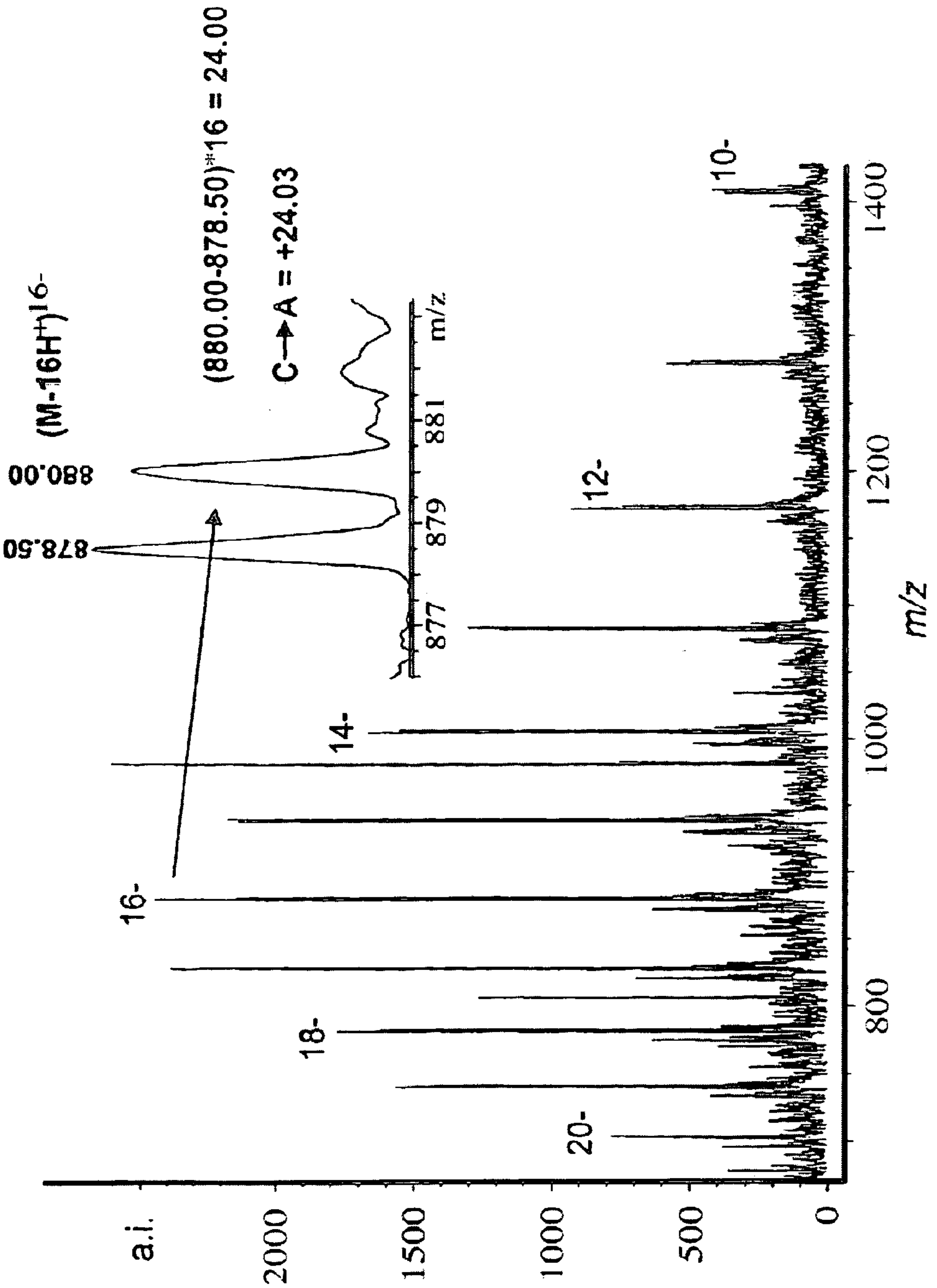
FIG. 7 shows that a single difference between two sequences ($A_{14}$ in *B. anthracis* vs. $A_{15}$ in *B. cereus*) can be easily detected using ESI-TOF mass spectrometry.

A conserved Bacillus region from *B. anthracis* ($A_{14}G_9C_{14}T_9$) and *B. cereus* ($A_{15}G_9C_{13}T_9$) having a C to A base change was synthesized and subjected to ESI-TOF MS. The results are shown in FIG. 7 in which the two regions are clearly distinguished using the method of the present invention (MW=14072.26 vs. 14096.29).

EXAMPLE 5

Identification of Additional Bioagents

In other examples of the present invention, the pathogen *Vibrio cholera* can be distinguished from *Vibrio parahemolyticus* with ΔM>600 Da using one of three 16S primer sets shown in Table 2 (16S_971, 16S_1228 or 16S_1294) as shown in Table 4. The two mycoplasma species in the list (*M. genitalium* and *M. pneumoniae*) can also be distinguished from each other, as can the three mycobacteriae. While the direct mass measurements of amplified products can identify and distinguish a large number of organisms, measurement of the base composition signature provides dramatically enhanced the base composition signature provides dramatically enhanced resolving power for closely related organisms. In cases such as *Bacillus anthracis* and *Bacillus cereus* that are virtually indistinguishable from each other based solely on mass differences, compositional analysis or fragmentation patterns are used to resolve the differences. The single base difference between the two organisms yields different fragmentation patterns, and despite the presence of the ambiguous/unidentified base N at position 20 in *B. anthracis*, the two organisms can be identified.

Tables 4a–b show examples of primer pairs from Table 1 which distinguish pathogens from background.

TABLE 4a

| Organism name | 23S_855 | 16S_1337 | 23S_1021 |
|---|---|---|---|
| *Bacillus anthracis* | 42650.98 | 28447.65 | 30294.98 |
| *Staphylococcus aureus* | 42654.97 | 28443.67 | 30297.96 |

TABLE 4b

| Organism name | 16S_971 | 16S_1294 | 16S_1228 |
|---|---|---|---|
| *Vibrio cholerae* | 55625.09 | 35856.87 | 52535.59 |
| *Vibrio parahaemolyticus* | 54384.91 | 34620.67 | 50064.19 |

Table 4 shows the expected molecular weight and base composition of region 16S 1100–1188 in *Mycobacterium avium* and *Streptomyces sp.*

TABLE 5

| Region | Organism name | Length | Molecular weight | Base comp. |
|---|---|---|---|---|
| 16S_1100-1188 | *Mycobacterium avium* | 82 | 25624.1728 | $A_{16}G_{32}C_{18}T_{16}$ |
| 16S_1100-1188 | *Streptomyces sp.* | 96 | 29904.871 | $A_{17}G_{38}C_{27}T_{14}$ |

Table 6 shows base composition (single strand) results for 16—$S_{13}$ 1100–1188 primer amplification reactions for different species of bacteria. Species which are repeated in the table (e.g., *Clostridium botulinum*) are different strains which have different base compositions in the 16S_1100–1188 region.

The same organism having different base compositions are different strains. Groups of organisms which are highlighted or in italics have the same base compositions in the amplified region. Some of these organisms can be distinguished using multiple primers. For example, *Bacillus anthracis* can be distinguished from *Bacillus cereus* and *Bacillus thuringiensis* using the primer 16S_971–1062 (Table 6). Other primer pairs which produce unique base composition signatures are shown in Table 6 (bold). Clusters

TABLE 6

| Organism name | Base comp. | Organism name | Base comp. |
|---|---|---|---|
| *Mycobacterium avium* | $A_{16}G_{32}C_{18}T_{16}$ | *Vibrio cholerae* | $A_{23}G_{30}C_{21}T_{16}$ |
| *Streptomyces sp.* | $A_{17}G_{38}C_{27}T_{14}$ | ***Aeromonas hydrophila*** | $\mathbf{A_{23}}G_{31}C_{21}T_{15}$ |
| *Ureaplasma urealyticum* | $A_{18}G_{30}C_{17}T_{17}$ | ***Aeromonas salmonicida*** | $\mathbf{A_{23}}G_{31}C_{21}T_{15}$ |
| *Streptomyces sp.* | $A_{19}G_{36}C_{24}T_{18}$ | *Mycoplasma genitalium* | $A_{24}G_{19}C_{12}T_{18}$ |
| *Mycobacterium leprae* | $A_{20}G_{32}C_{22}T_{16}$ | *Clostridium botulinum* | $A_{24}G_{25}C_{18}T_{20}$ |
| ***M. tuberculosis*** | $\mathbf{A_{20}}G_{33}C_{21}T_{16}$ | *Bordetella bronchiseptica* | $A_{24}G_{26}C_{19}T_{14}$ |
| ***Nocardia asteroides*** | $\mathbf{A_{20}}G_{33}C_{21}T_{16}$ | *Francisella tularensis* | $A_{24}G_{26}C_{19}T_{19}$ |
| *Fusobacterium necroforum* | $A_{21}G_{26}C_{22}T_{18}$ | ***Bacillus anthracis*** | $\mathbf{A_{24}}G_{26}C_{20}T_{18}$ |
| *Listeria monocytogenes* | $A_{21}G_{27}C_{19}T_{19}$ | ***Campylobacter jejuni*** | $\mathbf{A_{24}}G_{26}C_{20}T_{18}$ |
| *Clostridium botulinum* | $A_{21}G_{27}C_{19}T_{21}$ | ***Staphylococcus aureus*** | $\mathbf{A_{24}}G_{26}C_{20}T_{18}$ |
| *Neisseria gonorrhoeae* | $A_{21}G_{28}C_{21}T_{18}$ | *Helicobacter pylori* | $A_{24}G_{26}C_{20}T_{19}$ |
| *Bartonella quintana* | $A_{21}G_{30}C_{22}T_{16}$ | *Helicobacter pylori* | $A_{24}G_{26}C_{21}T_{18}$ |
| *Enterococcus faecalis* | $A_{22}G_{27}C_{20}T_{19}$ | *Moraxella catarrhalis* | $A_{24}G_{26}C_{23}T_{16}$ |
| *Bacillus megaterium* | $A_{22}G_{28}C_{20}T_{18}$ | *Haemophilus influenzae* Rd | $A_{24}G_{28}C_{20}T_{17}$ |
| *Bacillus subtilis* | $A_{22}G_{28}C_{21}T_{17}$ | ***Chlamydia trachomatis*** | $\mathbf{A_{24}}G_{28}C_{21}T_{16}$ |
| *Pseudomonas aeruginosa* | $A_{22}G_{29}C_{23}T_{15}$ | ***Chlamydophila pneumoniae*** | $\mathbf{A_{24}}G_{28}C_{21}T_{16}$ |
| *Legionella pneumophila* | $A_{22}G_{32}C_{20}T_{16}$ | ***C. Pneumonia*** **AR39** | $\mathbf{A_{24}}G_{28}C_{21}T_{16}$ |
| *Mycoplasma pneumoniae* | $A_{23}G_{20}C_{14}T_{16}$ | *Pseudomonas putida* | $A_{24}G_{29}C_{21}T_{16}$ |
| *Clostridium botulinum* | $A_{23}G_{26}C_{20}T_{19}$ | ***Proteus vulgaris*** | $\mathbf{A_{24}}G_{30}C_{21}T_{15}$ |
| *Enterococcus faecium* | $A_{23}G_{26}C_{21}T_{18}$ | ***Yersinia pestis*** | $\mathbf{A_{24}}G_{30}C_{21}T_{15}$ |
| *Acinetobacter calcoaceti* | $A_{23}G_{26}C_{21}T_{19}$ | ***Yersinia pseudotuberculos*** | $\mathbf{A_{24}}G_{30}C_{21}T_{15}$ |
| ***Leptospira borgpetersenii*** | $\mathbf{A_{23}}G_{26}C_{24}T_{15}$ | *Clostridium botulinum* | $A_{25}G_{24}C_{18}T_{21}$ |
| ***Leptospira interrogans*** | $\mathbf{A_{23}}G_{26}C_{24}T_{15}$ | *Clostridium tetani* | $A_{25}G_{25}C_{18}T_{20}$ |
| *Clostridium perfringens* | $A_{23}G_{27}C_{19}T_{19}$ | *Francisella tularensis* | $A_{25}G_{25}C_{19}T_{19}$ |
| ***Bacillus anthracis*** | $\mathbf{A_{23}}G_{27}C_{20}T_{18}$ | *Acinetobacter calcoacetic* | $A_{25}G_{26}C_{20}T_{19}$ |
| ***Bacillus cereus*** | $\mathbf{A_{23}}G_{27}C_{20}T_{18}$ | *Bacteriodes fragilis* | $A_{25}G_{27}C_{16}T_{22}$ |
| ***Bacillus thuringiensis*** | $\mathbf{A_{23}}G_{27}C_{20}T_{18}$ | *Chlamydophila psittaci* | $A_{25}G_{27}C_{21}T_{16}$ |
| *Aeromonas hydrophila* | $A_{23}G_{29}C_{21}T_{16}$ | *Borrelia burgdorferi* | $A_{25}G_{29}C_{17}T_{19}$ |
| *Escherichia coli* | $A_{23}G_{29}C_{21}T_{16}$ | *Streptobacillus monilifor* | $A_{26}G_{26}C_{20}T_{16}$ |
| *Pseudomonas putida* | $A_{23}G_{29}C_{21}T_{17}$ | *Rickettsia prowazekii* | $A_{26}G_{28}C_{18}T_{18}$ |
| ***Escherichia coli*** | $\mathbf{A_{23}}G_{29}C_{22}T_{15}$ | *Rickettsia rickettsii* | $A_{26}G_{28}C_{20}T_{16}$ |
| ***Shigella dysenteriae*** | $\mathbf{A_{23}}G_{29}C_{22}T_{15}$ | *Mycoplasma mycoides* | $A_{28}G_{23}C_{16}T_{20}$ |

containing very similar threat and ubiquitous non-threat organisms (e.g. *anthracis* cluster) are distinguished at high resolution with focused sets of primer pairs. The known biowarfare agents in Table 6 are *Bacillus anthracis, Yersinia pestis, Francisella tularensis* and *Rickettsia prowazekii*.

TABLE 7

| Organism | 16S_971-1062 | 16S_1228-1310 | 16S_1100-1188 |
|---|---|---|---|
| *Aeromonas hydrophila* | $A_{21}G_{29}C_{22}T_{20}$ | $A_{22}G_{27}C_{21}T_{13}$ | $A_{23}G_{31}C_{21}T_{15}$ |
| *Aeromonas salmonicida* | $A_{21}G_{29}C_{22}T_{20}$ | $A_{22}G_{27}C_{21}T_{13}$ | $A_{23}G_{31}C_{21}T_{15}$ |
| *Bacillus anthracis* | **$A_{21}G_{27}C_{22}T_{22}$** | $A_{24}G_{22}C_{19}T_{18}$ | $A_{23}G_{27}C_{20}T_{18}$ |
| *Bacillus cereus* | $A_{22}G_{27}C_{21}T_{22}$ | $A_{24}G_{22}C_{19}T_{18}$ | $A_{23}G_{27}C_{20}T_{18}$ |
| *Bacillus thuringiensis* | $A_{22}G_{27}C_{21}T_{22}$ | $A_{24}G_{22}C_{19}T_{18}$ | $A_{23}G_{27}C_{20}T_{18}$ |
| *Chlamydia trachomatis* | **$A_{22}G_{26}C_{20}T_{23}$** | **$A_{24}G_{23}C_{19}T_{16}$** | $A_{24}G_{28}C_{21}T_{16}$ |
| *Chlamydia pneumoniae* AR39 | $A_{26}G_{23}C_{20}T_{22}$ | $A_{26}G_{22}C_{16}T_{18}$ | $A_{24}G_{28}C_{21}T_{16}$ |
| *Leptospira borgpetersenii* | $A_{22}G_{26}C_{20}T_{21}$ | $A_{22}G_{25}C_{21}T_{15}$ | $A_{23}G_{26}C_{24}T_{15}$ |
| *Leptospira interrogans* | $A_{22}G_{26}C_{20}T_{21}$ | $A_{22}G_{25}C_{21}T_{15}$ | $A_{23}G_{26}C_{24}T_{15}$ |
| *Mycoplasma genitalium* | $A_{28}G_{23}C_{15}T_{22}$ | **$A_{30}G_{18}C_{15}T_{19}$** | **$A_{24}G_{19}C_{12}T_{18}$** |
| *Mycoplasma pneumoniae* | $A_{28}G_{23}C_{15}T_{22}$ | **$A_{27}G_{19}C_{16}T_{20}$** | **$A_{23}G_{20}C_{14}T_{16}$** |
| *Escherichia coli* | $A_{22}G_{28}C_{20}T_{22}$ | $A_{24}G_{25}C_{21}T_{13}$ | $A_{23}G_{29}C_{22}T_{15}$ |
| *Shigella dysenteriae* | **$A_{22}G_{28}C_{21}T_{21}$** | $A_{24}G_{25}C_{21}T_{13}$ | $A_{23}G_{29}C_{22}T_{15}$ |
| *Proteus vulgaris* | **$A_{23}G_{26}C_{22}T_{21}$** | $A_{26}G_{24}C_{19}T_{14}$ | $A_{24}G_{30}C_{21}T_{15}$ |
| *Yersinia pestis* | $A_{24}G_{25}C_{21}T_{22}$ | $A_{25}G_{24}C_{20}T_{14}$ | $A_{24}G_{30}C_{21}T_{15}$ |
| *Yersinia pseudotuberculosis* | $A_{24}G_{25}C_{21}T_{22}$ | $A_{25}G_{24}C_{20}T_{14}$ | $A_{24}G_{30}C_{21}T_{15}$ |
| *Francisella tularensis* | $A_{20}G_{25}C_{21}T_{23}$ | $A_{23}G_{26}C_{17}T_{17}$ | $A_{24}G_{26}C_{19}T_{19}$ |
| *Rickettsia prowazekii* | **$A_{21}G_{26}C_{24}T_{25}$** | **$A_{24}G_{23}C_{16}T_{19}$** | $A_{26}G_{28}C_{18}T_{18}$ |
| *Rickettsia rickettsii* | $A_{21}G_{26}C_{25}T_{24}$ | $A_{24}G_{24}C_{17}T_{17}$ | $A_{26}G_{28}C_{20}T_{16}$ |

The sequence of *B. anthracis* and *B. cereus* in region 16S_971 is shown below. Shown in bold is the single base difference between the two species which can be detected using the methods of the present invention. *B. anthracis* has an ambiguous base at position 20.

```
B.anthracis_16S_971
GCGAAGAACCUUACCAGGUNUUGACAUCCUCUGACAACCCUAGAGAUAGGGCUUCUCCUUC   (SEQ ID NO: 1)
GGGAGCAGAGUGACAGGUGGUGCAUGGUU
```

```
B.cereus_16S_971
GCGAAGAACCUUACCAGGUCUUGACAUCCUCUGAAAACCCUAGAGAUAGGGCUUCUCCUUC   (SEQ ID NO: 2)
GGGAGCAGAGUGACAGGUGGUGCAUGGUU
```

EXAMPLE 6

ESI-TOF MS of sspE 56-mer Plus Calibrant

Figure 8:
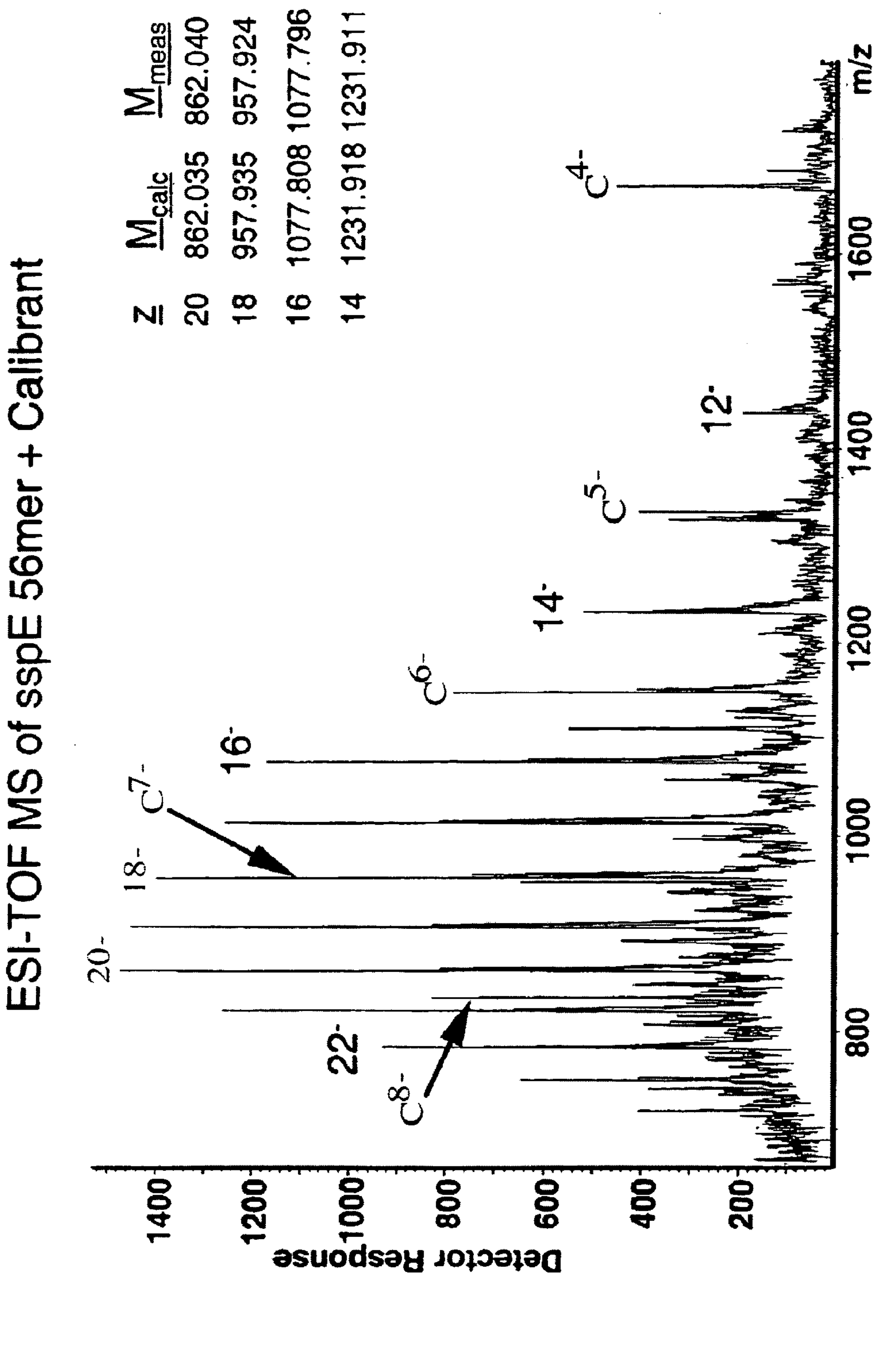
FIG. 8 is an ESI-TOF of *Bacillus anthracis* spore coat protein sspE 56mer plus calibrant. The signals unambiguously identify *B. anthracis* versus other *Bacillus* species.

The mass measurement accuracy that can be obtained using an internal mass standard in the ESI-MS study of PCR products is shown in FIG. 8. The mass standard was a 20-mer phosphorothioate oligonucleotide added to a solution containing a 56-mer PCR product from the *B. anthracis* spore coat protein sspE. The mass of the expected PCR product distinguishes *B. anthracis* from other species of Bacillus such as *B. thuringiensis* and *B. cereus*.

EXAMPLE 7

*B. anthracis* ESI-TOF synthetic 16S_1228 Duplex

Figure 9:
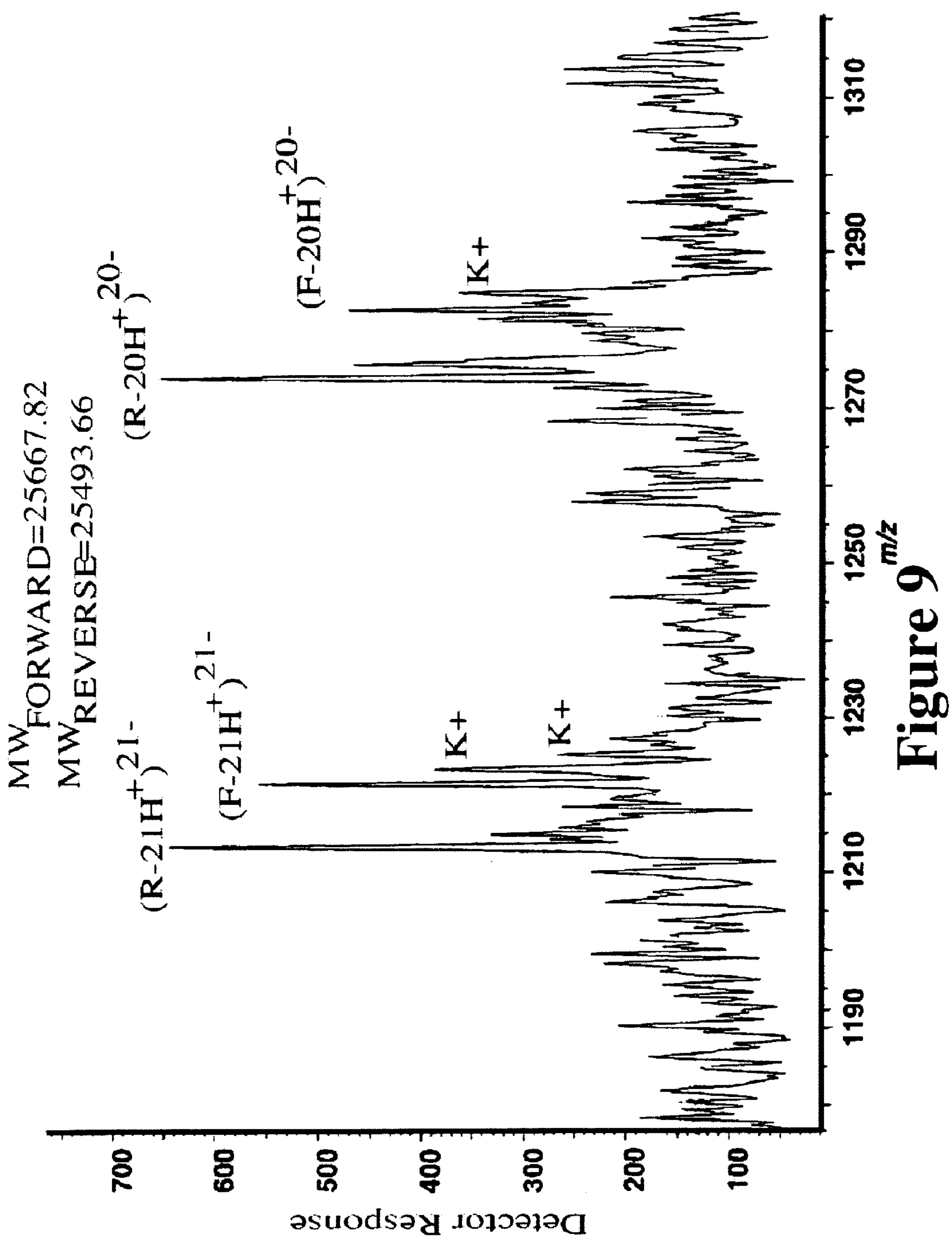
FIG. 9 is an ESI-TOF of a *B. anthracis* synthetic 16S_1228 duplex (reverse and forward strands). The technique easily distinguishes between the forward and reverse strands.

An ESI-TOF MS spectrum was obtained from an aqueous solution containing 5 μM each of synthetic analogs of the expected forward and reverse PCR products from the nucleotide 1228 region of the *B. anthracis* 16S rRNA gene. The results (FIG. 9) show that the molecular weights of the forward and reverse strands can be accurately determined and easily distinguish the two strands. The $[M-21H^+]^{21-}$ and $[M-20H^+]^{20-}$ charge states are shown.

EXAMPLE 8

ESI-FTICR-MS of Synthetic *B. anthracis* 16S_1337 46 Base Pair Duplex

Figure 10:
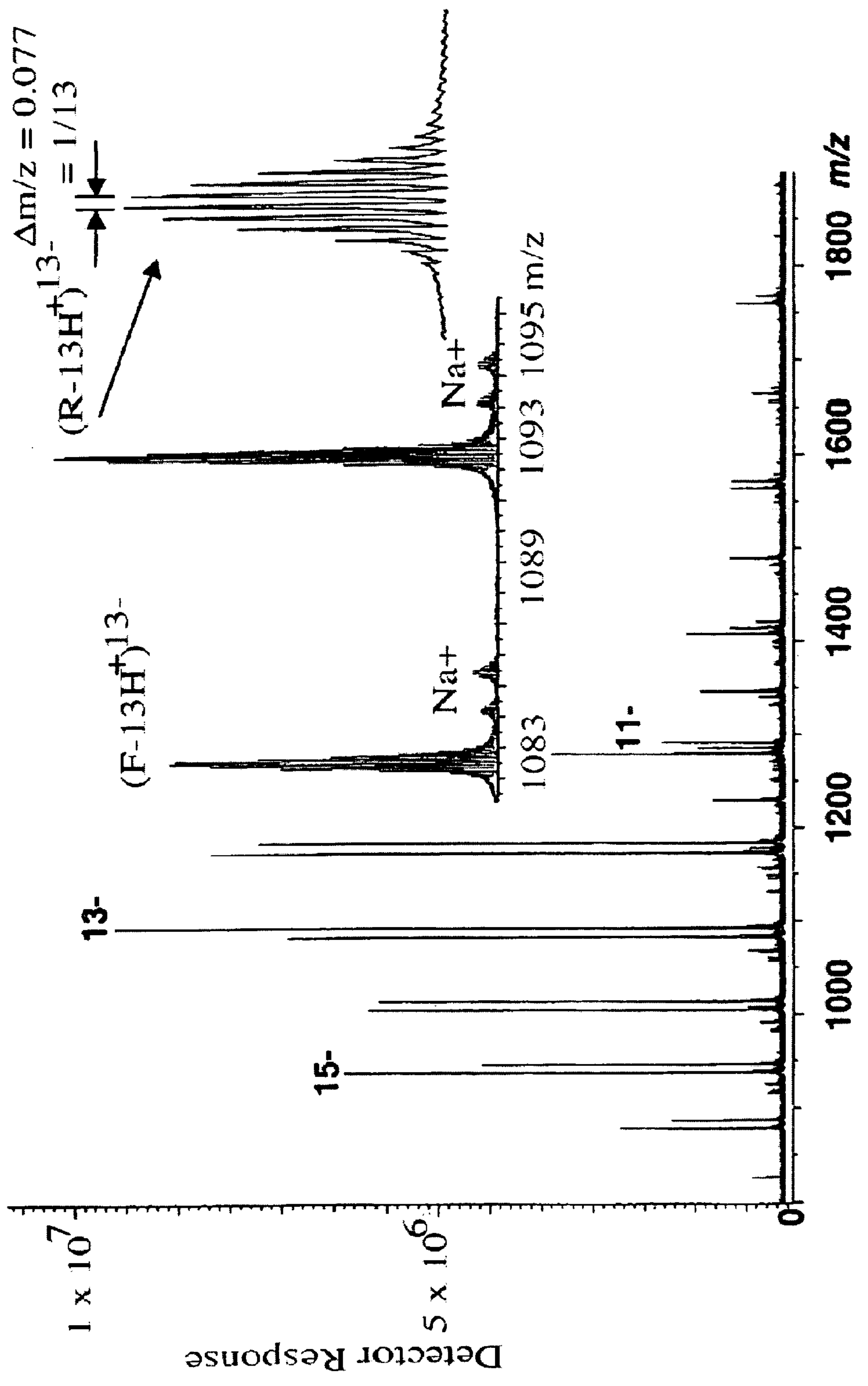
FIG. 10 is an ESI-FTICR-MS of a synthetic *B. anthracis* 16S_1337 46 base pair duplex.

An ESI-FTICR-MS spectrum was obtained from an aqueous solution containing 5 μM each of synthetic analogs of the expected forward and reverse PCR products from the nucleotide 1337 region of the *B. anthracis* 16S rRNA gene. The results (FIG. 10) show that the molecular weights of the strands can be distinguished by this method. The $[M-16H^+]^{16-}$ through $[M-10H^+]^{10-}$ charge states are shown. The insert highlights the resolution that can be realized on the FTICR-MS instrument, which allows the charge state of the ion to be determined from the mass difference between peaks differing by a single 13C substitution.

EXAMPLE 9

Figure 11:
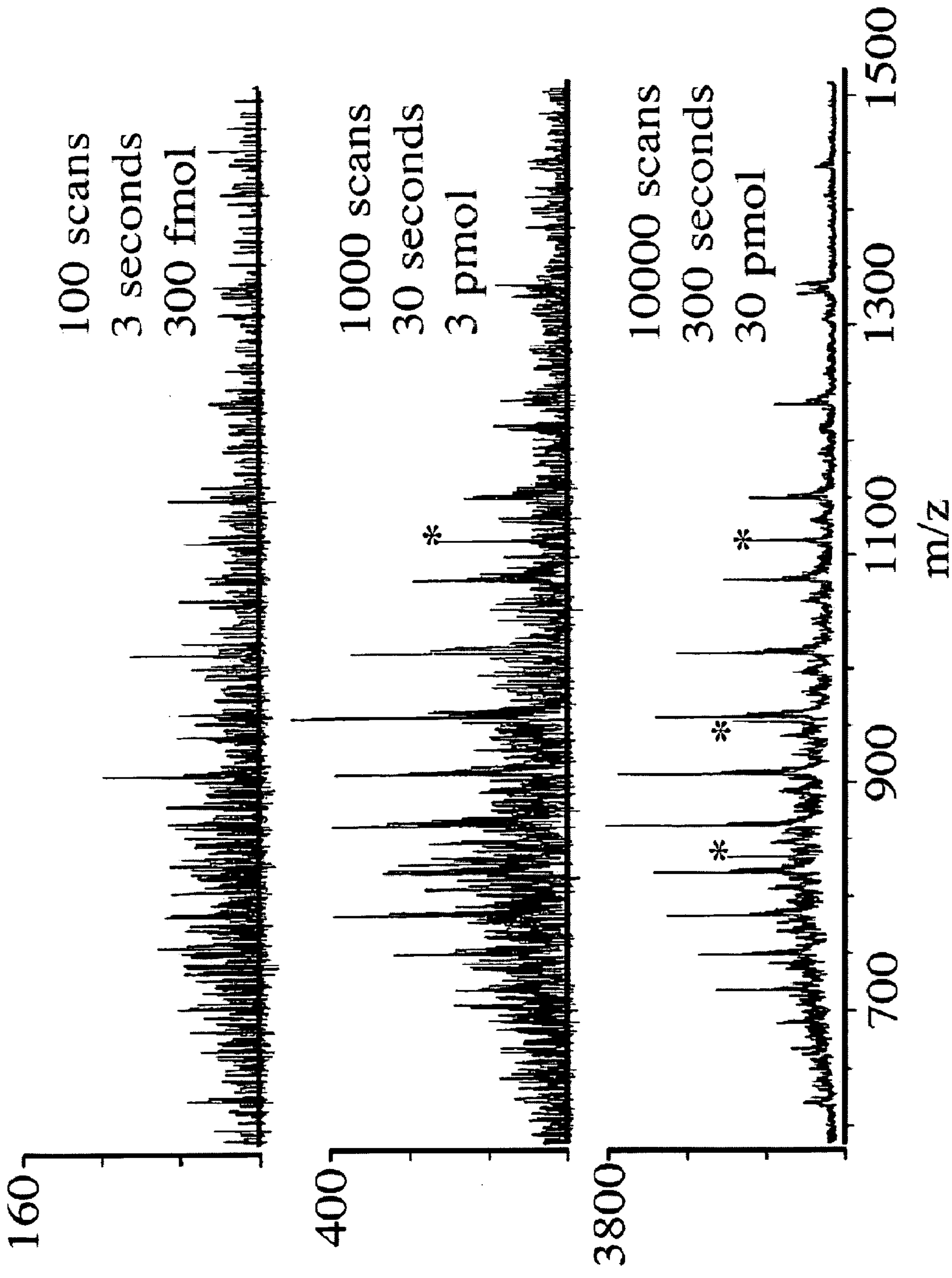
FIG. 11 is an ESI-TOF-MS of a 56mer oligonucleotide (3 scans) from the *B. anthracis* saspB gene with an internal mass standard. The internal mass standards are designated by asterisks.

ESI-TOF MS of 56-mer Oligonucleotide from saspB Gene of *B. anthracis* with Internal Mass Standard ESI-TOF MS spectra were obtained on a synthetic 56-mer oligonucleotide (5 μM) from the saspB gene of *B. anthracis* containing an internal mass standard at an ESI of 1.7 μL/min as a function of sample consumption. The results (FIG. 11) show that the signal to noise is improved as more scans are summed, and that the standard and the product are visible after only 100 scans.

EXAMPLE 10

Figure 12:
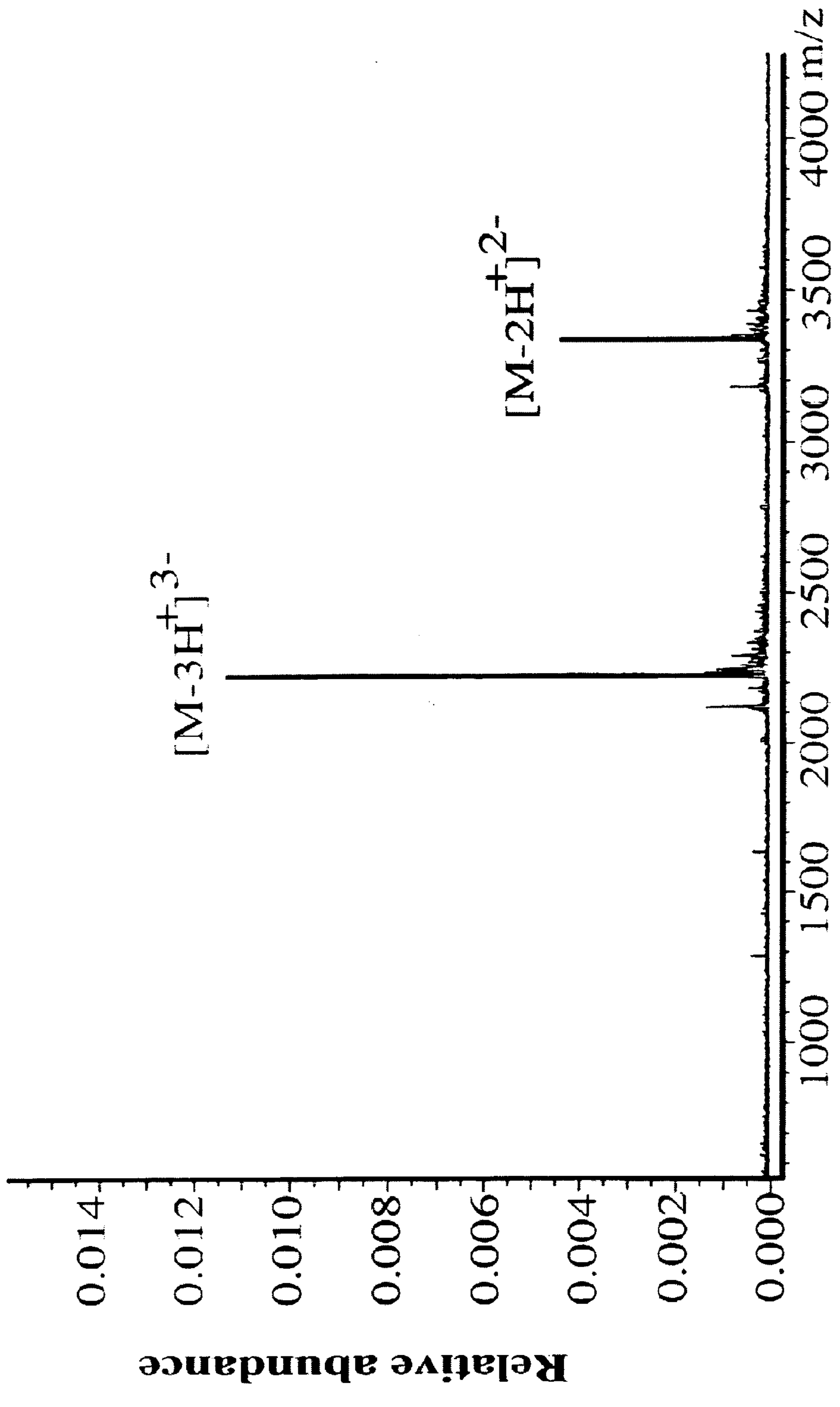
FIG. 12 is an ESI-TOF-MS of an internal standard with 5 mM TBA-TFA buffer showing that charge stripping with tributylammonium trifluoroacetate reduces the most abundant charge state from $[M-8H^+]^{8-}$ to $[M-3H^+]^{3-}$.

ESI-TOF MS of an Internal Standard with Tributylammonium (TBA)-Trifluoroacetate (TFA) Buffer An ESI-TOF-MS spectrum of a 20-mer phosphorothioate mass standard was obtained following addition of 5 mM TBA–TFA buffer to the solution. This buffer strips charge from the oligonucleotide and shifts the most abundant charge state from $[M-8H^+]^{8-}$ to $[M-3H^+]^{3-}$ (FIG. 12).

What is claimed is:

1. A method of identifying a bacterial bioagent comprising:

contacting nucleic acid from the bioagent with at least one pair of primers which hybridize to flanking sequences of the nucleic acid, wherein the flanking sequences flank a variable nucleic acid sequence of the bioagent;

amplifying the variable nucleic acid sequence to produce an amplification product;

determining the molecular mass of the amplification product by mass spectrometry; and comparing the molecular mass of the amplification product to calculated or measured molecular masses of analogous amplification products of one or more known bacterial bioagents present in a database comprising 19 or more molecular masses, with the proviso that sequencing of the amplification product is not used to identify the bacterial bioagent.

2. A method of identifying a bacterial bioagent comprising:

contacting nucleic acid from the bioagent with at least one pair of primers which hybridize to flanking sequences of the nucleic acid, wherein the flanking sequences flank a variable nucleic acid sequence of the bioagent;

amplifying the variable nucleic acid sequence to produce an amplification product;

determining the base composition of the amplification product by mass spectrometry; and comparing the base composition of the amplification product to calculated or measured base composition of analogous amplification products of one or more known bacterial bioagents present in a database comprising 19 or more base compositions, with the proviso that sequencing of the amplification product is not used to identify the bacterial bioagent.

3. The method of claim 1 or claim 2 wherein the amplifying step comprises the polymerase chain reaction.

4. The method of claim 1 or claim 2 wherein the nucleic acid encodes ribosomal RNA or a protein involved in translation, replication, recombination and repair, transcription, nucleotide metabolism, amino acid metabolism, lipid metabolism, energy generation, uptake or secretion.

5. The method of claims 1 or 2 wherein the mass spectrometry is Fourier transform ion cyclotron resonance mass spectrometry (FT-ICR-MS) or time of flight mass spectrometry (TOF-MS).

6. The method of claim 1 or claim 2 wherein the variable nucleic acid sequence exhibits no greater than about 5% identity among bacterial bioagents.

7. The method of claim 1 or claim 2 wherein the sequences to which the primers hybridize are separated by between about 60–100 nucleotides.

8. The method of claim 1 or claim 2 wherein the flanking sequences are between about 80 and 100% identical among bacterial bioagents.

9. The method of claim 1 or claim 2 wherein the flanking sequences are greater than about 95% identical among bacterial bioagents.

10. A method of identifying a bacterial bioagent comprising:

contacting nucleic acid from the bacterial bioagent with at least one pair of primers which hybridize to flanking sequences of the nucleic acid, wherein each member of the pair of primers hybridizes to one hundred or more bacterial bioagents wherein the flanking sequences flank a variable nucleic acid sequence of the one hundred or more bacterial bioagents;

amplifying the variable nucleic acid sequence to produce an amplification product;

determining the molecular mass or base composition of the amplification product by mass spectrometry; and comparing the molecular mass to calculated or measured molecular masses or base compositions of analogous amplification products of more than one known bacterial bioagents, thereby identifying the bacterial bioagent.

11. The method of claim 10 wherein the bacterial bioagent is a member of the genus *Acinetobacter, Aeromonas, Bacillus, Bacteriodes, Bartonella, Bordetella, Borrelia, Brucella, Burkholderia, Campylobacter, Chiamydia, Chiamydophila, Clostridium, Coxiella, Enterococcus, Escherichia, Francisella, Fusobacterium, Haemophilus, Helicobacter, Kiebsiella, Legionella, Leptospira, Listeria, Moraxella, Mycobacterium, Mycoplasma, Neisseria, Proteus, Pseudomonas, Rhodobacter, Rickettsia, Salmonella, Shigella, Staphylococcus, Streptobacillus, Streptomyces, Treponema, Ureaplasma, Vibrio*, or *Yersinia.*

12. The method of claim 10 wherein the amplifying step comprises the polymerase chain reaction.

13. The method of claim 10 wherein the nucleic acid encodes ribosomal RINA or a protein involved in translation, replication, recombination and repair, transcription, nucleotide metabolism, amino acid metabolism, lipid metabolism, energy generation, uptake or secretion.

14. The method of claim 10 wherein the mass spectrometry is Fourier transform ion cyclotron resonance mass spectrometry (FT-ICR-MS) or time of flight mass spectrometry (TOF-MS).

15. The method of claim 10 wherein the molecular masses of the more than one known bacterial bioagents are contained in a database of molecular masses.

16. The method of claim 10 wherein the base compositions of the more than one known bacterial bioagents are contained in a database of base compositions.

17. The method of claim 10 wherein the variable nucleic acid sequence exhibits no greater than about 5% identity among bacterial bioagents.

18. The method of claim 10 wherein the sequences to which the primers hybridize are separated by between about 60–100 nucleotides.

19. The method of claim 10 wherein the flanking sequences are between about 80 and 100% identical among bacterial bioagents.

20. The method of claim 10 wherein the flanking sequences are greater than about 95% identical among bacterial bioagents.

21. The method of claims 1 or 2 wherein the bacterial bioagent is a member of the genus *Acinetobacter, Aeromonas, Bacillus, Bacteriodes, Bartonella, Bordetella, Borrelia, Brucella, Burkholderia, Campylobacter, Chiamydia, Chiamydophila, Clostridium, Coxiella, Enterococcus, Escherichia, Francisella, Fusobacterium, Haemophilus, Helicobacter, Kiebsiella, Legionella, Leptospira, Listeria, Moraxella, Mycobacterium, Mycoplasma, Neisseria, Proteus, Pseudomonas, Rhodobacter, Ricketsia, Salmonella, Shigella, Staphylococcus, Streptobacillus, Streptomyces, Treponema, Ureaplasma, Vibrio*, or *Yersinia.*

22. The method of claims 1, 2 or 10 wherein the bacterial bioagent is identified at the species level.

23. The method of claims 1, 2 or 10 wherein the bacterial bioagent is identified at the strain level.

24. The method of claims 1, 2 or 10 wherein the bacterial bioagent is a biological warfare agent.

25. The method of claim 24 wherein the biological warfare agent is *Bacillus anthracis, Yersinia pestis, Franciscella tularensis, Brucella suis, Brucella abortus, Brucella melitensis, Burkholderia mallei, Burkholderia pseudomalleii, Salmonella typhi, Rickettsia typhii, Rickettsia prowasekii, Coxiella burnetii, Rhodobacter capsulatus, Chlamydia pneumoniae, Escherichia coli, Shigella dysenteriae, Shigellaflexneri, Bacillus cereus, Clostridium botulinum, Coxiella burnetti, Pseudomonas aeruginosa, Legionella pneumophila*, or *Vibrio cholerae.*

26. The method of claims 1, 2 or 10 wherein the pair of primers comprises at least one nucleotide analog.

27. The method of claim 26 wherein the nucleotide analog is inosine, uridine, 2,6-diaminopurine, propyne C, or propyne T.

28. The method of claims 1, 2 or 10 wherein a molecular mass-modifying tag is incorporated into the amplification product to limit the number of possible base compositions consistent with the mass of the amplification product.

29. The method of claim 13 wherein the protein is DNA polymerase, RNA polymerase, elongation factor Tu, heat shock protein groEL, phosphoglycerate kinase, NADH dehydrogenase, DNA ligase, DNA topoisomerase, or elongation factor G.

* * * * *

UNITED STATES PATENT AND TRADEMARK OFFICE

CERTIFICATE OF CORRECTION

PATENT NO. : 7,108,974 B2
APPLICATION NO. : 10/156608
DATED : September 19, 2006
INVENTOR(S) : David J. Ecker et al.

It is certified that error appears in the above-identified patent and that said Letters Patent is hereby corrected as shown below:

1) Column 81, Claim 11, line 7, please delete “Chiamydia, Chiamydophila,” and insert therefore --Chlamydia, Chlamydophila,--;

2) Column 81, Claim 11, lines 9-10, please delete “Kiebsiella,” and insert therefore --Klebsiella,--;

3) Column 81, Claim 13, line 18, please delete “RINA” and insert therefore --RNA--;

4) Column 82, Claim 21, lines 4-5, please delete “Chiamydia, Chiamydophila,” and insert therefore --Chlamydia, Chlamydophila--;

5) Column 82, Claim 21, line 7, please delete “Kiebsiella,” and insert therefore --Klebsiella,--;

6) Column 82, Claim 21, line 9, please delete “Ricketsia,” and insert therefore --Rickettsia,--;

7) Column 82, Claim 25, line 25, please delete “Shigellaflexneri,” and insert therefore --Shigella flexneri,--.

Signed and Sealed this

Twelfth Day of December, 2006

JON W. DUDAS
*Director of the United States Patent and Trademark Office*

US007108974C1

(12) EX PARTE REEXAMINATION CERTIFICATE (7951st)

United States Patent

Ecker et al.

(10) Number: US 7,108,974 C1

(45) Certificate Issued: *Dec. 28, 2010

(54) METHOD FOR RAPID DETECTION AND IDENTIFICATION OF BIOAGENTS

(75) Inventors: David J. Ecker, Encinitas, CA (US); Richard Griffey, Vista, CA (US); Rangarajan Sampath, San Diego, CA (US); Steven Hofstadler, Oceanside, CA (US); John McNeil, La Jolla, CA (US)

(73) Assignee: IBIS Biosciences, Inc., Carlsbad, CA (US)

Reexamination Request:
No. 90/010,210, Jun. 27, 2008

Reexamination Certificate for:

Patent No.: 7,108,974
Issued: Sep. 19, 2006
Appl. No.: 10/156,608
Filed: May 24, 2002

( * ) Notice: This patent is subject to a terminal disclaimer.

Certificate of Correction issued Dec. 12, 2006.

Related U.S. Application Data

(62) Division of application No. 09/798,007, filed on Mar. 2, 2001, now abandoned.

(51) Int. Cl.
*C07H 21/02* (2006.01)
*C12P 19/34* (2006.01)
*C12Q 1/68* (2006.01)

(52) U.S. Cl. .......................... 435/6; 435/91.1; 435/91.2; 536/23.1

(58) Field of Classification Search ........................ None
See application file for complete search history.

(56) References Cited

U.S. PATENT DOCUMENTS 5,436,129 A 7/1995 Stapleton
5,451,500 A 9/1995 Stapleton
5,484,908 A 1/1996 Froehler et al.
5,523,217 A 6/1996 Lupski et al.
5,567,587 A 10/1996 Kohne
5,707,802 A 1/1998 Sandhu et al.
5,727,202 A 3/1998 Kucala
5,745,751 A 4/1998 Nelson et al.
5,759,771 A 6/1998 Tilanus
5,763,169 A 6/1998 Sandhu et al.
5,832,489 A 11/1998 Kucala
5,976,798 A 11/1999 Parker et al.
5,981,190 A 11/1999 Israel
6,001,564 A * 12/1999 Bergeron et al. ............... 435/6
6,018,713 A 1/2000 Coli et al.
6,055,487 A 4/2000 Margery et al.
6,060,246 A 5/2000 Summerton et al.
6,061,686 A 5/2000 Gauvin et al.
6,074,831 A 6/2000 Yakhini et al.
6,180,339 B1 1/2001 Sandhu et al.
6,180,372 B1 1/2001 Franzen
6,194,144 B1 2/2001 Koster
6,221,598 B1 4/2001 Schumm et al.
6,303,297 B1 10/2001 Lincoln et al.
6,322,970 B1 11/2001 Little et al.
6,389,428 B1 5/2002 Rigault et al.
6,393,367 B1 5/2002 Tang et al.
6,419,932 B1 7/2002 Dale
6,453,244 B1 9/2002 Oefner
6,468,743 B1 10/2002 Romick et al.
6,475,143 B2 11/2002 Iliff
6,553,317 B1 4/2003 Lincoln et al.
6,605,433 B1 8/2003 Fliss et al.
6,613,520 B2 9/2003 Ashby et al.
6,680,476 B1 1/2004 Hidalgo et al.
6,716,634 B1 4/2004 Myerson
7,108,974 B2 9/2006 Ecker et al.
7,217,510 B2 5/2007 Ecker et al.
7,226,739 B2 6/2007 Ecker et al.
7,255,992 B2 8/2007 Ecker et al.
2002/0138210 A1 9/2002 Wilkes et al.
2002/0168630 A1 11/2002 Fleming et al.
2003/0027135 A1 2/2003 Ecker et al.
2003/0124556 A1 7/2003 Ecker et al.
2003/0175695 A1 9/2003 Ecker et al.
2003/0175696 A1 9/2003 Ecker et al.
2003/0175697 A1 9/2003 Ecker et al.
2003/0190605 A1 10/2003 Ecker et al.
2004/0081993 A1 4/2004 Cantor et al.
2004/0110169 A1 6/2004 Ecker et al.
2004/0161770 A1 8/2004 Ecker et al.
2004/0180328 A1 9/2004 Ecker et al.
2004/0202997 A1 10/2004 Ecker et al.
2004/0219517 A1 11/2004 Ecker et al.
2006/0057605 A1 3/2006 Sampath et al.
2006/0121520 A1 6/2006 Ecker et al.
2006/0275788 A1 12/2006 Ecker et al.

FOREIGN PATENT DOCUMENTS

EP 0620862 4/1998
WO WO 92/08117 5/1992
WO 1992009703 A1 6/1992
WO WO 93/08297 4/1993
WO WO 95/04161 2/1995
WO WO 95/13396 5/1995
WO 1996035450 A1 11/1996
WO WO 99/12040 3/1999
WO WO 01/57518 8/2001
WO WO 01/73199 10/2001
WO WO 02/10444 2/2002

(Continued)

OTHER PUBLICATIONS

Muddiman et al (Anal. Chem. 1997, vol. 69 pp. 1543–1549).*

(Continued)

*Primary Examiner*—Padmashri Ponnaluri

(57) ABSTRACT

Method for detecting and identifying unknown bioagents, including bacteria, viruses and the like, by a combination of nucleic acid amplification and molecular weight determination using primers which hybridize to conserved sequence regions of nucleic acids derived from a bioagent and which bracket variable sequence regions that uniquely identify the bioagent. The result is a "base composition signature" (BCS) which is then matched against a database of base composition signatures, by which the bioagent is identified.

FOREIGN PATENT DOCUMENTS

| | | |
|---|---|---|
| WO | WO 02/22873 | 3/2002 |
| WO | WO 02/070664 | 9/2002 |
| WO | WO 03/093506 | 11/2003 |
| WO | WO 2003/102191 | 12/2003 |
| WO | WO 2004/013357 | 2/2004 |
| WO | WO 2004/052175 | 6/2004 |
| WO | WO 2005/053141 | 6/2005 |
| WO | 2007086904 | 8/2007 |

OTHER PUBLICATIONS

GenBank accession No. AE009948.1 (gi:22535226; Aug. 8, 2002).

GenBank accession No. AE009949.1 (gi:19913450; Apr. 3, 2002).

GenBank accession No. AE015927.1 (gi:28204652; Feb. 4, 2003).

GenBank accession No. AE015929.1 (gi:27316888; Jan. 2, 2003.

GenBank accession No. AF274728 (gi:11612419; Dec. 11, 2000).

GenBank accession No. AF276257.1 (gi:1457889; Jul. 1, 2001).

GenBank Accession No. BX571857.1 (gi:49243355; Jun. 25, 2004).

Barbour et al., "Identification of an uncultivatable Borrelia species in the hard tick Amblyommaamericanum: Possible agent of a Lyme disease–like illness"; The Journal of Infectious Diseases; 1996; pp. 403–409; vol. 173.

James et al., "Borelia Ionestari infection after a bite by an Amblyomma americanum tick" The Journal of Infectious Diseases; 2001; pp. 1810–1814; vol. 183.

Olsen et al., "Transhemispheric exchange of Lyme disease spyrochetes by seabirds" Journal of Clinical Microbiology; 1995; pp. 3270–3274; vol. 33.

Sampath et al., "Global surveillance of emerging influenza virus genotypes by mass spectrometry" Plos One; 2007; 5:e489.

Sampath et al., "Rapid Identification of Emerging Infectious Agents Using PCRand Electrospray Ionization Mass Spectrometry", Ann. N.Y. Acad. Sci., 2007, pp. 109–120; vol. 1102.

Schabereiter–Gurtner et al., "Application of broad–range 16s rRNA PCR amplification andDGGE fingerprinting for detection of tick–infecting bacteria", The Journal of Microbiological Methods, 2003, pp. 251–260, vol. 52.

Sumner et al., "PCR Amplification and Comparison of Nucleotide Sequencesfrom the groESL Heat Shock Operon of Ehrlichia Species", Journal of Critical Microbiology, 1997, pp. 2087–2092, vol. 35.

U.S. Appl. No. 10/943,344 Office Communication Mailed Oct. 14, 2009 (DIBIS–0041US2P1).

Barns et al., "Detection of diverse new Francisella–like bacteria in environmental samples," Applied and Environmental Microbiology (2005) 71:5494–5500.

De la Puente–Redondo et al., "Comparison of different PCR approaches for typing of *Francisella tularensis* strains." (2000) 38:1016–1022.

Del Blanco et al., "Genotyping of *Francisella tularensis* strains by pulsed–field gel electrophoresis, amplified fragment length polymorphism fingerprinting, and 16S rRNA gene sequencing." (2002) 40:2964–2972.

Farlow et al., "*Francisella tularensis* Strain Typing Using Multiple–Locus, Variable–Number Tandem Repeat Analysis" Journal of Critical Microbiology, (2001) 39(9):3186–3192.

International Search Report for PCT/US2009/045635 dated Oct. 7, 2009 (DIBIS–0109WO).

Johansson et al., "Evaluation of PCR–based methods for discrimination of *Francisella* species and subspecies and development of a specific PCR that distinguishes the two major subspecies of *Francisella tularensis*." Journal of Clinical Microbiology (2000) 38:4180–4185.

U.S. Appl. No. 90/010, 209, Re–exam, Jun. 27, 2008, Ecker et al.

Alves–Silva, J. et al., "The Ancestry of Brazilian mtDNA Lineages," *Am. J. Hum. Genet.* (2000) 67:444–461.

Anderson et al., "Sequence and organization of the human mitochondrial genome," *Nature* (1981) 290:457–465.

Andreasson et al., "Mitochondrial Sequence Analysis for Forensic Identification Using Pyrosequencing Technology" *BioTechniques* (2002) 32:124–133.

Crespillo et al., "Mitochondrial DNA sequences for 118 individuals from northeastern Spain" *Int. J. Legal Med.* (2000) 114:130–132.

Dias Neto et al., "Shotgun sequencing of the human transcriptome with ORF expressed sequence tags" *PNAs* (2000) 97:3491–3496.

Elnifro et al., "PCR and Restriction Endonuclease Analysis for Rapid Identification of Adenovirus Subgenera" *Journal of Clinical Microbiology* (2000) 38:2055–2061.

EMBL Accession No. S90302, Human, Muscle, Mitochondrial Mutant, 22 nt, segment 2 of 2 (XP002436791) Nov. 26, 1993.

Esmans et al., "Liquid Chromatograpy–Mass Spectrometry in Nucleoside, nucleotide and modified nucleotide characterization" *J. of Chromatography A* (1998) 794:109–127.

Fraser et al., "The Minimal Gene Complement of Mycoplasma Genitalium" *Science* (1995) 270:397–403.

Fuerstenau et al., "Molecular Weight Determination of Megadalton DNA Electrospray Ions Using Charge Detection Time–of–flight Mass Spectrometry" *Rapid Comm. Mass Spec.* (1995) 9:1528–1538.

Fujioka et al., "Analysis of enterovirus genotypes using single–strand conformation polymorphisms of polymerase chain reaction products" *J. Virol. Meth.* (1995) 51:253–258.

Gabriel et al., "Improved MtDNA sequence analysis of forensic remains using a "mini–primer set" amplification strategy" *Journal of Forensic Sciences* (2001) 46:247–253.

Gattermann et al., "Heteroplasmic Point Mutations of Mitochondrial DNA Affecting Subunit I of Cytochrome c Oxidase in Two Patients with Acquired Idiopathic Sideroblastic Anemia" *Blood* (1997) 90:4961–4972.

Gendel et al., "Computational analysis of the specificity of 16S rRNA–derived signature sequences for identifying food–related microbes" Food Microbiology (1996) 13:1–15.

Ginther et al., "Identifying individuals by sequencing mitochondrial DNA from teeth," *Nature Genetics* (1992) 2:135–138.

Giles et al., "Maternal inheritance of human mitochondrial DNA," *PNAS* (1980) 77:6715–6719.

Goto et al., "Applications of the partial 16S rDNA seqeunce as an index for rapid identification of species in the genus *Bacillus*" *J. Gen. Appl. Microbiol.* (2000) 46:1–8.

Greenberg et al., "Intraspecific nucleotide sequence variability surrounding the origin of replication in human mitochondrial DNA," *Gene* (1983) 21:33–49.

Grzybowski "Extremely high levels of human mitochondrial DNA heteroplasmy in single hair roots" *Electrophoresis* (2000) 21:548–553.

Haugland et al., "Identification of putative sequence specific PCR primers for detection of the toxigenic fungal species Stachybotrys chartarum" *Mol. Cell. Probes* (1998) 12:387–396.

Holland et al., "Mitochondrial DNA Sequence Analysis of Human Skeletal Remains: Identification of Remains from the Vietnam War," *Journal of Forensic Sciences* (1993) 38:542–553.

Holm et al., "Removing near–neighbour redundancy from large protein sequence collections" *Bioinformatics* (1998) 14:423–429.

Howell et al., "Persistent Heteroplasmy of a Mutation in the Human mtDNA Control Region: Hypermutation as an Apparent Consequence of Simple–Repeat Expansion/Contraction" *Am. J. Hum. Genet.* (2000) 66:1589–1598.

Hutchison et al., "Maternal inheritance of mammalian mitochondrial DNA," *Nature* (1974) 251:536–538.

Ingman et al., "Mitochondrial genome variation and the origin of modern humans" *Nature* (2000) 408:708–713.

Jackson et al., "Mass spectrometry for genotyping: an emerging tool for molecular medicine" Molecular Medicine Today (2000) 6:271–276.

Jansen et al., "Genotype–by–environment Interaction in Genetic Mapping of Multiple Quantitative Trait Loci" *Theor. Appl. Genet.* (1995) 91:33–37.

Jensen et al., "Rapid Identification of Bacteria on the Basis of Polymerase Chain Reaction–Amplified Ribosomal DNA Spacer Polymorphisms" *Appl. Environ. Microbiol.* (1993) 59:945–952.

Jiang et al., "Multiple Trait Analysis of Genetic Mapping for Quantitative Trait Loci Genetics" *Genetics* (1995) 140:1111–1127.

Jiang et al., "A highly efficient and automated method of purifying and desalting PCR products for analysis by electrospray ionization mass spectrometry." *Anal. Biochem.* (2003) 316:50–57.

Jurinke et al., "Detection of hepatitis B virus DNA in serum samples via nested PCR and MALDI–TOF mass spectrometry" *Genetic Analysis: Biomolecular Engineering* (1996) 13:67–71.

Ke et al., "Development of a PCR Assay for Rapid Detection of Enterococci" *Journal of Clinical Microbiology* (1999) 37:3497–3503.

Keller et al., "Empirical Statistical Model To Estimate the Accuracy of Peptide Identifications Made by MS/MS and Database Search" *Anal. Chem* (2002) 74:5383–5392.

Kilpatrick et al., "Group–Specific Identification of Polioviruses by PCR Using Primer Containing Mixed–Base or Deoxyinosine Residues at Positions of Codon Degeneracy" *J. Clin. Microbiol.* (1996) 34:2990–2996.

Kupke et al., "Molecular Characterization of Lantibiotic–synthesizing Enzyme EpiD Reveals a Function for Bacterial Dfp Proteins i Coenzyme A Biosynthesis" *Journal of Biological Chemistry* (2000) 275:31838–31846.

Lebedev, Y. et al "Oligonucleotides containing 2–aminoadenine and 5–methycytosine are more effective as primers for PCR amplification than their nonmodified counterparts" Genetic Analysis: Biomolecular Engineering (1996) 13:15–21.

Leif et al., "Isolation and characterization of the proton–translocating NADH: ubiquinone oxidoreductase from *Escherichia coli" Eur. J. Biochem.* (1995) 230:538–548.

Lewers et al., "Detection of Linked QTL for Soybean Brown Stem Rot Resistance in 'BSR 101' as Expressed in a Growth Chamber Environment" *Molecular Breeding* (1999) 5:33–42.

Little et al., "Maldi on a Chip: Analysis of Arrays of Low–Femtomole to Subfemtomole Quantities of Synthetic Oligonucleotides and DNA Diagnostic Products Dispensed by a Piezoelectric Pipet" *Analytical Chemistry* (1997) 69:4540–4546.

Matray et al., "Synthesis and properties of RNA analogs—oligoribonucleotide N3'–>P5' phosphoramidates" *Nucleic Acids Res* (1999) 3976–3985.

McLafferty et al., "Comparison of Algorithms and Databases for Matching Unknown Mass Spectra" *J. Am. Soc. Mass Spectrom.* (1998).

Miller et al., "A compendium of human mitochondrial DNA control region: development of an international standard forensic database," Croat Med. J. (2001) 42:315–327.

Nakao et al., "Development of a Direct PCR Assay for Detection of the Diphtheria Toxin Gene" *J. Clin. Microbiol.* (1997) 35:1651–1655.

Nilsson et al., "Evaluation of mitochondrial DNA coding region assays for increased discrimination in forensic Analysis" *Forensic Science International: Genetics* (2008) 2:1–8.

Nishikaw et al., "Reconstitution of active recombinant Shiga toxin (Stx)1 from recombinant Stxl–A and Stxl–B subunits independently produced by *E. coli* clones"*FEMS* (1999) 178:13–18.

Norder et al., "Typing of Hepatitis B Virus Genomes by a Simplified Polymerase Chain Reaction" *J. Med. Virol.* (1990) 31:215–221.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom.* (2003) 17:1714–1722.

Null et al., "Implications of hydrophobicity and free energy of solvation for characterization of nucleic acids by electrospray ionization mass spectrometry" *Anal. Chem.* (2003) 75:1331–1339.

Parson et al., "Population data for 101 Austrian Caucasian mitochondrial DNA d–loop sequences: Application of mtDNA sequence analysis to a forensic case" *Int. J. Legal Med.* (1998) 111:124–132.

Paterson et al., "Fine Mapping of Quantitative Trait Loci Using Selected Overlapping Recombinant Chromosomes, in an Interspecies Cross of Tomato" *Genetics* (1990) 124:735–742.

Raaum, R. L. et al., "Catarrhine primate divergence dates estimated from complete mitochondrial genomes: concordance with fossil and nuclear DNA evidence," *J. Hum. Evol.* (2005) 48:237–257.

Scaramozzino et al., "Comparison of Flavivirus universal primer pairs and development of a rapid, highly sensitive heminested reverse transcription–PCR assay for detection of flaviviruses targeted to a conserved region of the NS5 gene sequences" *J. Clin. Microbiol.* (2001) 39:1922–1927.

Schena M. "Genome analysis with gene expression microarrays" Bioessays (1996) 18:427–431.

Senko et al., "Determination of Monoisotopic Masses and Ion Populations for Large Biomolecules from Resolved Isotopic Distributions," *J. Am. Soc. Mass Spectrom.* (1995) 6:229.

Stoneking et al., "Population variation of human mDNA control region sequences detected by enzymatic amplification and sequence–specific oligonucleotide probes," American Journal of Human Genetics (1991) 48:370–382.

Takeuchi et al., "Serotyping of Adenoviruses on Conjunctival Scrapings by PCR and Sequence Analysis" *Journal of Clinical Microbiology* (1999) 37:1839–1845.

Tatuch et al., "Heteroplasmic mtDNA mutation (T–G) at 8993 can cause Leigh disease when the percentage of abnormal mtDNA is high" *Am. J. Hum. Genet.* (1992) 50:852–858.

Torroni et al., "Classification of European mtDNAs from an Analysis of Three European Populations" *Genetics* (1996) 144:1835–1850.

Van Der Vossen et al., "DNA based typing, identification and detection systems for food spoilage microorganisms: development and implementation" *Int. J. Food Microbiol.* (1996) 33:35–49.

Vanderhallen et al., "Identification of Encephalomyocarditis Virus in Clinical Samples by Reverse Transcription–PCR Followed by Genetic Typing Using Sequence Analysis" *J. Clin. Microbiol.* (1998) 36:3463–3467.

Welham et al., "The Characterization of Micro–organisms by Matrix–assisted Laser Desorption/Ionization Time–of–flight Mass Spectrometry" *Rapid Communications in Mass Spectrometry* (1998) 12:176–180.

Yao et al., "Mass Spectrometry Based Proteolytic Mapping for Rapid Virus Detection" *Anal. Chem.* (2002) 74:2529–2534.

Zeng et al., "Precision Mapping of Quantitative Trait Loci" *Genetics* (1994) 136:1457–1468.

European Application No. EP 02709785.2 filed Sep. 12, 2002, Isis Pharma.

Chinese Application No. 1202204 filed Dec. 16, 1998, Sequenom.

Yevette A. Johnson, et al., "Precise molecular weight determination of PCR products of the rRNA intergenic spacer region using electrospray quadrupole mass spectrometry for differentiation of B. subtilis and B. altrophaeus, closely related species of bacilli",. J. Microbiological Methods, 40:241–245 (2000) (the Johnson reference).

Aaserud, D.J., et al., "Accurate Base Composition of Double–Strand DNA by Mass Spectrometry", Amer.Soc. For Mass Spectrometry, 1266–1269 (1996) (the Aaserud reference).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-29 are cancelled.

New claims 30-45 are added and determined to be patentable.

*30. A method of identifying a bacterial bioagent comprising:*

*contacting nucleic acid from the bioagent with at least one pair of primers which hybridize to conserved flanking sequences of the nucleic acid shared among at least nineteen bioagents, wherein the flanking sequences flank a target sequence region variable nucleic acid sequence of the bioagent that varies between at least nineteen bioagents;*

*amplifying the target variable nucleic acid sequence to produce an amplification product;*

*determining the molecular mass of the amplification product by mass spectrometry; determining the base composition of said amplification product from said molecular mass; and comparing the base composition of the amplification product to calculated or measured base compositions of analogous amplification products of one or more known bacterial bioagents present in a database comprising 19 or more calculated base compositions, said comparing comprising interrogating a database, wherein said interrogating comprises comparison of the determined base composition with the database; said database comprises base compositions calculated for the target variable sequence regions for at least said nineteen bioagents and each of the calculated base compositions is indexed to bioagent characterizing information; delivering from the database a response that comprises the bioagent characterization information generated by the comparison of the measured and calculated base composition thereby identifying the bioagent associated with amplification product with the proviso that sequencing of the amplification product is not used to identify the bacterial bioagent.*

*31. The method of claim 30, wherein the amplifying step comprises the polymerase chain reaction.*

*32. The method of claim 30 wherein the nucleic acid encodes ribosomal RNA or a protein involved in translation, replication, recombination and repair, transcription, nucleotide metabolism, amino acid metabolism, lipid metabolism, energy generation, uptake or secretion.*

*33. The method of claims 30 wherein the mass spectrometry is Fourier transform ion cyclotron resonance mass spectrometry (FT-ICR-MS) or time of flight mass spectrometry (TOF-MS).*

*34. The method of claim 30 wherein the variable nucleic acid sequence exhibits no greater than about 5% identity among bacterial bioagents.*

*35. The method of claim 30 wherein the sequences to which the primers hybridize are separated by between about 60-100 nucleotides.*

*36. The method of claim 30 wherein the flanking sequences are between about 80 and 100% identical among bacterial bioagents.*

*37. The method of claim 30 wherein the flanking sequences are greater than about 95% identical among bacterial bioagents.*

*38. The method of claim 30 wherein the bacterial bioagent is a member of the genus Acinetobacter, Aeromonas, Bacillus, Bacteriodes, Bartonella, Bordetella, Borrelia, Brucella, Burkholderia, Campylobacter, Chiamydia, Chiamydophila, Clostridium, Coxiella, Enterococcus, Escherichia, Francisella, Fusobacterium, Haemophilus, Helicobacter, Kiebsiella, Legionella, Leptospira, Listeria, Moraxella, Mycobacterium, Mycoplasma, Neisseria, Proteus, Pseudomonas, Rhodobacter, Ricketsia, Salmonella, Shigella, Staphylococcus, Streptobacillus, Streptomyces, Treponema, Ureaplasma, Vibrio, or Yersinia.*

*39. The method of claims 30 wherein the bacterial bioagent is identified at the species level.*

*40. The method of claims 30 wherein the bacterial bioagent is identified at the strain level.*

*41. The method of claims 30 wherein the bacterial bioagent is a biological warfare agent.*

*42. The method of claim 41 wherein the biological warfare agent is Bacillus anthracis, Yersinia pestis, Franciscella tularensis, Brucella suis, Brucella abortus, Brucella melitensis, Burkholderia mallei, Burkholderia pseudomalleii, Salmonella typhi, Rickettsia typhii, Rickettsia prowasekii, Coxiella burnetti, Rhodobacter capsulatus, Chlamydia pneumoniae, Escherichia coli, Shigella dysenteriae, Shigellaflexneri, Bacillus cereus, Clostridium botulinum, Coxiella burnetti, Pseudomonas aeruginosa, Legionella pneumophila, or Vibrio cholerae.*

*43. The method of claim 30 wherein the pair of primers comprises at least one nucleotide analog.*

*44. The method of claim 43 wherein the nucleotide analog is inosine, uridine, 2,6-diaminopurine, propyne C, or propyne T.*

*45. The method of claim 30 wherein a molecular mass-modifying tag is incorporated into the amplification product to limit the number of possible base compositions consistent with the mass of the amplification product.*

* * * * *

SEQUENCE LISTING

<160> NUMBER OF SEQ ID NOS: 7

<210> SEQ ID NO 1
<211> LENGTH: 90
<212> TYPE: RNA
<213> ORGANISM: Bacillus anthracis
<220> FEATURE:
<221> NAME/KEY: misc_feature
<222> LOCATION: (20)..(20)
<223> OTHER INFORMATION: N = A, U, G or C

<400> SEQUENCE: 1
gcgaagaacc uuaccaggun uugacauccu cugacaaccc uagagauagg gcuucuccuu 60
cgggagcaga gugacaggug gugcaugguu 90

<210> SEQ ID NO 2
<211> LENGTH: 90
<212> TYPE: RNA
<213> ORGANISM: Bacillus cereus

<400> SEQUENCE: 2
gcgaagaacc uuaccagguc uugacauccu cugaaaaccc uagagauagg gcuucuccuu 60
cgggagcaga gugacaggug gugcaugguu 90

<210> SEQ ID NO 3
<211> LENGTH: 1542
<212> TYPE: RNA
<213> ORGANISM: Artificial Sequence
<220> FEATURE:
<221> NAME/KEY: misc_feature
<223> OTHER INFORMATION: 16S rRNA consensus sequence
<221> NAME/KEY: misc_feature
<222> LOCATION: (1)..(7)
<223> OTHER INFORMATION: N= A, U, G or C
<221> NAME/KEY: misc_feature
<222> LOCATION: (19)..(19)
<223> OTHER INFORMATION: N= A, U, G or C
<221> NAME/KEY: misc_feature
<222> LOCATION: (28)..(30)
<223> OTHER INFORMATION: N= A, U, G or C
<221> NAME/KEY: misc_feature
<222> LOCATION: (43)..(45)
<223> OTHER INFORMATION: N= A, U, G or C
<221> NAME/KEY: misc_feature
<222> LOCATION: (48)..(48)
<223> OTHER INFORMATION: N= A, U, G or C
<221> NAME/KEY: misc_feature
<222> LOCATION: (50)..(50)
<223> OTHER INFORMATION: N= A, U, G or C
<221> NAME/KEY: misc_feature
<222> LOCATION: (52)..(52)
<223> OTHER INFORMATION: N= A, U, G or C
<221> NAME/KEY: misc_feature
<222> LOCATION: (66)..(66)
<223> OTHER INFORMATION: N= A, U, G or C
<221> NAME/KEY: misc_feature
<222> LOCATION: (69)..(69)
<223> OTHER INFORMATION: N= A, U, G or C
<221> NAME/KEY: misc_feature
<222> LOCATION: (100)..(100)
<223> OTHER INFORMATION: N= A, U, G or C
<221> NAME/KEY: misc_feature
<222> LOCATION: (103)..(103)
<223> OTHER INFORMATION: N= A, U, G or C
<221> NAME/KEY: misc_feature
<222> LOCATION: (107)..(108)
<223> OTHER INFORMATION: N= A, U, G or C
<221> NAME/KEY: misc_feature
<222> LOCATION: (121)..(122)
<223> OTHER INFORMATION: N= A, U, G or C -continued
<221> NAME/KEY: misc_feature
<222> LOCATION: (124)..(124)
<223> OTHER INFORMATION: N= A, U, G or C
<221> NAME/KEY: misc_feature
<222> LOCATION: (126)..(129)
<223> OTHER INFORMATION: N= A, U, G or C
<221> NAME/KEY: misc_feature
<222> LOCATION: (131)..(132)
<223> OTHER INFORMATION: N= A, U, G or C
<221> NAME/KEY: misc_feature
<222> LOCATION: (134)..(134)
<223> OTHER INFORMATION: N= A, U, G or C
<221> NAME/KEY: misc_feature
<222> LOCATION: (137)..(145)
<223> OTHER INFORMATION: N= A, U, G or C
<221> NAME/KEY: misc_feature
<222> LOCATION: (148)..(148)
<223> OTHER INFORMATION: N= A, U, G or C
<221> NAME/KEY: misc_feature
<222> LOCATION: (150)..(150)
<223> OTHER INFORMATION: N= A, U, G or C
<221> NAME/KEY: misc_feature
<222> LOCATION: (152)..(158)
<223> OTHER INFORMATION: N= A, U, G or C
<221> NAME/KEY: misc_feature
<222> LOCATION: (163)..(169)
<223> OTHER INFORMATION: N= A, U, G or C
<221> NAME/KEY: misc_feature
<222> LOCATION: (177)..(178)
<223> OTHER INFORMATION: N= A, U, G or C
<221> NAME/KEY: misc_feature
<222> LOCATION: (181)..(194)
<223> OTHER INFORMATION: N= A, U, G or C
<221> NAME/KEY: misc_feature
<222> LOCATION: (199)..(226)
<223> OTHER INFORMATION: N= A, U, G or C
<221> NAME/KEY: misc_feature
<222> LOCATION: (229)..(237)
<223> OTHER INFORMATION: N= A, U, G or C
<221> NAME/KEY: misc_feature
<222> LOCATION: (239)..(242)
<223> OTHER INFORMATION: N= A, U, G or C
<221> NAME/KEY: misc_feature
<222> LOCATION: (245)..(245)
<223> OTHER INFORMATION: N= A, U, G or C
<221> NAME/KEY: misc_feature
<222> LOCATION: (248)..(248)
<223> OTHER INFORMATION: N= A, U, G or C
<221> NAME/KEY: misc_feature
<222> LOCATION: (250)..(250)
<223> OTHER INFORMATION: N= A, U, G or C
<221> NAME/KEY: misc_feature
<222> LOCATION: (257)..(258)
<223> OTHER INFORMATION: N= A, U, G or C
<221> NAME/KEY: misc_feature
<222> LOCATION: (264)..(264)
<223> OTHER INFORMATION: N= A, U, G or C
<221> NAME/KEY: misc_feature
<222> LOCATION: (268)..(269)
<223> OTHER INFORMATION: N= A, U, G or C
<221> NAME/KEY: misc_feature
<222> LOCATION: (276)..(276)
<223> OTHER INFORMATION: N= A, U, G or C
<221> NAME/KEY: misc_feature
<222> LOCATION: (278)..(280)
<223> OTHER INFORMATION: N= A, U, G or C
<221> NAME/KEY: misc_feature
<222> LOCATION: (283)..(286)
<223> OTHER INFORMATION: N= A, U, G or C
<221> NAME/KEY: misc_feature
<222> LOCATION: (291)..(291)
<223> OTHER INFORMATION: N= A, U, G or C
<221> NAME/KEY: misc_feature
<222> LOCATION: (293)..(294)
<223> OTHER INFORMATION: N= A, U, G or C
<221> NAME/KEY: misc_feature
<222> LOCATION: (303)..(304)
<223> OTHER INFORMATION: N= A, U, G or C
<221> NAME/KEY: misc_feature -continued
<222> LOCATION: (306)..(307)
<223> OTHER INFORMATION: N= A, U, G or C
<221> NAME/KEY: misc_feature
<222> LOCATION: (309)..(309)
<223> OTHER INFORMATION: N= A, U, G or C
<221> NAME/KEY: misc_feature
<222> LOCATION: (316)..(316)
<223> OTHER INFORMATION: N= A, U, G or C
<221> NAME/KEY: misc_feature
<222> LOCATION: (320)..(320)
<223> OTHER INFORMATION: N= A, U, G or C
<221> NAME/KEY: misc_feature
<222> LOCATION: (328)..(328)
<223> OTHER INFORMATION: N= A, U, G or C
<221> NAME/KEY: misc_feature
<222> LOCATION: (333)..(333)
<223> OTHER INFORMATION: N= A, U, G or C
<221> NAME/KEY: misc_feature
<222> LOCATION: (337)..(337)
<223> OTHER INFORMATION: N= A, U, G or C
<221> NAME/KEY: misc_feature
<222> LOCATION: (359)..(360)
<223> OTHER INFORMATION: N= A, U, G or C
<221> NAME/KEY: misc_feature
<222> LOCATION: (366)..(366)
<223> OTHER INFORMATION: N= A, U, G or C
<221> NAME/KEY: misc_feature
<222> LOCATION: (369)..(371)
<223> OTHER INFORMATION: N= A, U, G or C
<221> NAME/KEY: misc_feature
<222> LOCATION: (378)..(379)
<223> OTHER INFORMATION: N= A, U, G or C
<221> NAME/KEY: misc_feature
<222> LOCATION: (381)..(381)
<223> OTHER INFORMATION: N= A, U, G or C
<221> NAME/KEY: misc_feature
<222> LOCATION: (384)..(385)
<223> OTHER INFORMATION: N= A, U, G or C
<221> NAME/KEY: misc_feature
<222> LOCATION: (390)..(392)
<223> OTHER INFORMATION: N= A, U, G or C
<221> NAME/KEY: misc_feature
<222> LOCATION: (396)..(396)
<223> OTHER INFORMATION: N= A, U, G or C
<221> NAME/KEY: misc_feature
<222> LOCATION: (398)..(399)
<223> OTHER INFORMATION: N= A, U, G or C
<221> NAME/KEY: misc_feature
<222> LOCATION: (407)..(409)
<223> OTHER INFORMATION: N= A, U, G or C
<221> NAME/KEY: misc_feature
<222> LOCATION: (412)..(412)
<223> OTHER INFORMATION: N= A, U, G or C
<221> NAME/KEY: misc_feature
<222> LOCATION: (415)..(415)
<223> OTHER INFORMATION: N= A, U, G or C
<221> NAME/KEY: misc_feature
<222> LOCATION: (418)..(419)
<223> OTHER INFORMATION: N= A, U, G or C
<221> NAME/KEY: misc_feature
<222> LOCATION: (421)..(423)
<223> OTHER INFORMATION: N= A, U, G or C
<221> NAME/KEY: misc_feature
<222> LOCATION: (425)..(425)
<223> OTHER INFORMATION: N= A, U, G or C
<221> NAME/KEY: misc_feature
<222> LOCATION: (427)..(427)
<223> OTHER INFORMATION: N= A, U, G or C
<221> NAME/KEY: misc_feature
<222> LOCATION: (433)..(435)
<223> OTHER INFORMATION: N= A, U, G or C
<221> NAME/KEY: misc_feature
<222> LOCATION: (438)..(438)
<223> OTHER INFORMATION: N= A, U, G or C
<221> NAME/KEY: misc_feature
<222> LOCATION: (440)..(446)
<223> OTHER INFORMATION: N= A, U, G or C
<221> NAME/KEY: misc_feature
<222> LOCATION: (449)..(449)

-continued

<223> OTHER INFORMATION: N= A, U, G or C
<221> NAME/KEY: misc_feature
<222> LOCATION: (452)..(479)
<223> OTHER INFORMATION: N= A, U, G or C
<221> NAME/KEY: misc_feature
<222> LOCATION: (484)..(485)
<223> OTHER INFORMATION: N= A, U, G or C
<221> NAME/KEY: misc_feature
<222> LOCATION: (488)..(494)
<223> OTHER INFORMATION: N= A, U, G or C
<221> NAME/KEY: misc_feature
<222> LOCATION: (496)..(497)
<223> OTHER INFORMATION: N= A, U, G or C
<221> NAME/KEY: misc_feature
<222> LOCATION: (501)..(503)
<223> OTHER INFORMATION: N= A, U, G or C
<221> NAME/KEY: misc_feature
<222> LOCATION: (508)..(508)
<223> OTHER INFORMATION: N= A, U, G or C
<221> NAME/KEY: misc_feature
<222> LOCATION: (513)..(513)
<223> OTHER INFORMATION: N= A, U, G or C
<221> NAME/KEY: misc_feature
<222> LOCATION: (537)..(537)
<223> OTHER INFORMATION: N= A, U, G or C
<221> NAME/KEY: misc_feature
<222> LOCATION: (542)..(543)
<223> OTHER INFORMATION: N= A, U, G or C
<221> NAME/KEY: misc_feature
<222> LOCATION: (546)..(546)
<223> OTHER INFORMATION: N= A, U, G or C
<221> NAME/KEY: misc_feature
<222> LOCATION: (553)..(555)
<223> OTHER INFORMATION: N= A, U, G or C
<221> NAME/KEY: misc_feature
<222> LOCATION: (560)..(560)
<223> OTHER INFORMATION: N= A, U, G or C
<221> NAME/KEY: misc_feature
<222> LOCATION: (562)..(562)
<223> OTHER INFORMATION: N= A, U, G or C
<221> NAME/KEY: misc_feature
<222> LOCATION: (564)..(564)
<223> OTHER INFORMATION: N= A, U, G or C
<221> NAME/KEY: misc_feature
<222> LOCATION: (576)..(576)
<223> OTHER INFORMATION: N= A, U, G or C
<221> NAME/KEY: misc_feature
<222> LOCATION: (578)..(580)
<223> OTHER INFORMATION: N= A, U, G or C
<221> NAME/KEY: misc_feature
<222> LOCATION: (582)..(582)
<223> OTHER INFORMATION: N= A, U, G or C
<221> NAME/KEY: misc_feature
<222> LOCATION: (586)..(586)
<223> OTHER INFORMATION: N= A, U, G or C
<221> NAME/KEY: misc_feature
<222> LOCATION: (589)..(596)
<223> OTHER INFORMATION: N= A, U, G or C
<221> NAME/KEY: misc_feature
<222> LOCATION: (599)..(603)
<223> OTHER INFORMATION: N= A, U, G or C
<221> NAME/KEY: misc_feature
<222> LOCATION: (606)..(606)
<223> OTHER INFORMATION: N= A, U, G or C
<221> NAME/KEY: misc_feature
<222> LOCATION: (610)..(616)
<223> OTHER INFORMATION: N= A, U, G or C
<221> NAME/KEY: misc_feature
<222> LOCATION: (620)..(620)
<223> OTHER INFORMATION: N= A, U, G or C
<221> NAME/KEY: misc_feature
<222> LOCATION: (624)..(633)
<223> OTHER INFORMATION: N= A, U, G or C
<221> NAME/KEY: misc_feature
<222> LOCATION: (635)..(641)
<223> OTHER INFORMATION: N= A, U, G or C
<221> NAME/KEY: misc_feature
<222> LOCATION: (644)..(650)
<223> OTHER INFORMATION: N= A, U, G or C -continued
<221> NAME/KEY: misc_feature
<222> LOCATION: (653)..(653)
<223> OTHER INFORMATION: N= A, U, G or C
<221> NAME/KEY: misc_feature
<222> LOCATION: (657)..(662)
<223> OTHER INFORMATION: N= A, U, G or C
<221> NAME/KEY: misc_feature
<222> LOCATION: (665)..(665)
<223> OTHER INFORMATION: N= A, U, G or C
<221> NAME/KEY: misc_feature
<222> LOCATION: (668)..(673)
<223> OTHER INFORMATION: N= A, U, G or C
<221> NAME/KEY: misc_feature
<222> LOCATION: (679)..(682)
<223> OTHER INFORMATION: N= A, U, G or C
<221> NAME/KEY: misc_feature
<222> LOCATION: (689)..(689)
<223> OTHER INFORMATION: N= A, U, G or C
<221> NAME/KEY: misc_feature
<222> LOCATION: (694)..(694)
<223> OTHER INFORMATION: N= A, U, G or C
<221> NAME/KEY: misc_feature
<222> LOCATION: (697)..(697)
<223> OTHER INFORMATION: N= A, U, G or C
<221> NAME/KEY: misc_feature
<222> LOCATION: (701)..(701)
<223> OTHER INFORMATION: N= A, U, G or C
<221> NAME/KEY: misc_feature
<222> LOCATION: (705)..(705)
<223> OTHER INFORMATION: N= A, U, G or C
<221> NAME/KEY: misc_feature
<222> LOCATION: (708)..(709)
<223> OTHER INFORMATION: N= A, U, G or C
<221> NAME/KEY: misc_feature
<222> LOCATION: (711)..(711)
<223> OTHER INFORMATION: N= A, U, G or C
<221> NAME/KEY: misc_feature
<222> LOCATION: (713)..(713)
<223> OTHER INFORMATION: N= A, U, G or C
<221> NAME/KEY: misc_feature
<222> LOCATION: (717)..(717)
<223> OTHER INFORMATION: N= A, U, G or C
<221> NAME/KEY: misc_feature
<222> LOCATION: (721)..(722)
<223> OTHER INFORMATION: N= A, U, G or C
<221> NAME/KEY: misc_feature
<222> LOCATION: (724)..(724)
<223> OTHER INFORMATION: N= A, U, G or C
<221> NAME/KEY: misc_feature
<222> LOCATION: (733)..(738)
<223> OTHER INFORMATION: N= A, U, G or C
<221> NAME/KEY: misc_feature
<222> LOCATION: (743)..(748)
<223> OTHER INFORMATION: N= A, U, G or C
<221> NAME/KEY: misc_feature
<222> LOCATION: (755)..(755)
<223> OTHER INFORMATION: N= A, U, G or C
<221> NAME/KEY: misc_feature
<222> LOCATION: (758)..(758)
<223> OTHER INFORMATION: N= A, U, G or C
<221> NAME/KEY: misc_feature
<222> LOCATION: (760)..(763)
<223> OTHER INFORMATION: N= A, U, G or C
<221> NAME/KEY: misc_feature
<222> LOCATION: (770)..(770)
<223> OTHER INFORMATION: N= A, U, G or C
<221> NAME/KEY: misc_feature
<222> LOCATION: (775)..(775)
<223> OTHER INFORMATION: N= A, U, G or C
<221> NAME/KEY: misc_feature
<222> LOCATION: (780)..(780)
<223> OTHER INFORMATION: N= A, U, G or C
<221> NAME/KEY: misc_feature
<222> LOCATION: (808)..(808)
<223> OTHER INFORMATION: N= A, U, G or C
<221> NAME/KEY: misc_feature
<222> LOCATION: (811)..(812)
<223> OTHER INFORMATION: N= A, U, G or C
<221> NAME/KEY: misc_feature -continued
<222> LOCATION: (819)..(819)
<223> OTHER INFORMATION: N= A, U, G or C
<221> NAME/KEY: misc_feature
<222> LOCATION: (822)..(826)
<223> OTHER INFORMATION: N= A, U, G or C
<221> NAME/KEY: misc_feature
<222> LOCATION: (828)..(831)
<223> OTHER INFORMATION: N= A, U, G or C
<221> NAME/KEY: misc_feature
<222> LOCATION: (833)..(835)
<223> OTHER INFORMATION: N= A, U, G or C
<221> NAME/KEY: misc_feature
<222> LOCATION: (837)..(859)
<223> OTHER INFORMATION: N= A, U, G or C
<221> NAME/KEY: misc_feature
<222> LOCATION: (861)..(863)
<223> OTHER INFORMATION: N= A, U, G or C
<221> NAME/KEY: misc_feature
<222> LOCATION: (868)..(870)
<223> OTHER INFORMATION: N= A, U, G or C
<221> NAME/KEY: misc_feature
<222> LOCATION: (874)..(878)
<223> OTHER INFORMATION: N= A, U, G or C
<221> NAME/KEY: misc_feature
<222> LOCATION: (895)..(896)
<223> OTHER INFORMATION: N= A, U, G or C
<221> NAME/KEY: misc_feature
<222> LOCATION: (903)..(904)
<223> OTHER INFORMATION: N= A, U, G or C
<221> NAME/KEY: misc_feature
<222> LOCATION: (906)..(906)
<223> OTHER INFORMATION: N= A, U, G or C
<221> NAME/KEY: misc_feature
<222> LOCATION: (916)..(916)
<223> OTHER INFORMATION: N= A, U, G or C
<221> NAME/KEY: misc_feature
<222> LOCATION: (929)..(929)
<223> OTHER INFORMATION: N= A, U, G or C
<221> NAME/KEY: misc_feature
<222> LOCATION: (932)..(932)
<223> OTHER INFORMATION: N= A, U, G or C
<221> NAME/KEY: misc_feature
<222> LOCATION: (941)..(941)
<223> OTHER INFORMATION: N= A, U, G or C
<221> NAME/KEY: misc_feature
<222> LOCATION: (943)..(943)
<223> OTHER INFORMATION: N= A, U, G or C
<221> NAME/KEY: misc_feature
<222> LOCATION: (948)..(948)
<223> OTHER INFORMATION: N= A, U, G or C
<221> NAME/KEY: misc_feature
<222> LOCATION: (955)..(955)
<223> OTHER INFORMATION: N= A, U, G or C
<221> NAME/KEY: misc_feature
<222> LOCATION: (965)..(965)
<223> OTHER INFORMATION: N= A, U, G or C
<221> NAME/KEY: misc_feature
<222> LOCATION: (967)..(968)
<223> OTHER INFORMATION: N= A, U, G or C
<221> NAME/KEY: misc_feature
<222> LOCATION: (974)..(974)
<223> OTHER INFORMATION: N= A, U, G or C
<221> NAME/KEY: misc_feature
<222> LOCATION: (976)..(976)
<223> OTHER INFORMATION: N= A, U, G or C
<221> NAME/KEY: misc_feature
<222> LOCATION: (986)..(990)
<223> OTHER INFORMATION: N= A, U, G or C
<221> NAME/KEY: misc_feature
<222> LOCATION: (998)..(1012)
<223> OTHER INFORMATION: N= A, U, G or C
<221> NAME/KEY: misc_feature
<222> LOCATION: (1015)..(1015)
<223> OTHER INFORMATION: N= A, U, G or C
<221> NAME/KEY: misc_feature
<222> LOCATION: (1017)..(1043)
<223> OTHER INFORMATION: N= A, U, G or C
<221> NAME/KEY: misc_feature
<222> LOCATION: (1051)..(1051)

-continued

<223> OTHER INFORMATION: N= A, U, G or C
<221> NAME/KEY: misc_feature
<222> LOCATION: (1059)..(1059)
<223> OTHER INFORMATION: N= A, U, G or C
<221> NAME/KEY: misc_feature
<222> LOCATION: (1075)..(1076)
<223> OTHER INFORMATION: N= A, U, G or C
<221> NAME/KEY: misc_feature
<222> LOCATION: (1082)..(1082)
<223> OTHER INFORMATION: N= A, U, G or C
<221> NAME/KEY: misc_feature
<222> LOCATION: (1100)..(1100)
<223> OTHER INFORMATION: N= A, U, G or C
<221> NAME/KEY: misc_feature
<222> LOCATION: (1115)..(1123)
<223> OTHER INFORMATION: N= A, U, G or C
<221> NAME/KEY: misc_feature
<222> LOCATION: (1127)..(1127)
<223> OTHER INFORMATION: N= A, U, G or C
<221> NAME/KEY: misc_feature
<222> LOCATION: (1129)..(1130)
<223> OTHER INFORMATION: N= A, U, G or C
<221> NAME/KEY: misc_feature
<222> LOCATION: (1132)..(1141)
<223> OTHER INFORMATION: N= A, U, G or C
<221> NAME/KEY: misc_feature
<222> LOCATION: (1143)..(1143)
<223> OTHER INFORMATION: N= A, U, G or C
<221> NAME/KEY: misc_feature
<222> LOCATION: (1145)..(1145)
<223> OTHER INFORMATION: N= A, U, G or C
<221> NAME/KEY: misc_feature
<222> LOCATION: (1150)..(1156)
<223> OTHER INFORMATION: N= A, U, G or C
<221> NAME/KEY: misc_feature
<222> LOCATION: (1163)..(1165)
<223> OTHER INFORMATION: N= A, U, G or C
<221> NAME/KEY: misc_feature
<222> LOCATION: (1167)..(1168)
<223> OTHER INFORMATION: N= A, U, G or C
<221> NAME/KEY: misc_feature
<222> LOCATION: (1171)..(1173)
<223> OTHER INFORMATION: N= A, U, G or C
<221> NAME/KEY: misc_feature
<222> LOCATION: (1183)..(1183)
<223> OTHER INFORMATION: N= A, U, G or C
<221> NAME/KEY: misc_feature
<222> LOCATION: (1189)..(1189)
<223> OTHER INFORMATION: N= A, U, G or C
<221> NAME/KEY: misc_feature
<222> LOCATION: (1198)..(1198)
<223> OTHER INFORMATION: N= A, U, G or C
<221> NAME/KEY: misc_feature
<222> LOCATION: (1201)..(1201)
<223> OTHER INFORMATION: N= A, U, G or C
<221> NAME/KEY: misc_feature
<222> LOCATION: (1207)..(1207)
<223> OTHER INFORMATION: N= A, U, G or C
<221> NAME/KEY: misc_feature
<222> LOCATION: (1214)..(1214)
<223> OTHER INFORMATION: N= A, U, G or C
<221> NAME/KEY: misc_feature
<222> LOCATION: (1216)..(1219)
<223> OTHER INFORMATION: N= A, U, G or C
<221> NAME/KEY: misc_feature
<222> LOCATION: (1225)..(1225)
<223> OTHER INFORMATION: N= A, U, G or C
<221> NAME/KEY: misc_feature
<222> LOCATION: (1231)..(1231)
<223> OTHER INFORMATION: N= A, U, G or C
<221> NAME/KEY: misc_feature
<222> LOCATION: (1233)..(1233)
<223> OTHER INFORMATION: N= A, U, G or C
<221> NAME/KEY: misc_feature
<222> LOCATION: (1243)..(1247)
<223> OTHER INFORMATION: N= A, U, G or C
<221> NAME/KEY: misc_feature
<222> LOCATION: (1251)..(1252)
<223> OTHER INFORMATION: N= A, U, G or C -continued
<221> NAME/KEY: misc_feature
<222> LOCATION: (1254)..(1254)
<223> OTHER INFORMATION: N= A, U, G or C
<221> NAME/KEY: misc_feature
<222> LOCATION: (1256)..(1257)
<223> OTHER INFORMATION: N= A, U, G or C
<221> NAME/KEY: misc_feature
<222> LOCATION: (1260)..(1260)
<223> OTHER INFORMATION: N= A, U, G or C
<221> NAME/KEY: misc_feature
<222> LOCATION: (1262)..(1265)
<223> OTHER INFORMATION: N= A, U, G or C
<221> NAME/KEY: misc_feature
<222> LOCATION: (1267)..(1268)
<223> OTHER INFORMATION: N= A, U, G or C
<221> NAME/KEY: misc_feature
<222> LOCATION: (1270)..(1274)
<223> OTHER INFORMATION: N= A, U, G or C
<221> NAME/KEY: misc_feature
<222> LOCATION: (1278)..(1278)
<223> OTHER INFORMATION: N= A, U, G or C
<221> NAME/KEY: misc_feature
<222> LOCATION: (1281)..(1281)
<223> OTHER INFORMATION: N= A, U, G or C
<221> NAME/KEY: misc_feature
<222> LOCATION: (1283)..(1286)
<223> OTHER INFORMATION: N= A, U, G or C
<221> NAME/KEY: misc_feature
<222> LOCATION: (1290)..(1294)
<223> OTHER INFORMATION: N= A, U, G or C
<221> NAME/KEY: misc_feature
<222> LOCATION: (1297)..(1298)
<223> OTHER INFORMATION: N= A, U, G or C
<221> NAME/KEY: misc_feature
<222> LOCATION: (1302)..(1302)
<223> OTHER INFORMATION: N= A, U, G or C
<221> NAME/KEY: misc_feature
<222> LOCATION: (1308)..(1308)
<223> OTHER INFORMATION: N= A, U, G or C
<221> NAME/KEY: misc_feature
<222> LOCATION: (1310)..(1313)
<223> OTHER INFORMATION: N= A, U, G or C
<221> NAME/KEY: misc_feature
<222> LOCATION: (1324)..(1327)
<223> OTHER INFORMATION: N= A, U, G or C
<221> NAME/KEY: misc_feature
<222> LOCATION: (1329)..(1329)
<223> OTHER INFORMATION: N= A, U, G or C
<221> NAME/KEY: misc_feature
<222> LOCATION: (1335)..(1336)
<223> OTHER INFORMATION: N= A, U, G or C
<221> NAME/KEY: misc_feature
<222> LOCATION: (1340)..(1340)
<223> OTHER INFORMATION: N= A, U, G or C
<221> NAME/KEY: misc_feature
<222> LOCATION: (1354)..(1356)
<223> OTHER INFORMATION: N= A, U, G or C
<221> NAME/KEY: misc_feature
<222> LOCATION: (1362)..(1362)
<223> OTHER INFORMATION: N= A, U, G or C
<221> NAME/KEY: misc_feature
<222> LOCATION: (1364)..(1364)
<223> OTHER INFORMATION: N= A, U, G or C
<221> NAME/KEY: misc_feature
<222> LOCATION: (1366)..(1368)
<223> OTHER INFORMATION: N= A, U, G or C
<221> NAME/KEY: misc_feature
<222> LOCATION: (1383)..(1383)
<223> OTHER INFORMATION: N= A, U, G or C
<221> NAME/KEY: misc_feature
<222> LOCATION: (1388)..(1388)
<223> OTHER INFORMATION: N= A, U, G or C
<221> NAME/KEY: misc_feature
<222> LOCATION: (1409)..(1411)
<223> OTHER INFORMATION: N= A, U, G or C
<221> NAME/KEY: misc_feature
<222> LOCATION: (1414)..(1414)
<223> OTHER INFORMATION: N= A, U, G or C
<221> NAME/KEY: misc_feature -continued
<222> LOCATION: (1416)..(1417)
<223> OTHER INFORMATION: N= A, U, G or C
<221> NAME/KEY: misc_feature
<222> LOCATION: (1420)..(1428)
<223> OTHER INFORMATION: N= A, U, G or C
<221> NAME/KEY: misc_feature
<222> LOCATION: (1431)..(1432)
<223> OTHER INFORMATION: N= A, U, G or C
<221> NAME/KEY: misc_feature
<222> LOCATION: (1436)..(1447)
<223> OTHER INFORMATION: N= A, U, G or C
<221> NAME/KEY: misc_feature
<222> LOCATION: (1449)..(1454)
<223> OTHER INFORMATION: N= A, U, G or C
<221> NAME/KEY: misc_feature
<222> LOCATION: (1456)..(1465)
<223> OTHER INFORMATION: N= A, U, G or C
<221> NAME/KEY: misc_feature
<222> LOCATION: (1467)..(1467)
<223> OTHER INFORMATION: N= A, U, G or C
<221> NAME/KEY: misc_feature
<222> LOCATION: (1469)..(1469)
<223> OTHER INFORMATION: N= A, U, G or C
<221> NAME/KEY: misc_feature
<222> LOCATION: (1472)..(1481)
<223> OTHER INFORMATION: N= A, U, G or C
<221> NAME/KEY: misc_feature
<222> LOCATION: (1484)..(1484)
<223> OTHER INFORMATION: N= A, U, G or C
<221> NAME/KEY: misc_feature
<222> LOCATION: (1489)..(1491)
<223> OTHER INFORMATION: N= A, U, G or C
<221> NAME/KEY: misc_feature
<222> LOCATION: (1508)..(1508)
<223> OTHER INFORMATION: N= A, U, G or C
<221> NAME/KEY: misc_feature
<222> LOCATION: (1511)..(1511)
<223> OTHER INFORMATION: N= A, U, G or C
<221> NAME/KEY: misc_feature
<222> LOCATION: (1514)..(1516)
<223> OTHER INFORMATION: N= A, U, G or C
<221> NAME/KEY: misc_feature
<222> LOCATION: (1520)..(1521)
<223> OTHER INFORMATION: N= A, U, G or C
<221> NAME/KEY: misc_feature
<222> LOCATION: (1524)..(1524)
<223> OTHER INFORMATION: N= A, U, G or C
<221> NAME/KEY: misc_feature
<222> LOCATION: (1527)..(1527)
<223> OTHER INFORMATION: N= A, U, G or C
<221> NAME/KEY: misc_feature
<222> LOCATION: (1542)..(1542)
<223> OTHER INFORMATION: N= A, U, G or C

<400> SEQUENCE: 3
nnnnnnnaga guuugaucnu ggcucagnnn gaacgcuggc ggnnngcnun anacaugcaa 60 gucganc gnn nnnnnnnnnn nnnnnnnnnn nnnnnnnnnn agnggcnnac gggugaguaa 120
nncnunnnna nnunccnnnn nnnnnggnan annnnnnnga aannnnnnnu aauaccnnau 180
nnnnnnnnnn nnnnaaagnn nnnnnnnnnn nnnnnnnnnn nnnnnngann nnnnnnngnn 240
nnaunagnun guuggunngg uaanggcnna ccaagncnnn gannnnuagc ngnncugaga 300
ggnngnncng ccacanuggn acugaganac ggnccanacu ccuacgggag gcagcagunn 360
ggaaunuunn ncaauggnng naanncugan nnagcnannc cgcgugnnng anganggnnu 420
nnngnungua aannncunun nnnnnngang annnnnnnnn nnnnnnnnnn nnnnnnnnnu 480
gacnnuannn nnnnannaag nnncggcnaa cuncgugcca gcagccgcgg uaauacgnag 540
gnngcnagcg uunnncggan unanugggcg uaaagngnnn gnaggnggnn nnnnnngunn 600
nnngunaaan nnnnnngcun aacnnnnnnn nnncnnnnnn nacnnnnnnn cungagnnnn 660
nnagnggnnn nnngaauunn nnguguagng gugnaauncg naganaunng nangaanacc 720

-continued

```
nnungcgaag gcnnnnnncu ggnnnnnnac ugacncunan nnncgaaagc nugggnagcn    780

aacaggauua gauacccugg uaguccangc nnuaaacgnu gnnnnnunnn ngnnngnnnn    840

nnnnnnnnnn nnnnnnnnna nnnaacgnnn uaannnnncc gccuggggag uacgnncgca    900

agnnunaaac ucaaangaau ugacggggnc cngcacaagc ngnggagnau guggnuuaau    960

ucgangnnac gcgnanaacc uuaccnnnnn uugacaunnn nnnnnnnnnn nnganannnn   1020

nnnnnnnnnn nnnnnnnnnn nnnacaggug nugcauggnu gucgucagcu cgugnnguga   1080

gnuguugggu uaagucccgn aacgagcgca acccnnnnnn nnnguuncna ncnnnnnnnn   1140

ngngnacucn nnnnnnacug ccnnngnnaa nnnggaggaa ggnggggang acgucaanuc   1200

nucaugnccc uuangnnnng ggcuncacac nuncuacaau ggnnnnnaca nngngnngcn   1260

annnngnnan nnnnagcnaa ncnnnnaaan nnnnucnnag uncggaungn nnncugcaac   1320

ucgnnnncnu gaagnnggan ucgcuaguaa ucgnnnauca gnangnnncg gugaauacgu   1380

ucncgggncu uguacacacc gcccgucann ncangnnagn nnnnnnnncc nnaagnnnnn   1440

nnnnnnncnn nnnngnnnnn nnnnncnang gnnnnnnnnn nganugggnn naagucguaa   1500

caagguancc nuannngaan nugnggnugg aucaccuccu un                      1542
```

```
<210> SEQ ID NO 4
<211> LENGTH: 2904
<212> TYPE: RNA
<213> ORGANISM: Artificial Sequence
<220> FEATURE:
<221> NAME/KEY: misc_feature
<223> OTHER INFORMATION: 23S rRNA consensus sequence
<221> NAME/KEY: misc_feature
<222> LOCATION: (1)..(4)
<223> OTHER INFORMATION: N= A, U, G or C
<221> NAME/KEY: misc_feature
<222> LOCATION: (8)..(12)
<223> OTHER INFORMATION: N= A, U, G or C
<221> NAME/KEY: misc_feature
<222> LOCATION: (16)..(16)
<223> OTHER INFORMATION: N= A,U, G or C
<221> NAME/KEY: misc_feature
<222> LOCATION: (18)..(22)
<223> OTHER INFORMATION: N= A,U, G or C
<221> NAME/KEY: misc_feature
<222> LOCATION: (34)..(34)
<223> OTHER INFORMATION: N= A,U, G or C
<221> NAME/KEY: misc_feature
<222> LOCATION: (38)..(43)
<223> OTHER INFORMATION: N= A,U, G or C
<221> NAME/KEY: misc_feature
<222> LOCATION: (46)..(46)
<223> OTHER INFORMATION: N= A,U, G or C
<221> NAME/KEY: misc_feature
<222> LOCATION: (50)..(50)
<223> OTHER INFORMATION: N= A,U, G or C
<221> NAME/KEY: misc_feature
<222> LOCATION: (57)..(57)
<223> OTHER INFORMATION: N= A, U, G or C
<221> NAME/KEY: misc_feature
<222> LOCATION: (59)..(65)
<223> OTHER INFORMATION: N= A, U, G or C
<221> NAME/KEY: misc_feature
<222> LOCATION: (67)..(68)
<223> OTHER INFORMATION: N= A, U, G or C
<221> NAME/KEY: misc_feature
<222> LOCATION: (70)..(72)
<223> OTHER INFORMATION: N= A, U, G or C
<221> NAME/KEY: misc_feature
<222> LOCATION: (74)..(75)
<223> OTHER INFORMATION: N= A, U, G or C
<221> NAME/KEY: misc_feature
<222> LOCATION: (77)..(79)
<223> OTHER INFORMATION: N= A, U, G or C
```

-continued

<221> NAME/KEY: misc_feature
<222> LOCATION: (82)..(83)
<223> OTHER INFORMATION: N= A, U, G or C
<221> NAME/KEY: misc_feature
<222> LOCATION: (86)..(87)
<223> OTHER INFORMATION: N= A, U, G or C
<221> NAME/KEY: misc_feature
<222> LOCATION: (89)..(96)
<223> OTHER INFORMATION: N= A, U, G or C
<221> NAME/KEY: misc_feature
<222> LOCATION: (98)..(102)
<223> OTHER INFORMATION: N= A, U, G or C
<221> NAME/KEY: misc_feature
<222> LOCATION: (104)..(104)
<223> OTHER INFORMATION: N= A, U, G or C
<221> NAME/KEY: misc_feature
<222> LOCATION: (107)..(109)
<223> OTHER INFORMATION: N= A, U, G or C
<221> NAME/KEY: misc_feature
<222> LOCATION: (111)..(113)
<223> OTHER INFORMATION: N= A, U, G or C
<221> NAME/KEY: misc_feature
<222> LOCATION: (113)..(113)
<223> OTHER INFORMATION: N= A, U, G or C
<221> NAME/KEY: misc_feature
<222> LOCATION: (125)..(125)
<223> OTHER INFORMATION: N= A, U, G or C
<221> NAME/KEY: misc_feature
<222> LOCATION: (131)..(148)
<223> OTHER INFORMATION: N= A, U, G or C
<221> NAME/KEY: misc_feature
<222> LOCATION: (150)..(177)
<223> OTHER INFORMATION: N= A, U, G or C
<221> NAME/KEY: misc_feature
<222> LOCATION: (179)..(181)
<223> OTHER INFORMATION: N= A, U, G or C
<221> NAME/KEY: misc_feature
<222> LOCATION: (184)..(188)
<223> OTHER INFORMATION: N= A, U, G or C
<221> NAME/KEY: misc_feature
<222> LOCATION: (192)..(192)
<223> OTHER INFORMATION: N= A, U, G or C
<221> NAME/KEY: misc_feature
<222> LOCATION: (203)..(203)
<223> OTHER INFORMATION: N= A, U, G or C
<221> NAME/KEY: misc_feature
<222> LOCATION: (208)..(212)
<223> OTHER INFORMATION: N= A, U, G or C
<221> NAME/KEY: misc_feature
<222> LOCATION: (218)..(218)
<223> OTHER INFORMATION: N= A, U, G or C
<221> NAME/KEY: misc_feature
<222> LOCATION: (224)..(225)
<223> OTHER INFORMATION: N= A, U, G or C
<221> NAME/KEY: misc_feature
<222> LOCATION: (228)..(231)
<223> OTHER INFORMATION: N= A, U, G or C
<221> NAME/KEY: misc_feature
<222> LOCATION: (236)..(236)
<223> OTHER INFORMATION: N= A, U, G or C
<221> NAME/KEY: misc_feature
<222> LOCATION: (238)..(241)
<223> OTHER INFORMATION: N= A, U, G or C
<221> NAME/KEY: misc_feature
<222> LOCATION: (246)..(246)
<223> OTHER INFORMATION: N= A, U, G or C
<221> NAME/KEY: misc_feature
<222> LOCATION: (257)..(259)
<223> OTHER INFORMATION: N= A, U, G or C
<221> NAME/KEY: misc_feature
<222> LOCATION: (261)..(261)
<223> OTHER INFORMATION: N= A, U, G or C
<221> NAME/KEY: misc_feature
<222> LOCATION: (263)..(264)
<223> OTHER INFORMATION: N= A, U, G or C
<221> NAME/KEY: misc_feature
<222> LOCATION: (267)..(267)
<223> OTHER INFORMATION: N= A, U, G or C
<221> NAME/KEY: misc_feature -continued
<222> LOCATION: (269)..(293)
<223> OTHER INFORMATION: N= A, U, G or C
<221> NAME/KEY: misc_feature
<222> LOCATION: (295)..(297)
<223> OTHER INFORMATION: N= A, U, G or C
<221> NAME/KEY: misc_feature
<222> LOCATION: (301)..(305)
<223> OTHER INFORMATION: N= A, U, G or C
<221> NAME/KEY: misc_feature
<222> LOCATION: (309)..(309)
<223> OTHER INFORMATION: N= A, U, G or C
<221> NAME/KEY: misc_feature
<222> LOCATION: (313)..(321)
<223> OTHER INFORMATION: N= A, U, G or C
<221> NAME/KEY: misc_feature
<222> LOCATION: (323)..(325)
<223> OTHER INFORMATION: N= A, U, G or C
<221> NAME/KEY: misc_feature
<222> LOCATION: (329)..(329)
<223> OTHER INFORMATION: N= A, U, G or C
<221> NAME/KEY: misc_feature
<222> LOCATION: (331)..(331)
<223> OTHER INFORMATION: N= A, U, G or C
<221> NAME/KEY: misc_feature
<222> LOCATION: (333)..(334)
<223> OTHER INFORMATION: N= A, U, G or C
<221> NAME/KEY: misc_feature
<222> LOCATION: (337)..(337)
<223> OTHER INFORMATION: N= A, U, G or C
<221> NAME/KEY: misc_feature
<222> LOCATION: (341)..(344)
<223> OTHER INFORMATION: N= A, U, G or C
<221> NAME/KEY: misc_feature
<222> LOCATION: (348)..(370)
<223> OTHER INFORMATION: N= A, U, G or C
<221> NAME/KEY: misc_feature
<222> LOCATION: (375)..(377)
<223> OTHER INFORMATION: N= A, U, G or C
<221> NAME/KEY: misc_feature
<222> LOCATION: (379)..(382)
<223> OTHER INFORMATION: N= A, U, G or C
<221> NAME/KEY: misc_feature
<222> LOCATION: (384)..(384)
<223> OTHER INFORMATION: N= A, U, G or C
<221> NAME/KEY: misc_feature
<222> LOCATION: (387)..(387)
<223> OTHER INFORMATION: N= A, U, G or C
<221> NAME/KEY: misc_feature
<222> LOCATION: (389)..(390)
<223> OTHER INFORMATION: N= A, U, G or C
<221> NAME/KEY: misc_feature
<222> LOCATION: (392)..(395)
<223> OTHER INFORMATION: N= A, U, G or C
<221> NAME/KEY: misc_feature
<222> LOCATION: (398)..(399)
<223> OTHER INFORMATION: N= A, U, G or C
<221> NAME/KEY: misc_feature
<222> LOCATION: (403)..(405)
<223> OTHER INFORMATION: N= A, U, G or C
<221> NAME/KEY: misc_feature
<222> LOCATION: (407)..(410)
<223> OTHER INFORMATION: N= A, U, G or C
<221> NAME/KEY: misc_feature
<222> LOCATION: (416)..(421)
<223> OTHER INFORMATION: N= A, U, G or C
<221> NAME/KEY: misc_feature
<222> LOCATION: (425)..(425)
<223> OTHER INFORMATION: N= A, U, G or C
<221> NAME/KEY: misc_feature
<222> LOCATION: (435)..(441)
<223> OTHER INFORMATION: N= A, U, G or C
<221> NAME/KEY: misc_feature
<222> LOCATION: (446)..(446)
<223> OTHER INFORMATION: N= A, U, G or C
<221> NAME/KEY: misc_feature
<222> LOCATION: (451)..(451)
<223> OTHER INFORMATION: N= A, U, G or C
<221> NAME/KEY: misc_feature
<222> LOCATION: (453)..(453)

-continued

<223> OTHER INFORMATION: N= A, U, G or C
<221> NAME/KEY: misc_feature
<222> LOCATION: (455)..(456)
<223> OTHER INFORMATION: N= A, U, G or C
<221> NAME/KEY: misc_feature
<222> LOCATION: (462)..(462)
<223> OTHER INFORMATION: N= A, U, G or C
<221> NAME/KEY: misc_feature
<222> LOCATION: (467)..(467)
<223> OTHER INFORMATION: N= A, U, G or C
<221> NAME/KEY: misc_feature
<222> LOCATION: (475)..(475)
<223> OTHER INFORMATION: N= A, U, G or C
<221> NAME/KEY: misc_feature
<222> LOCATION: (482)..(482)
<223> OTHER INFORMATION: N= A, U, G or C
<221> NAME/KEY: misc_feature
<222> LOCATION: (487)..(491)
<223> OTHER INFORMATION: N= A, U, G or C
<221> NAME/KEY: misc_feature
<222> LOCATION: (493)..(493)
<223> OTHER INFORMATION: N= A, U, G or C
<221> NAME/KEY: misc_feature
<222> LOCATION: (504)..(504)
<223> OTHER INFORMATION: N= A, U, G or C
<221> NAME/KEY: misc_feature
<222> LOCATION: (507)..(508)
<223> OTHER INFORMATION: N= A, U, G or C
<221> NAME/KEY: misc_feature
<222> LOCATION: (518)..(522)
<223> OTHER INFORMATION: N= A, U, G or C
<221> NAME/KEY: misc_feature
<222> LOCATION: (524)..(524)
<223> OTHER INFORMATION: N= A, U, G or C
<221> NAME/KEY: misc_feature
<222> LOCATION: (527)..(527)
<223> OTHER INFORMATION: N= A, U, G or C
<221> NAME/KEY: misc_feature
<222> LOCATION: (530)..(532)
<223> OTHER INFORMATION: N= A, U, G or C
<221> NAME/KEY: misc_feature
<222> LOCATION: (535)..(537)
<223> OTHER INFORMATION: N= A, U, G or C
<221> NAME/KEY: misc_feature
<222> LOCATION: (540)..(553)
<223> OTHER INFORMATION: N= A, U, G or C
<221> NAME/KEY: misc_feature
<222> LOCATION: (557)..(558)
<223> OTHER INFORMATION: N= A, U, G or C
<221> NAME/KEY: misc_feature
<222> LOCATION: (563)..(563)
<223> OTHER INFORMATION: N= A, U, G or C
<221> NAME/KEY: misc_feature
<222> LOCATION: (571)..(571)
<223> OTHER INFORMATION: N= A, U, G or C
<221> NAME/KEY: misc_feature
<222> LOCATION: (573)..(574)
<223> OTHER INFORMATION: N= A, U, G or C
<221> NAME/KEY: misc_feature
<222> LOCATION: (578)..(580)
<223> OTHER INFORMATION: N= A, U, G or C
<221> NAME/KEY: misc_feature
<222> LOCATION: (582)..(582)
<223> OTHER INFORMATION: N= A, U, G or C
<221> NAME/KEY: misc_feature
<222> LOCATION: (584)..(584)
<223> OTHER INFORMATION: N= A, U, G or C
<221> NAME/KEY: misc_feature
<222> LOCATION: (587)..(587)
<223> OTHER INFORMATION: N= A, U, G or C
<221> NAME/KEY: misc_feature
<222> LOCATION: (590)..(593)
<223> OTHER INFORMATION: N= A, U, G or C
<221> NAME/KEY: misc_feature
<222> LOCATION: (595)..(599)
<223> OTHER INFORMATION: N= A, U, G or C
<221> NAME/KEY: misc_feature
<222> LOCATION: (602)..(602)
<223> OTHER INFORMATION: N= A, U, G or C -continued
<221> NAME/KEY: misc_feature
<222> LOCATION: (605)..(605)
<223> OTHER INFORMATION: N= A, U, G or C
<221> NAME/KEY: misc_feature
<222> LOCATION: (610)..(618)
<223> OTHER INFORMATION: N= A, U, G or C
<221> NAME/KEY: misc_feature
<222> LOCATION: (620)..(620)
<223> OTHER INFORMATION: N= A, U, G or C
<221> NAME/KEY: misc_feature
<222> LOCATION: (623)..(623)
<223> OTHER INFORMATION: N= A, U, G or C
<221> NAME/KEY: misc_feature
<222> LOCATION: (626)..(626)
<223> OTHER INFORMATION: N= A, U, G or C
<221> NAME/KEY: misc_feature
<222> LOCATION: (629)..(629)
<223> OTHER INFORMATION: N= A, U, G or C
<221> NAME/KEY: misc_feature
<222> LOCATION: (634)..(634)
<223> OTHER INFORMATION: N= A, U, G or C
<221> NAME/KEY: misc_feature
<222> LOCATION: (640)..(642)
<223> OTHER INFORMATION: N= A, U, G or C
<221> NAME/KEY: misc_feature
<222> LOCATION: (645)..(646)
<223> OTHER INFORMATION: N= A, U, G or C
<221> NAME/KEY: misc_feature
<222> LOCATION: (648)..(648)
<223> OTHER INFORMATION: N= A, U, G or C
<221> NAME/KEY: misc_feature
<222> LOCATION: (652)..(654)
<223> OTHER INFORMATION: N= A, U, G or C
<221> NAME/KEY: misc_feature
<222> LOCATION: (658)..(662)
<223> OTHER INFORMATION: N= A, U, G or C
<221> NAME/KEY: misc_feature
<222> LOCATION: (664)..(667)
<223> OTHER INFORMATION: N= A, U, G or C
<221> NAME/KEY: misc_feature
<222> LOCATION: (672)..(672)
<223> OTHER INFORMATION: N= A, U, G or C
<221> NAME/KEY: misc_feature
<222> LOCATION: (677)..(677)
<223> OTHER INFORMATION: N= A, U, G or C
<221> NAME/KEY: misc_feature
<222> LOCATION: (679)..(681)
<223> OTHER INFORMATION: N= A, U, G or C
<221> NAME/KEY: misc_feature
<222> LOCATION: (686)..(686)
<223> OTHER INFORMATION: N= A, U, G or C
<221> NAME/KEY: misc_feature
<222> LOCATION: (690)..(692)
<223> OTHER INFORMATION: N= A, U, G or C
<221> NAME/KEY: misc_feature
<222> LOCATION: (696)..(697)
<223> OTHER INFORMATION: N= A, U, G or C
<221> NAME/KEY: misc_feature
<222> LOCATION: (702)..(702)
<223> OTHER INFORMATION: N= A, U, G or C
<221> NAME/KEY: misc_feature
<222> LOCATION: (708)..(712)
<223> OTHER INFORMATION: N= A, U, G or C
<221> NAME/KEY: misc_feature
<222> LOCATION: (717)..(717)
<223> OTHER INFORMATION: N= A, U, G or C
<221> NAME/KEY: misc_feature
<222> LOCATION: (719)..(723)
<223> OTHER INFORMATION: N= A, U, G or C
<221> NAME/KEY: misc_feature
<222> LOCATION: (730)..(730)
<223> OTHER INFORMATION: N= A, U, G or C
<221> NAME/KEY: misc_feature
<222> LOCATION: (737)..(744)
<223> OTHER INFORMATION: N= A, U, G or C
<221> NAME/KEY: misc_feature
<222> LOCATION: (753)..(758)
<223> OTHER INFORMATION: N= A, U, G or C
<221> NAME/KEY: misc_feature
<222> LOCATION: (765)..(766)
<223> OTHER INFORMATION: N= A, U, G or C
<221> NAME/KEY: misc_feature
<222> LOCATION: (771)..(772)
<223> OTHER INFORMATION: N= A, U, G or C
<221> NAME/KEY: misc_feature
<222> LOCATION: (774)..(774)
<223> OTHER INFORMATION: N= A, U, G or C
<221> NAME/KEY: misc_feature
<222> LOCATION: (776)..(776)
<223> OTHER INFORMATION: N= A, U, G or C
<221> NAME/KEY: misc_feature
<222> LOCATION: (779)..(779)
<223> OTHER INFORMATION: N= A, U, G or C
<221> NAME/KEY: misc_feature
<222> LOCATION: (784)..(785)
<223> OTHER INFORMATION: N= A, U, G or C
<221> NAME/KEY: misc_feature
<222> LOCATION: (787)..(787)
<223> OTHER INFORMATION: N= A, U, G or C
<221> NAME/KEY: misc_feature
<222> LOCATION: (790)..(790)
<223> OTHER INFORMATION: N= A, U, G or C
<221> NAME/KEY: misc_feature
<222> LOCATION: (792)..(792)
<223> OTHER INFORMATION: N= A, U, G or C
<221> NAME/KEY: misc_feature
<222> LOCATION: (796)..(798)
<223> OTHER INFORMATION: N= A, U, G or C
<221> NAME/KEY: misc_feature
<222> LOCATION: (800)..(801)
<223> OTHER INFORMATION: N= A, U, G or C
<221> NAME/KEY: misc_feature
<222> LOCATION: (815)..(816)
<223> OTHER INFORMATION: N= A, U, G or C
<221> NAME/KEY: misc_feature
<222> LOCATION: (822)..(825)
<223> OTHER INFORMATION: N= A, U, G or C
<221> NAME/KEY: misc_feature
<222> LOCATION: (832)..(835)
<223> OTHER INFORMATION: N= A, U, G or C
<221> NAME/KEY: misc_feature
<222> LOCATION: (838)..(838)
<223> OTHER INFORMATION: N= A, U, G or C
<221> NAME/KEY: misc_feature
<222> LOCATION: (840)..(854)
<223> OTHER INFORMATION: N= A, U, G or C
<221> NAME/KEY: misc_feature
<222> LOCATION: (857)..(857)
<223> OTHER INFORMATION: N= A, U, G or C
<221> NAME/KEY: misc_feature
<222> LOCATION: (870)..(879)
<223> OTHER INFORMATION: N= A, U, G or C
<221> NAME/KEY: misc_feature
<222> LOCATION: (882)..(894)
<223> OTHER INFORMATION: N= A, U, G or C
<221> NAME/KEY: misc_feature
<222> LOCATION: (898)..(899)
<223> OTHER INFORMATION: N= A, U, G or C
<221> NAME/KEY: misc_feature
<222> LOCATION: (901)..(907)
<223> OTHER INFORMATION: N= A, U, G or C
<221> NAME/KEY: misc_feature
<222> LOCATION: (914)..(914)
<223> OTHER INFORMATION: N= A, U, G or C
<221> NAME/KEY: misc_feature
<222> LOCATION: (920)..(920)
<223> OTHER INFORMATION: N= A, U, G or C
<221> NAME/KEY: misc_feature
<222> LOCATION: (923)..(938)
<223> OTHER INFORMATION: N= A, U, G or C
<221> NAME/KEY: misc_feature
<222> LOCATION: (940)..(940)
<223> OTHER INFORMATION: N= A, U, G or C
<221> NAME/KEY: misc_feature
<222> LOCATION: (943)..(944)
<223> OTHER INFORMATION: N= A, U, G or C
<221> NAME/KEY: misc_feature
<222> LOCATION: (946)..(947)

<223> OTHER INFORMATION: N= A, U, G or C
<221> NAME/KEY: misc_feature
<222> LOCATION: (949)..(951)
<223> OTHER INFORMATION: N= A, U, G or C
<221> NAME/KEY: misc_feature
<222> LOCATION: (953)..(953)
<223> OTHER INFORMATION: N= A, U, G or C
<221> NAME/KEY: misc_feature
<222> LOCATION: (955)..(955)
<223> OTHER INFORMATION: N= A, U, G or C
<221> NAME/KEY: misc_feature
<222> LOCATION: (957)..(957)
<223> OTHER INFORMATION: N= A, U, G or C
<221> NAME/KEY: misc_feature
<222> LOCATION: (961)..(962)
<223> OTHER INFORMATION: N= A, U, G or C
<221> NAME/KEY: misc_feature
<222> LOCATION: (964)..(964)
<223> OTHER INFORMATION: N= A, U, G or C
<221> NAME/KEY: misc_feature
<222> LOCATION: (966)..(968)
<223> OTHER INFORMATION: N= A, U, G or C
<221> NAME/KEY: misc_feature
<222> LOCATION: (971)..(972)
<223> OTHER INFORMATION: N= A, U, G or C
<221> NAME/KEY: misc_feature
<222> LOCATION: (974)..(974)
<223> OTHER INFORMATION: N= A, U, G or C
<221> NAME/KEY: misc_feature
<222> LOCATION: (979)..(979)
<223> OTHER INFORMATION: N= A, U, G or C
<221> NAME/KEY: misc_feature
<222> LOCATION: (984)..(984)
<223> OTHER INFORMATION: N= A, U, G or C
<221> NAME/KEY: misc_feature
<222> LOCATION: (991)..(991)
<223> OTHER INFORMATION: N= A, U, G or C
<221> NAME/KEY: misc_feature
<222> LOCATION: (993)..(994)
<223> OTHER INFORMATION: N= A, U, G or C
<221> NAME/KEY: misc_feature
<222> LOCATION: (996)..(998)
<223> OTHER INFORMATION: N= A, U, G or C
<221> NAME/KEY: misc_feature
<222> LOCATION: (1004)..(1008)
<223> OTHER INFORMATION: N= A, U, G or C
<221> NAME/KEY: misc_feature
<222> LOCATION: (1011)..(1018)
<223> OTHER INFORMATION: N= A, U, G or C
<221> NAME/KEY: misc_feature
<222> LOCATION: (1026)..(1026)
<223> OTHER INFORMATION: N= A, U, G or C
<221> NAME/KEY: misc_feature
<222> LOCATION: (1030)..(1030)
<223> OTHER INFORMATION: N= A, U, G or C
<221> NAME/KEY: misc_feature
<222> LOCATION: (1033)..(1033)
<223> OTHER INFORMATION: N= A, U, G or C
<221> NAME/KEY: misc_feature
<222> LOCATION: (1037)..(1042)
<223> OTHER INFORMATION: N= A, U, G or C
<221> NAME/KEY: misc_feature
<222> LOCATION: (1044)..(1045)
<223> OTHER INFORMATION: N= A, U, G or C
<221> NAME/KEY: misc_feature
<222> LOCATION: (1047)..(1047)
<223> OTHER INFORMATION: N= A, U, G or C
<221> NAME/KEY: misc_feature
<222> LOCATION: (1051)..(1053)
<223> OTHER INFORMATION: N= A, U, G or C
<221> NAME/KEY: misc_feature
<222> LOCATION: (1058)..(1058)
<223> OTHER INFORMATION: N= A, U, G or C
<221> NAME/KEY: misc_feature
<222> LOCATION: (1078)..(1078)
<223> OTHER INFORMATION: N= A, U, G or C
<221> NAME/KEY: misc_feature
<222> LOCATION: (1080)..(1080)
<223> OTHER INFORMATION: N= A, U, G or C -continued
<221> NAME/KEY: misc_feature
<222> LOCATION: (1083)..(1083)
<223> OTHER INFORMATION: N= A, U, G or C
<221> NAME/KEY: misc_feature
<222> LOCATION: (1089)..(1090)
<223> OTHER INFORMATION: N= A, U, G or C
<221> NAME/KEY: misc_feature
<222> LOCATION: (1097)..(1097)
<223> OTHER INFORMATION: N= A, U, G or C
<221> NAME/KEY: misc_feature
<222> LOCATION: (1106)..(1107)
<223> OTHER INFORMATION: N= A, U, G or C
<221> NAME/KEY: misc_feature
<222> LOCATION: (1110)..(1110)
<223> OTHER INFORMATION: N= A, U, G or C
<221> NAME/KEY: misc_feature
<222> LOCATION: (1113)..(1119)
<223> OTHER INFORMATION: N= A, U, G or C
<221> NAME/KEY: misc_feature
<222> LOCATION: (1124)..(1124)
<223> OTHER INFORMATION: N= A, U, G or C
<221> NAME/KEY: misc_feature
<222> LOCATION: (1127)..(1128)
<223> OTHER INFORMATION: N= A, U, G or C
<221> NAME/KEY: misc_feature
<222> LOCATION: (1131)..(1131)
<223> OTHER INFORMATION: N= A, U, G or C
<221> NAME/KEY: misc_feature
<222> LOCATION: (1134)..(1134)
<223> OTHER INFORMATION: N= A, U, G or C
<221> NAME/KEY: misc_feature
<222> LOCATION: (1139)..(1139)
<223> OTHER INFORMATION: N= A, U, G or C
<221> NAME/KEY: misc_feature
<222> LOCATION: (1144)..(1151)
<223> OTHER INFORMATION: N= A, U, G or C
<221> NAME/KEY: misc_feature
<222> LOCATION: (1157)..(1162)
<223> OTHER INFORMATION: N= A, U, G or C
<221> NAME/KEY: misc_feature
<222> LOCATION: (1164)..(1185)
<223> OTHER INFORMATION: N= A, U, G or C
<221> NAME/KEY: misc_feature
<222> LOCATION: (1191)..(1192)
<223> OTHER INFORMATION: N= A, U, G or C
<221> NAME/KEY: misc_feature
<222> LOCATION: (1199)..(1211)
<223> OTHER INFORMATION: N= A, U, G or C
<221> NAME/KEY: misc_feature
<222> LOCATION: (1216)..(1222)
<223> OTHER INFORMATION: N= A, U, G or C
<221> NAME/KEY: misc_feature
<222> LOCATION: (1224)..(1225)
<223> OTHER INFORMATION: N= A, U, G or C
<221> NAME/KEY: misc_feature
<222> LOCATION: (1227)..(1233)
<223> OTHER INFORMATION: N= A, U, G or C
<221> NAME/KEY: misc_feature
<222> LOCATION: (1238)..(1246)
<223> OTHER INFORMATION: N= A, U, G or C
<221> NAME/KEY: misc_feature
<222> LOCATION: (1251)..(1251)
<223> OTHER INFORMATION: N= A, U, G or C
<221> NAME/KEY: misc_feature
<222> LOCATION: (1253)..(1253)
<223> OTHER INFORMATION: N= A, U, G or C
<221> NAME/KEY: misc_feature
<222> LOCATION: (1257)..(1258)
<223> OTHER INFORMATION: N= A, U, G or C
<221> NAME/KEY: misc_feature
<222> LOCATION: (1260)..(1261)
<223> OTHER INFORMATION: N= A, U, G or C
<221> NAME/KEY: misc_feature
<222> LOCATION: (1264)..(1264)
<223> OTHER INFORMATION: N= A, U, G or C
<221> NAME/KEY: misc_feature
<222> LOCATION: (1269)..(1269)
<223> OTHER INFORMATION: N= A, U, G or C
<221> NAME/KEY: misc_feature -continued
<222> LOCATION: (1273)..(1280)
<223> OTHER INFORMATION: N= A, U, G or C
<221> NAME/KEY: misc_feature
<222> LOCATION: (1285)..(1285)
<223> OTHER INFORMATION: N= A, U, G or C
<221> NAME/KEY: misc_feature
<222> LOCATION: (1287)..(1288)
<223> OTHER INFORMATION: N= A, U, G or C
<221> NAME/KEY: misc_feature
<222> LOCATION: (1290)..(1294)
<223> OTHER INFORMATION: N= A, U, G or C
<221> NAME/KEY: misc_feature
<222> LOCATION: (1296)..(1296)
<223> OTHER INFORMATION: N= A, U, G or C
<221> NAME/KEY: misc_feature
<222> LOCATION: (1300)..(1300)
<223> OTHER INFORMATION: N= A, U, G or C
<221> NAME/KEY: misc_feature
<222> LOCATION: (1302)..(1304)
<223> OTHER INFORMATION: N= A, U, G or C
<221> NAME/KEY: misc_feature
<222> LOCATION: (1306)..(1306)
<223> OTHER INFORMATION: N= A, U, G or C
<221> NAME/KEY: misc_feature
<222> LOCATION: (1311)..(1311)
<223> OTHER INFORMATION: N= A, U, G or C
<221> NAME/KEY: misc_feature
<222> LOCATION: (1316)..(1321)
<223> OTHER INFORMATION: N= A, U, G or C
<221> NAME/KEY: misc_feature
<222> LOCATION: (1323)..(1323)
<223> OTHER INFORMATION: N= A, U, G or C
<221> NAME/KEY: misc_feature
<222> LOCATION: (1325)..(1325)
<223> OTHER INFORMATION: N= A, U, G or C
<221> NAME/KEY: misc_feature
<222> LOCATION: (1327)..(1328)
<223> OTHER INFORMATION: N= A, U, G or C
<221> NAME/KEY: misc_feature
<222> LOCATION: (1331)..(1336)
<223> OTHER INFORMATION: N= A, U, G or C
<221> NAME/KEY: misc_feature
<222> LOCATION: (1341)..(1341)
<223> OTHER INFORMATION: N= A, U, G or C
<221> NAME/KEY: misc_feature
<222> LOCATION: (1347)..(1349)
<223> OTHER INFORMATION: N= A, U, G or C
<221> NAME/KEY: misc_feature
<222> LOCATION: (1356)..(1357)
<223> OTHER INFORMATION: N= A, U, G or C
<221> NAME/KEY: misc_feature
<222> LOCATION: (1361)..(1361)
<223> OTHER INFORMATION: N= A, U, G or C
<221> NAME/KEY: misc_feature
<222> LOCATION: (1363)..(1363)
<223> OTHER INFORMATION: N= A, U, G or C
<221> NAME/KEY: misc_feature
<222> LOCATION: (1366)..(1366)
<223> OTHER INFORMATION: N= A, U, G or C
<221> NAME/KEY: misc_feature
<222> LOCATION: (1368)..(1368)
<223> OTHER INFORMATION: N= A, U, G or C
<221> NAME/KEY: misc_feature
<222> LOCATION: (1370)..(1371)
<223> OTHER INFORMATION: N= A, U, G or C
<221> NAME/KEY: misc_feature
<222> LOCATION: (1375)..(1376)
<223> OTHER INFORMATION: N= A, U, G or C
<221> NAME/KEY: misc_feature
<222> LOCATION: (1382)..(1383)
<223> OTHER INFORMATION: N= A, U, G or C
<221> NAME/KEY: misc_feature
<222> LOCATION: (1385)..(1387)
<223> OTHER INFORMATION: N= A, U, G or C
<221> NAME/KEY: misc_feature
<222> LOCATION: (1391)..(1392)
<223> OTHER INFORMATION: N= A, U, G or C
<221> NAME/KEY: misc_feature
<222> LOCATION: (1400)..(1402)

-continued

<223> OTHER INFORMATION: N= A, U, G or C
<221> NAME/KEY: misc_feature
<222> LOCATION: (1405)..(1425)
<223> OTHER INFORMATION: N= A, U, G or C
<221> NAME/KEY: misc_feature
<222> LOCATION: (1430)..(1435)
<223> OTHER INFORMATION: N= A, U, G or C
<221> NAME/KEY: misc_feature
<222> LOCATION: (1437)..(1454)
<223> OTHER INFORMATION: N= A, U, G or C
<221> NAME/KEY: misc_feature
<222> LOCATION: (1566)..(1567)
<223> OTHER INFORMATION: N= A, U, G or C
<221> NAME/KEY: misc_feature
<222> LOCATION: (1573)..(1599)
<223> OTHER INFORMATION: N= A, U, G or C
<221> NAME/KEY: misc_feature
<222> LOCATION: (1606)..(1607)
<223> OTHER INFORMATION: N= A, U, G or C
<221> NAME/KEY: misc_feature
<222> LOCATION: (1622)..(1622)
<223> OTHER INFORMATION: N= A, U, G or C
<221> NAME/KEY: misc_feature
<222> LOCATION: (1624)..(1627)
<223> OTHER INFORMATION: N= A, U, G or C
<221> NAME/KEY: misc_feature
<222> LOCATION: (1629)..(1630)
<223> OTHER INFORMATION: N= A, U, G or C
<221> NAME/KEY: misc_feature
<222> LOCATION: (1634)..(1634)
<223> OTHER INFORMATION: N= A, U, G or C
<221> NAME/KEY: misc_feature
<222> LOCATION: (1636)..(1637)
<223> OTHER INFORMATION: N= A, U, G or C
<221> NAME/KEY: misc_feature
<222> LOCATION: (1639)..(1640)
<223> OTHER INFORMATION: N= A, U, G or C
<221> NAME/KEY: misc_feature
<222> LOCATION: (1644)..(1644)
<223> OTHER INFORMATION: N= A, U, G or C
<221> NAME/KEY: misc_feature
<222> LOCATION: (1646)..(1647)
<223> OTHER INFORMATION: N= A, U, G or C
<221> NAME/KEY: misc_feature
<222> LOCATION: (1650)..(1653)
<223> OTHER INFORMATION: N= A, U, G or C
<221> NAME/KEY: misc_feature
<222> LOCATION: (1656)..(1663)
<223> OTHER INFORMATION: N= A, U, G or C
<221> NAME/KEY: misc_feature
<222> LOCATION: (1672)..(1673)
<223> OTHER INFORMATION: N= A, U, G or C
<221> NAME/KEY: misc_feature
<222> LOCATION: (1679)..(1679)
<223> OTHER INFORMATION: N= A, U, G or C
<221> NAME/KEY: misc_feature
<222> LOCATION: (1681)..(1684)
<223> OTHER INFORMATION: N= A, U, G or C
<221> NAME/KEY: misc_feature
<222> LOCATION: (1690)..(1690)
<223> OTHER INFORMATION: N= A, U, G or C
<221> NAME/KEY: misc_feature
<222> LOCATION: (1697)..(1697)
<223> OTHER INFORMATION: N= A, U, G or C
<221> NAME/KEY: misc_feature
<222> LOCATION: (1699)..(1699)
<223> OTHER INFORMATION: N= A, U, G or C
<221> NAME/KEY: misc_feature
<222> LOCATION: (1704)..(1707)
<223> OTHER INFORMATION: N= A, U, G or C
<221> NAME/KEY: misc_feature
<222> LOCATION: (1709)..(1749)
<223> OTHER INFORMATION: N= A, U, G or C
<221> NAME/KEY: misc_feature
<222> LOCATION: (1751)..(1754)
<223> OTHER INFORMATION: N= A, U, G or C
<221> NAME/KEY: misc_feature
<222> LOCATION: (1756)..(1758)
<223> OTHER INFORMATION: N= A, U, G or C -continued
<221> NAME/KEY: misc_feature
<222> LOCATION: (1760)..(1762)
<223> OTHER INFORMATION: N= A, U, G or C
<221> NAME/KEY: misc_feature
<222> LOCATION: (1764)..(1770)
<223> OTHER INFORMATION: N= A, U, G or C
<221> NAME/KEY: misc_feature
<222> LOCATION: (1772)..(1772)
<223> OTHER INFORMATION: N= A, U, G or C
<221> NAME/KEY: misc_feature
<222> LOCATION: (1781)..(1782)
<223> OTHER INFORMATION: N= A, U, G or C
<221> NAME/KEY: misc_feature
<222> LOCATION: (1793)..(1794)
<223> OTHER INFORMATION: N= A, U, G or C
<221> NAME/KEY: misc_feature
<222> LOCATION: (1796)..(1797)
<223> OTHER INFORMATION: N= A, U, G or C
<221> NAME/KEY: misc_feature
<222> LOCATION: (1801)..(1801)
<223> OTHER INFORMATION: N= A, U, G or C
<221> NAME/KEY: misc_feature
<222> LOCATION: (1804)..(1805)
<223> OTHER INFORMATION: N= A, U, G or C
<221> NAME/KEY: misc_feature
<222> LOCATION: (1808)..(1808)
<223> OTHER INFORMATION: N= A, U, G or C
<221> NAME/KEY: misc_feature
<222> LOCATION: (1812)..(1813)
<223> OTHER INFORMATION: N= A, U, G or C
<221> NAME/KEY: misc_feature
<222> LOCATION: (1816)..(1816)
<223> OTHER INFORMATION: N= A, U, G or C
<221> NAME/KEY: misc_feature
<222> LOCATION: (1822)..(1822)
<223> OTHER INFORMATION: N= A, U, G or C
<221> NAME/KEY: misc_feature
<222> LOCATION: (1825)..(1826)
<223> OTHER INFORMATION: N= A, U, G or C
<221> NAME/KEY: misc_feature
<222> LOCATION: (1831)..(1831)
<223> OTHER INFORMATION: N= A, U, G or C
<221> NAME/KEY: misc_feature
<222> LOCATION: (1839)..(1839)
<223> OTHER INFORMATION: N= A, U, G or C
<221> NAME/KEY: misc_feature
<222> LOCATION: (1844)..(1845)
<223> OTHER INFORMATION: N= A, U, G or C
<221> NAME/KEY: misc_feature
<222> LOCATION: (1855)..(1856)
<223> OTHER INFORMATION: N= A, U, G or C
<221> NAME/KEY: misc_feature
<222> LOCATION: (1858)..(1866)
<223> OTHER INFORMATION: N= A, U, G or C
<221> NAME/KEY: misc_feature
<222> LOCATION: (1868)..(1872)
<223> OTHER INFORMATION: N= A, U, G or C
<221> NAME/KEY: misc_feature
<222> LOCATION: (1874)..(1884)
<223> OTHER INFORMATION: N= A, U, G or C
<221> NAME/KEY: misc_feature
<222> LOCATION: (1886)..(1888)
<223> OTHER INFORMATION: N= A, U, G or C
<221> NAME/KEY: misc_feature
<222> LOCATION: (1895)..(1896)
<223> OTHER INFORMATION: N= A, U, G or C
<221> NAME/KEY: misc_feature
<222> LOCATION: (1899)..(1899)
<223> OTHER INFORMATION: N= A, U, G or C
<221> NAME/KEY: misc_feature
<222> LOCATION: (1908)..(1909)
<223> OTHER INFORMATION: N= A, U, G or C
<221> NAME/KEY: misc_feature
<222> LOCATION: (1921)..(1922)
<223> OTHER INFORMATION: N= A, U, G or C
<221> NAME/KEY: misc_feature
<222> LOCATION: (1963)..(1963)
<223> OTHER INFORMATION: N= A, U, G or C
<221> NAME/KEY: misc_feature -continued
<222> LOCATION: (1971)..(1971)
<223> OTHER INFORMATION: N= A, U, G or C
<221> NAME/KEY: misc_feature
<222> LOCATION: (1974)..(1974)
<223> OTHER INFORMATION: N= A, U, G or C
<221> NAME/KEY: misc_feature
<222> LOCATION: (1976)..(1976)
<223> OTHER INFORMATION: N= A, U, G or C
<221> NAME/KEY: misc_feature
<222> LOCATION: (1979)..(1979)
<223> OTHER INFORMATION: N= A, U, G or C
<221> NAME/KEY: misc_feature
<222> LOCATION: (1982)..(1989)
<223> OTHER INFORMATION: N= A, U, G or C
<221> NAME/KEY: misc_feature
<222> LOCATION: (1997)..(2005)
<223> OTHER INFORMATION: N= A, U, G or C
<221> NAME/KEY: misc_feature
<222> LOCATION: (2007)..(2007)
<223> OTHER INFORMATION: N= A, U, G or C
<221> NAME/KEY: misc_feature
<222> LOCATION: (2009)..(2009)
<223> OTHER INFORMATION: N= A, U, G or C
<221> NAME/KEY: misc_feature
<222> LOCATION: (2011)..(2011)
<223> OTHER INFORMATION: N= A, U, G or C
<221> NAME/KEY: misc_feature
<222> LOCATION: (2015)..(2015)
<223> OTHER INFORMATION: N= A, U, G or C
<221> NAME/KEY: misc_feature
<222> LOCATION: (2018)..(2019)
<223> OTHER INFORMATION: N= A, U, G or C
<221> NAME/KEY: misc_feature
<222> LOCATION: (2021)..(2021)
<223> OTHER INFORMATION: N= A, U, G or C
<221> NAME/KEY: misc_feature
<222> LOCATION: (2023)..(2026)
<223> OTHER INFORMATION: N= A, U, G or C
<221> NAME/KEY: misc_feature
<222> LOCATION: (2029)..(2029)
<223> OTHER INFORMATION: N= A, U, G or C
<221> NAME/KEY: misc_feature
<222> LOCATION: (2037)..(2040)
<223> OTHER INFORMATION: N= A, U, G or C
<221> NAME/KEY: misc_feature
<222> LOCATION: (2041)..(2041)
<223> OTHER INFORMATION: N= A, U, G or C
<221> NAME/KEY: misc_feature
<222> LOCATION: (2043)..(2043)
<223> OTHER INFORMATION: N= A, U, G or C
<221> NAME/KEY: misc_feature
<222> LOCATION: (2047)..(2052)
<223> OTHER INFORMATION: N= A, U, G or C
<221> NAME/KEY: misc_feature
<222> LOCATION: (2067)..(2068)
<223> OTHER INFORMATION: N= A, U, G or C
<221> NAME/KEY: misc_feature
<222> LOCATION: (2070)..(2070)
<223> OTHER INFORMATION: N= A, U, G or C
<221> NAME/KEY: misc_feature
<222> LOCATION: (2072)..(2072)
<223> OTHER INFORMATION: N= A, U, G or C
<221> NAME/KEY: misc_feature
<222> LOCATION: (2080)..(2081)
<223> OTHER INFORMATION: N= A, U, G or C
<221> NAME/KEY: misc_feature
<222> LOCATION: (2083)..(2085)
<223> OTHER INFORMATION: N= A, U, G or C
<221> NAME/KEY: misc_feature
<222> LOCATION: (2087)..(2089)
<223> OTHER INFORMATION: N= A, U, G or C
<221> NAME/KEY: misc_feature
<222> LOCATION: (2091)..(2091)
<223> OTHER INFORMATION: N= A, U, G or C
<221> NAME/KEY: misc_feature
<222> LOCATION: (2094)..(2108)
<223> OTHER INFORMATION: N= A, U, G or C
<221> NAME/KEY: misc_feature
<222> LOCATION: (2112)..(2113)

<223> OTHER INFORMATION: N= A, U, G or C
<221> NAME/KEY: misc_feature
<222> LOCATION: (2116)..(2116)
<223> OTHER INFORMATION: N= A, U, G or C
<221> NAME/KEY: misc_feature
<222> LOCATION: (2123)..(2123)
<223> OTHER INFORMATION: N= A, U, G or C
<221> NAME/KEY: misc_feature
<222> LOCATION: (2128)..(2128)
<223> OTHER INFORMATION: N= A, U, G or C
<221> NAME/KEY: misc_feature
<222> LOCATION: (2130)..(2132)
<223> OTHER INFORMATION: N= A, U, G or C
<221> NAME/KEY: misc_feature
<222> LOCATION: (2135)..(2142)
<223> OTHER INFORMATION: N= A, U, G or C
<221> NAME/KEY: misc_feature
<222> LOCATION: (2145)..(2146)
<223> OTHER INFORMATION: N= A, U, G or C
<221> NAME/KEY: misc_feature
<222> LOCATION: (2149)..(2155)
<223> OTHER INFORMATION: N= A, U, G or C
<221> NAME/KEY: misc_feature
<222> LOCATION: (2160)..(2160)
<223> OTHER INFORMATION: N= A, U, G or C
<221> NAME/KEY: misc_feature
<222> LOCATION: (2162)..(2166)
<223> OTHER INFORMATION: N= A, U, G or C
<221> NAME/KEY: misc_feature
<222> LOCATION: (2169)..(2170)
<223> OTHER INFORMATION: N= A, U, G or C
<221> NAME/KEY: misc_feature
<222> LOCATION: (2175)..(2175)
<223> OTHER INFORMATION: N= A, U, G or C
<221> NAME/KEY: misc_feature
<222> LOCATION: (2178)..(2178)
<223> OTHER INFORMATION: N= A, U, G or C
<221> NAME/KEY: misc_feature
<222> LOCATION: (2181)..(2194)
<223> OTHER INFORMATION: N= A, U, G or C
<221> NAME/KEY: misc_feature
<222> LOCATION: (2201)..(2211)
<223> OTHER INFORMATION: N= A, U, G or C
<221> NAME/KEY: misc_feature
<222> LOCATION: (2213)..(2213)
<223> OTHER INFORMATION: N= A, U, G or C
<221> NAME/KEY: misc_feature
<222> LOCATION: (2215)..(2223)
<223> OTHER INFORMATION: N= A, U, G or C
<221> NAME/KEY: misc_feature
<222> LOCATION: (2228)..(2228)
<223> OTHER INFORMATION: N= A, U, G or C
<221> NAME/KEY: misc_feature
<222> LOCATION: (2231)..(2233)
<223> OTHER INFORMATION: N= A, U, G or C
<221> NAME/KEY: misc_feature
<222> LOCATION: (2235)..(2236)
<223> OTHER INFORMATION: N= A, U, G or C
<221> NAME/KEY: misc_feature
<222> LOCATION: (2240)..(2240)
<223> OTHER INFORMATION: N= A, U, G or C
<221> NAME/KEY: misc_feature
<222> LOCATION: (2246)..(2246)
<223> OTHER INFORMATION: N= A, U, G or C
<221> NAME/KEY: misc_feature
<222> LOCATION: (2258)..(2259)
<223> OTHER INFORMATION: N= A, U, G or C
<221> NAME/KEY: misc_feature
<222> LOCATION: (2265)..(2265)
<223> OTHER INFORMATION: N= A, U, G or C
<221> NAME/KEY: misc_feature
<222> LOCATION: (2269)..(2270)
<223> OTHER INFORMATION: N= A, U, G or C
<221> NAME/KEY: misc_feature
<222> LOCATION: (2281)..(2281)
<223> OTHER INFORMATION: N= A, U, G or C
<221> NAME/KEY: misc_feature
<222> LOCATION: (2283)..(2284)
<223> OTHER INFORMATION: N= A, U, G or C -continued
<221> NAME/KEY: misc_feature
<222> LOCATION: (2292)..(2294)
<223> OTHER INFORMATION: N= A, U, G or C
<221> NAME/KEY: misc_feature
<222> LOCATION: (2297)..(2297)
<223> OTHER INFORMATION: N= A, U, G or C
<221> NAME/KEY: misc_feature
<222> LOCATION: (2299)..(2302)
<223> OTHER INFORMATION: N= A, U, G or C
<221> NAME/KEY: misc_feature
<222> LOCATION: (2305)..(2306)
<223> OTHER INFORMATION: N= A, U, G or C
<221> NAME/KEY: misc_feature
<222> LOCATION: (2309)..(2310)
<223> OTHER INFORMATION: N= A, U, G or C
<221> NAME/KEY: misc_feature
<222> LOCATION: (2314)..(2321)
<223> OTHER INFORMATION: N= A, U, G or C
<221> NAME/KEY: misc_feature
<222> LOCATION: (2325)..(2326)
<223> OTHER INFORMATION: N= A, U, G or C
<221> NAME/KEY: misc_feature
<222> LOCATION: (2329)..(2330)
<223> OTHER INFORMATION: N= A, U, G or C
<221> NAME/KEY: misc_feature
<222> LOCATION: (2332)..(2332)
<223> OTHER INFORMATION: N= A, U, G or C
<221> NAME/KEY: misc_feature
<222> LOCATION: (2334)..(2334)
<223> OTHER INFORMATION: N= A, U, G or C
<221> NAME/KEY: misc_feature
<222> LOCATION: (2338)..(2340)
<223> OTHER INFORMATION: N= A, U, G or C
<221> NAME/KEY: misc_feature
<222> LOCATION: (2343)..(2343)
<223> OTHER INFORMATION: N= A, U, G or C
<221> NAME/KEY: misc_feature
<222> LOCATION: (2345)..(2345)
<223> OTHER INFORMATION: N= A, U, G or C
<221> NAME/KEY: misc_feature
<222> LOCATION: (2350)..(2351)
<223> OTHER INFORMATION: N= A, U, G or C
<221> NAME/KEY: misc_feature
<222> LOCATION: (2354)..(2357)
<223> OTHER INFORMATION: N= A, U, G or C
<221> NAME/KEY: misc_feature
<222> LOCATION: (2360)..(2363)
<223> OTHER INFORMATION: N= A, U, G or C
<221> NAME/KEY: misc_feature
<222> LOCATION: (2371)..(2373)
<223> OTHER INFORMATION: N= A, U, G or C
<221> NAME/KEY: misc_feature
<222> LOCATION: (2380)..(2381)
<223> OTHER INFORMATION: N= A, U, G or C
<221> NAME/KEY: misc_feature
<222> LOCATION: (2384)..(2386)
<223> OTHER INFORMATION: N= A, U, G or C
<221> NAME/KEY: misc_feature
<222> LOCATION: (2398)..(2398)
<223> OTHER INFORMATION: N= A, U, G or C
<221> NAME/KEY: misc_feature
<222> LOCATION: (2402)..(2407)
<223> OTHER INFORMATION: N= A, U, G or C
<221> NAME/KEY: misc_feature
<222> LOCATION: (2414)..(2414)
<223> OTHER INFORMATION: N= A, U, G or C
<221> NAME/KEY: misc_feature
<222> LOCATION: (2418)..(2418)
<223> OTHER INFORMATION: N= A, U, G or C
<221> NAME/KEY: misc_feature
<222> LOCATION: (2437)..(2437)
<223> OTHER INFORMATION: N= A, U, G or C
<221> NAME/KEY: misc_feature
<222> LOCATION: (2441)..(2441)
<223> OTHER INFORMATION: N= A, U, G or C
<221> NAME/KEY: misc_feature
<222> LOCATION: (2443)..(2443)
<223> OTHER INFORMATION: N= A, U, G or C
<221> NAME/KEY: misc_feature -continued
<222> LOCATION: (2458)..(2458)
<223> OTHER INFORMATION: N= A, U, G or C
<221> NAME/KEY: misc_feature
<222> LOCATION: (2461)..(2464)
<223> OTHER INFORMATION: N= A, U, G or C
<221> NAME/KEY: misc_feature
<222> LOCATION: (2474)..(2474)
<223> OTHER INFORMATION: N= A, U, G or C
<221> NAME/KEY: misc_feature
<222> LOCATION: (2477)..(2477)
<223> OTHER INFORMATION: N= A, U, G or C
<221> NAME/KEY: misc_feature
<222> LOCATION: (2486)..(2489)
<223> OTHER INFORMATION: N= A, U, G or C
<221> NAME/KEY: misc_feature
<222> LOCATION: (2513)..(2513)
<223> OTHER INFORMATION: N= A, U, G or C
<221> NAME/KEY: misc_feature
<222> LOCATION: (2516)..(2516)
<223> OTHER INFORMATION: N= A, U, G or C
<221> NAME/KEY: misc_feature
<222> LOCATION: (2530)..(2530)
<223> OTHER INFORMATION: N= A, U, G or C
<221> NAME/KEY: misc_feature
<222> LOCATION: (2533)..(2534)
<223> OTHER INFORMATION: N= A, U, G or C
<221> NAME/KEY: misc_feature
<222> LOCATION: (2547)..(2548)
<223> OTHER INFORMATION: N= A, U, G or C
<221> NAME/KEY: misc_feature
<222> LOCATION: (2560)..(2561)
<223> OTHER INFORMATION: N= A, U, G or C
<221> NAME/KEY: misc_feature
<222> LOCATION: (2568)..(2568)
<223> OTHER INFORMATION: N= A, U, G or C
<221> NAME/KEY: misc_feature
<222> LOCATION: (2571)..(2571)
<223> OTHER INFORMATION: N= A, U, G or C
<221> NAME/KEY: misc_feature
<222> LOCATION: (2575)..(2575)
<223> OTHER INFORMATION: N= A, U, G or C
<221> NAME/KEY: misc_feature
<222> LOCATION: (2586)..(2586)
<223> OTHER INFORMATION: N= A, U, G or C
<221> NAME/KEY: misc_feature
<222> LOCATION: (2588)..(2588)
<223> OTHER INFORMATION: N= A, U, G or C
<221> NAME/KEY: misc_feature
<222> LOCATION: (2606)..(2606)
<223> OTHER INFORMATION: N= A, U, G or C
<221> NAME/KEY: misc_feature
<222> LOCATION: (2617)..(2617)
<223> OTHER INFORMATION: N= A, U, G or C
<221> NAME/KEY: misc_feature
<222> LOCATION: (2619)..(2620)
<223> OTHER INFORMATION: N= A, U, G or C
<221> NAME/KEY: misc_feature
<222> LOCATION: (2622)..(2622)
<223> OTHER INFORMATION: N= A, U, G or C
<221> NAME/KEY: misc_feature
<222> LOCATION: (2624)..(2624)
<223> OTHER INFORMATION: N= A, U, G or C
<221> NAME/KEY: misc_feature
<222> LOCATION: (2626)..(2626)
<223> OTHER INFORMATION: N= A, U, G or C
<221> NAME/KEY: misc_feature
<222> LOCATION: (2628)..(2630)
<223> OTHER INFORMATION: N= A, U, G or C
<221> NAME/KEY: misc_feature
<222> LOCATION: (2633)..(2635)
<223> OTHER INFORMATION: N= A, U, G or C
<221> NAME/KEY: misc_feature
<222> LOCATION: (2640)..(2642)
<223> OTHER INFORMATION: N= A, U, G or C
<221> NAME/KEY: misc_feature
<222> LOCATION: (2644)..(2646)
<223> OTHER INFORMATION: N= A, U, G or C
<221> NAME/KEY: misc_feature
<222> LOCATION: (2649)..(2650)

-continued

<223> OTHER INFORMATION: N= A, U, G or C
<221> NAME/KEY: misc_feature
<222> LOCATION: (2652)..(2652)
<223> OTHER INFORMATION: N= A, U, G or C
<221> NAME/KEY: misc_feature
<222> LOCATION: (2670)..(2674)
<223> OTHER INFORMATION: N= A, U, G or C
<221> NAME/KEY: misc_feature
<222> LOCATION: (2677)..(2678)
<223> OTHER INFORMATION: N= A, U, G or C
<221> NAME/KEY: misc_feature
<222> LOCATION: (2680)..(2680)
<223> OTHER INFORMATION: N= A, U, G or C
<221> NAME/KEY: misc_feature
<222> LOCATION: (2682)..(2682)
<223> OTHER INFORMATION: N= A, U, G or C
<221> NAME/KEY: misc_feature
<222> LOCATION: (2689)..(2691)
<223> OTHER INFORMATION: N= A, U, G or C
<221> NAME/KEY: misc_feature
<222> LOCATION: (2693)..(2693)
<223> OTHER INFORMATION: N= A, U, G or C
<221> NAME/KEY: misc_feature
<222> LOCATION: (2699)..(2701)
<223> OTHER INFORMATION: N= A, U, G or C
<221> NAME/KEY: misc_feature
<222> LOCATION: (2706)..(2708)
<223> OTHER INFORMATION: N= A, U, G or C
<221> NAME/KEY: misc_feature
<222> LOCATION: (2712)..(2713)
<223> OTHER INFORMATION: N= A, U, G or C
<221> NAME/KEY: misc_feature
<222> LOCATION: (2716)..(2716)
<223> OTHER INFORMATION: N= A, U, G or C
<221> NAME/KEY: misc_feature
<222> LOCATION: (2718)..(2719)
<223> OTHER INFORMATION: N= A, U, G or C
<221> NAME/KEY: misc_feature
<222> LOCATION: (2726)..(2727)
<223> OTHER INFORMATION: N= A, U, G or C
<221> NAME/KEY: misc_feature
<222> LOCATION: (2729)..(2730)
<223> OTHER INFORMATION: N= A, U, G or C
<221> NAME/KEY: misc_feature
<222> LOCATION: (2733)..(2736)
<223> OTHER INFORMATION: N= A, U, G or C
<221> NAME/KEY: misc_feature
<222> LOCATION: (2742)..(2743)
<223> OTHER INFORMATION: N= A, U, G or C
<221> NAME/KEY: misc_feature
<222> LOCATION: (2750)..(2750)
<223> OTHER INFORMATION: N= A, U, G or C
<221> NAME/KEY: misc_feature
<222> LOCATION: (2760)..(2762)
<223> OTHER INFORMATION: N= A, U, G or C
<221> NAME/KEY: misc_feature
<222> LOCATION: (2766)..(2766)
<223> OTHER INFORMATION: N= A, U, G or C
<221> NAME/KEY: misc_feature
<222> LOCATION: (2768)..(2770)
<223> OTHER INFORMATION: N= A, U, G or C
<221> NAME/KEY: misc_feature
<222> LOCATION: (2771)..(2774)
<223> OTHER INFORMATION: N= A, U, G or C
<221> NAME/KEY: misc_feature
<222> LOCATION: (2778)..(2779)
<223> OTHER INFORMATION: N= A, U, G or C
<221> NAME/KEY: misc_feature
<222> LOCATION: (2783)..(2785)
<223> OTHER INFORMATION: N= A, U, G or C
<221> NAME/KEY: misc_feature
<222> LOCATION: (2788)..(2788)
<223> OTHER INFORMATION: N= A, U, G or C
<221> NAME/KEY: misc_feature
<222> LOCATION: (2790)..(2809)
<223> OTHER INFORMATION: N= A, U, G or C
<221> NAME/KEY: misc_feature
<222> LOCATION: (2812)..(2814)
<223> OTHER INFORMATION: N= A, U, G or C -continued
<221> NAME/KEY: misc_feature
<222> LOCATION: (2816)..(2820)
<223> OTHER INFORMATION: N= A, U, G or C
<221> NAME/KEY: misc_feature
<222> LOCATION: (2824)..(2825)
<223> OTHER INFORMATION: N= A, U, G or C
<221> NAME/KEY: misc_feature
<222> LOCATION: (2827)..(2830)
<223> OTHER INFORMATION: N= A, U, G or C
<221> NAME/KEY: misc_feature
<222> LOCATION: (2833)..(2833)
<223> OTHER INFORMATION: N= A, U, G or C
<221> NAME/KEY: misc_feature
<222> LOCATION: (2840)..(2842)
<223> OTHER INFORMATION: N= A, U, G or C
<221> NAME/KEY: misc_feature
<222> LOCATION: (2844)..(2846)
<223> OTHER INFORMATION: N= A, U, G or C
<221> NAME/KEY: misc_feature
<222> LOCATION: (2849)..(2849)
<223> OTHER INFORMATION: N= A, U, G or C
<221> NAME/KEY: misc_feature
<222> LOCATION: (2853)..(2856)
<223> OTHER INFORMATION: N= A, U, G or C
<221> NAME/KEY: misc_feature
<222> LOCATION: (2858)..(2859)
<223> OTHER INFORMATION: N= A, U, G or C
<221> NAME/KEY: misc_feature
<222> LOCATION: (2861)..(2864)
<223> OTHER INFORMATION: N= A, U, G or C
<221> NAME/KEY: misc_feature
<222> LOCATION: (2866)..(2867)
<223> OTHER INFORMATION: N= A, U, G or C
<221> NAME/KEY: misc_feature
<222> LOCATION: (2870)..(2872)
<223> OTHER INFORMATION: N= A, U, G or C
<221> NAME/KEY: misc_feature
<222> LOCATION: (2875)..(2877)
<223> OTHER INFORMATION: N= A, U, G or C
<221> NAME/KEY: misc_feature
<222> LOCATION: (2885)..(2888)
<223> OTHER INFORMATION: N= A, U, G or C
<221> NAME/KEY: misc_feature
<222> LOCATION: (2890)..(2895)
<223> OTHER INFORMATION: N= A, U, G or C
<221> NAME/KEY: misc_feature
<222> LOCATION: (2899)..(2904)
<223> OTHER INFORMATION: N= A, U, G or C

<400> SEQUENCE: 4
nnnnaagnnn nnaagngnnn nngguggaug ccunggcnnn nnnagncgan gaaggangnn 60
nnnnncnncn nnanncnnng gnnagnngnn nnnnnncnnn nnanccnnng nunuccgaau 120
ggggnaaccc nnnnnnnnnn nnnnnnnnan nnnnnnnnnn nnnnnnnnnn nnnnnnngnn 180
nacnnnnnga anugaaacau cunaguannn nnaggaanag aaannaannn ngauuncnnn 240
nguagnggcg agcgaannng nannagncnn nnnnnnnnnn nnnnnnnnnn nnnannngaa 300
nnnnnuggna agnnnnnnnn nannngguna nannccngua nnnnaaannn nnnnnnnnnn 360
nnnnnnnnnn aguannncnn nncncgngnn annnngunng aannngnnnn gaccannnnn 420
naagncuaaa uacunnnnnn ngaccnauag ngnannagua cngugangga aaggngaaaa 480
gnacccnnnn nangggagug aaanagnncc ugaaaccnnn nncnuanaan nngunnnagn 540
nnnnnnnnnn nnnuganngc gunccuuuug nannaugnnn cngnganuun nnnunnnnng 600
cnagnuuaan nnnnnnnngn agncgnagng aaancgagun nnaanngngc gnnnagunnn 660
nngnnnnaga cncgaancnn ngugancuan nnaugnncag gnugaagnnn nnguaanann 720
nnnuggaggn ccgaacnnnn nnnnguugaa aannnnnngg augannugug nnungnggng 780
aaanncnaan cnaacnnngn nauagcuggu ucucnncgaa annnnuuuag gnnnngcnun 840

-continued

```
nnnnnnnnnn nnnnggnggu agagcacugn nnnnnnnnng gnnnnnnnnn nnnnuacnna    900
nnnnnnnnaa acuncgaaun ccnnnnnnnn nnnnnnnngn agnnanncnn ngngngnuaa    960
nnuncnnngu nnanagggna acancccaga ncnncnnnua aggncccnaa nnnnnnnnua   1020
aguggnaaan gangugnnnn nncnnanaca nnnaggangu uggcuuagaa gcagccancn   1080
uunaaagann gcguaanagc ucacunnucn agnnnnnnng cgcngannau nuancgggnc   1140
uaannnnnnn nccgaannnn nngnnnnnnn nnnnnnnnnn nnnnngguag nngagcgunn   1200
nnnnnnnnnn ngaagnnnnn nngnnannnn nnnuggannn nnnnnnagug ngnaugnngn   1260
naunaguanc gannnnnnnn guganannc n nnnncnccgn annncnaagg nuuccnnnnn   1320
nangnunnuc nnnnnngggu nagucgnnnc cuaagnngag ncnganangn nuagnngaug   1380
gnnannnggu nnauauuccn nnacnnnnnn nnnnnnnnnn nnnnngacgn nnnnngnnnn   1440
nnnnnnnnnn nnnnggnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnncnngaa aannnnnnnn nnnnnnnnnn nnnnnnnnnc guaccnnaaa ccgacacagg   1620
ungnnnngnn gagnanncnn aggngnnngn nnnaannnnn nnnaaggaac unngcaaanu   1680
nnnnccguan cuucggnana aggnnnncnn nnnnnnnnnn nnnnnnnnnn nnnnnnnnnn   1740
nnnnnnnnng nnnnannnan nngnnnnnnn cnacuguuua nnaaaaacac agnncnnugc   1800
naanncgnaa gnnganguau anggnnugac nccugcccng ugcnngaagg uuaanngnnn   1860
nnnnnngnnn nngnnnnnnn nnnnannnaa gcccnnguna acggcggnng uaacuauaac   1920
nnuccuaagg uagcgaaauu ccuugucggg uaaguuccga ccngcacgaa nggngnaang   1980
annnnnnnnc ugucucnnnn nnnnncncng ngaanuunna nunnnnguna agaugcnnnn   2040
uncncgcnnn nngacggaaa gaccccnngn ancuuuacun nannnunnna nugnnnnnnn   2100
nnnnnnnnug unnagnauag gunggagncn nngannnnnn nncgnnagnn nnnnnggagn   2160
cnnnnnugnn auacnacncu nnnnnnnnnn nnnnucuaac nnnnnnnnnn nancnnnnnn   2220
nnngacanug nnngnngggn aguuunacug gggcggunnc cuccnaaann guaacggagg   2280
ngnncnaagg unnncunann nnggnnggnn aucnnnnnnn nagunnaann gnanaagnnn   2340
gcnunacugn nagnnnnacn nnncgagcag nnncgaaagn nggnnnuagu gauccggngg   2400
unnnnnnugg aagngccnuc gcucaacgga uaaaagnuac ncnggggaua acaggcunau   2460
nnnncccaag aguncanauc gacggnnnng uuuggcaccu cgaugucggc ucnucncauc   2520
cuggggcugn agnnggucc c aagggunngg cuguucgccn nuuaaagngg nacgngagcu   2580
ggguunanaa cgucgugaga caguungguc ccuaucngnn gngngngnnn gannnuugan   2640
nngnnnugnn cnuaguacga gaggaccggn nngnacnnan cncuggugnn ncnguugunn   2700
ngccannngc anngcngnnu agcuannunn ggnnnngaua anngcugaan gcaucuaagn   2760
nngaancnnn cnnnnagann agnnnucncn nnnnnnnnnn nnnnnnnnna gnnncnnnnn   2820
agannannnn gungauaggn nngnnnugna agnnnngnna nnnnunnagn nnacnnnuac   2880
uaaunnnncn nnnnncuunn nnnn                                          2904
```

<210> SEQ ID NO 5
<211> LENGTH: 13
<212> TYPE: DNA
<213> ORGANISM: Artificial Sequence
<220> FEATURE:
<221> NAME/KEY: misc_feature
<223> OTHER INFORMATION: Primer -continued

```
<400> SEQUENCE: 5

cgtggtgacc ctt                                                          13


<210> SEQ ID NO 6
<211> LENGTH: 14
<212> TYPE: DNA
<213> ORGANISM: Artificial Sequence
<220> FEATURE:
<221> NAME/KEY: misc_feature
<223> OTHER INFORMATION: Primer

<400> SEQUENCE: 6

cgtcgtcacc gcta                                                         14


<210> SEQ ID NO 7
<211> LENGTH: 13
<212> TYPE: DNA
<213> ORGANISM: Artificial Sequence
<220> FEATURE:
<221> NAME/KEY: misc_feature
<223> OTHER INFORMATION: Primer

<400> SEQUENCE: 7

cgtggtaccc ctt                                                          13
```